US008748091B2

(12) United States Patent
Timp et al.

(10) Patent No.: US 8,748,091 B2
(45) Date of Patent: Jun. 10, 2014

(54) CHARACTERIZING STRETCHED POLYNUCLEOTIDES IN A SYNTHETIC NANOPASSAGE

(75) Inventors: Gregory Timp, South Bend, IN (US); Winston Timp, Baltimore, MD (US); Utkur Mirsaidov, Urbana, IL (US); Aleksei Aksimentiev, Urbana, IL (US); Jeffrey Comer, Urbana, IL (US)

(73) Assignees: The Board of Trustees of the University of Illinois, Urbana, IL (US); The John Hopkins University, Baltimore, MD (US)

( * ) Notice: Subject to any disclaimer, the term of this patent is extended or adjusted under 35 U.S.C. 154(b) by 590 days.

(21) Appl. No.: 12/971,240

(22) Filed: Dec. 17, 2010

(65) Prior Publication Data
US 2011/0226623 A1 Sep. 22, 2011

Related U.S. Application Data

(60) Provisional application No. 61/287,974, filed on Dec. 18, 2009.

(51) Int. Cl.
| | |
|---|---|
| C12Q 1/68 | (2006.01) |
| C12M 1/36 | (2006.01) |
| G01N 27/00 | (2006.01) |
| C07H 21/04 | (2006.01) |
| G01N 27/414 | (2006.01) |
| B01L 3/00 | (2006.01) |

(52) U.S. Cl.
CPC .......... *C12Q 1/6869* (2013.01); *G01N 27/4146* (2013.01); *B01L 3/5027* (2013.01)
USPC ...... 435/6.1; 435/283.1; 422/82.05; 205/543; 536/23.1

(58) Field of Classification Search
None
See application file for complete search history.

(56) References Cited

U.S. PATENT DOCUMENTS

| 5,795,782 A | 8/1998 | Church et al. |
| 6,174,709 B1 | 1/2001 | Kenten et al. |

(Continued)

FOREIGN PATENT DOCUMENTS

| WO | WO2008/079169 | | 7/2008 |
| WO | WO2009/030953 | * | 3/2009 |
| WO | WO 2010/080617 | | 7/2010 |

OTHER PUBLICATIONS

Akeson et al. (Dec. 1999) "Microsecond Time-Scale Discrimination Among Segments within Single RNA Molecules," *Biophys. J.* 77(6):3227-3233.

(Continued)

*Primary Examiner* — Betty Forman
(74) *Attorney, Agent, or Firm* — Lathrop & Gage LLP

(57) ABSTRACT

Methods of trapping a deformed portion of a double-stranded polynucleotide in a membrane nanopassage are provided. In an aspect, the membrane has a nanopassage that defines a confine region, wherein the membrane separates a first fluid compartment from a second fluid compartment, and the nanopassage is in fluid communication with the first and second compartments. A polynucleotide is provided to the first fluid compartment and optionally a threshold voltage for the membrane and the polynucleotide is determined. A driving voltage across the membrane that is greater than the threshold voltage is applied to force a portion of the polynucleotide sequence into the nanopassage confine region, and decreased to a holding voltage bias to trap the polynucleotide portion in the nanopassage confine region. In particular, at least one nucleotide base-pair is fixably positioned in the nanopassage confine volume. In further embodiments, any of the trapping methods are used to characterize or sequence double stranded DNA.

37 Claims, 18 Drawing Sheets

(56) References Cited

U.S. PATENT DOCUMENTS

| | | | |
|---|---|---|---|
| 6,300,071 B1 | 10/2001 | Vuylsteke et al. | |
| 6,605,432 B1 | 8/2003 | Huang | |
| 6,693,051 B2 | 2/2004 | Muller et al. | |
| 7,045,319 B2 | 5/2006 | Hanna | |
| 7,144,701 B2 | 12/2006 | Huang | |
| 7,186,512 B2 | 3/2007 | Martienssen et al. | |
| 7,214,485 B2 | 5/2007 | Belinsky et al. | |
| 7,226,738 B2 | 6/2007 | Hanna et al. | |
| 7,358,048 B2 | 4/2008 | Baraby et al. | |
| 7,432,050 B2 | 10/2008 | Markowitz | |
| 8,394,584 B2 | 3/2013 | Timp et al. | |
| 2006/0183112 A1 | 8/2006 | Min et al. | |
| 2009/0084688 A1 | 4/2009 | Leburton et al. | |
| 2009/0136958 A1* | 5/2009 | Gershow et al. | 435/6 |
| 2012/0040343 A1 | 2/2012 | Timp et al. | |

OTHER PUBLICATIONS

Akiyama et al. (Dec. 2003) "GATA-4 and GATA-5 Transcription Factor Genes and Potential Downstream Antitumor Target Genes are Epigeneticallu Silenced in Colorectal and Gastric Cancer," *Mol. Cell. Biol.* 23(23):8429-8439.

Akselrod et al. (Nov. 2006) "Laser-Guided Assembly of Heterotypic 3D Living Cell Microarrays," *Biophys. J.* 91(9):3465-3473.

Aksimentiev et al. (2008) "Nanomedicine: Stretching Genes with a Synthetic Nanopre," Slides presented at the Center for Nanoscale Science and Technology, Nanotechnology Workshop 2008; Beckman Institute for Advanced Science and Technology; and the Micro and Nanotechnology Laboratory (MNTL) Auditorium, University of Illinois, Urbana, IL Sep. 4-5.

Aksimentiev et al. (Sep. 2004) "Microscopic Kinetics of DNA Translocation Through Synthetic Nanopores," *Biophys. J.* 87:2086-2097.

Aksimentiev et al. (Jun. 2005) "Imaging Alpha-Hemolysin with Molecular Dynamics: Ionic Conductance, Osmotic Permeability and the Electrostatic Potential Map," *Biophys. J.* 88:3745-3761.

Ashkenasy et al. (2005) "Recognizing a Single Base in an Individual DNA Strand: A Step Toward DNA Sequencing in Nanopores," *Angew. Chem. Int. Ed. Engle.* 44:1401-1404.

Astier et al. (2006) "Toward Single Molecule DNA Sequencing: Direct Identification of Ribonuclease and Deoxyribonucleoside-Monophosphates by Using an Engineered Protein Nanopore Equipped with a Molecular Adapter," *J. Am. Chem. Soc.* 128(5):1705-1710.

Bachman et al. (Feb. 15, 1999) "Methylation-Associated Silencing of the Tissue Inhibitor of Metalloproteinase-3 Gene Suggests a Suppressor Role in Kidney, Brain, and Other Human Cancers," *Cancer Res.* 59(4):798-802.

Badal et al. (Jun. 2003) "CpG Methylation of Human Papilomavirus Type 16 DNA in Cervical Cancer Cell Lines and in Clinical Specimens: Genomic Hypomethylation Correlates with Carcinogenic Progression," *J. Virol.* 77(11):6227-6234.

Barski et al. (May 18, 2007) "High-Resolution Profiling of Histone Methylations in the Human Genome," *Cell* 129(4):823-837.

Baylay et al. (Sep. 13, 2001) "Stochastic Sensors Inspired by Biolog," *Nature* 413(6852)226-230.

Bejerano et al. (2004) "Into the Heart of Darkness: Large-Scale Clustering of Human Non-Coding DNA," *Bioinformatics* 20(1):i40-i48.

Bell, G. (May 12, 1978) "Models of the Specific Adhesion of Cells to Cells," *Science* 200:618-627.

Bell et al. (May 25, 2002) "Methylation of a CTCF-Dependent Boundary Controls Imprinted Expression of the IGF2 Gene," *Nature* 405:482-485.

Benner et al. (Jun. 2000) "Gene Expression Analysis by Massively Parallel Signature Sequencing (MPSS) on Microbead Arrays," *Nat. Biotechnol.* 18:630-634.

Birney et al. (Jun. 14, 2007) "Identification and Analysis of Functional Elements in 1% of the Human Genome by the ENCODE Pilot Project," *Nature* 447:799-816.

Bookout et al. (2006) "High-Throughput Real-Time Quantitative Reverse Transcription PCR," *Curr. Protocols Mol. Biol.* Ch. 15, unit 15 18.

Botstein et al. (1980) "Construction of a Genetic Linkage Map in Man Using Restriction Length Polymorphisms," *Am. J. Hum. Genet.* 32:314-331.

Branton et al. (Oct. 2008) "The Potential and Challenges of Nanopore Sequencing," *Nature Biotechnol.* 26(10):1146-1153.

Braslavski et al. (Apr. 1, 2001) "Sequence Information can be Obtained from Single DNA Molecules," *Proc. Nat. Acad. Sci. USA* 100(7):3960-3964.

Brena et al. (Dec. 2006) "Toward a Human Epigenome," *Nature Genetics* 38(12):1359-1360.

Bustamente et al. (2000) "Single-Molecule Studies of DNA Mechanics" *Curr. Opin. Struct. Biol.* 10:279-285.

Cady et al. (2003) "Nucleic Acid Purification using Microfabricated Silicon Structures," *Biosesnsors and Bioelectrics* 19(1):59-66.

Callinan et al. (2006) "The Emerging Science of Epigenomics," *Human Mol. Gen.* 15:R95-R101.

Catteau et al. (2002) "BRCA1 Methylation: A Significant Role in Tumour Development," *Sem. Cancer Biol.* 12:359-371.

Chang et al. (Web Release Jul. 7, 2004) "DNA-Mediated Fluctuations in the Ionic Current Through Silicon Oxide Nanopore Channels," *Nano Lett.* 4(8):1551-1556.

Chazalviel, J.N. (1979) "Schottky Barrier Height and Reverse Current of the n-Si-Electrolyte Junction," *Surf. Sci.* 88:204-220.

Chemla et al. (Web Release Jun. 27, 2005) "Bias Voltage Dependent Electrochemical Impedance Spectroscopy of p and n-type Silicon Substrates," *Electrochimica Acta*. 51:665-676.

Chen et al. (Web Release Oct. 26, 2004) "Probing Single DNA Molecule Transport Using Fabricated Nanopores" *Nano Lett.* 4(11):2293-2298.

Chen et al. (Web Release Jan. 5, 2001) "Evidence that Silencing of the HPRT Promoter by DNA Methylation is Mediated by Critical CpG Sites," *J. Biol. Chem.* 276:320-328.

Cho et al. (2003) "Promoter Hypomethylation of a Novel Cancer/Testis Antigen Gene CAGE is Correlated with its Aberrant Expression and is Seen in Premalingnant Stage of Gastric Carcinoma," *Biochem. Biophys. Res. Commun.* 307(1):52-63.

Clark et al. (1994) "High Sensitivity Mapping of Methylated Cytosines," *Nuc. Acids Res.* 22 (15):2990-2997.

Clerke et al. (Apr. 2009) "Continuous Base Identification for Single-Molecule Nanopore DNA Sequencing," *Nat. Nanotechnol.* 4:265-270.

Cluzel-Schaumann et al. (Apr. 2000) "Mechanical Stability of Single DNA Molecules" *Biophysical J.* 78:1997-2006.

Cockroft et al. (2008) "A Single—Molecule Nanopore Device Detects DNA Polymerase Activity with Single-Nucleotide Resolution," *J. AM. Chem. Soc.*130(3):818-820.

Comer et al. (Jan. 2009) "Microscopic Mechanics of Hairpin DNA Translocation Through Synthetic Nanopores," *Biophys. J.* 96:593-608.

Costello et al. (Feb. 2000) "Aberrant CpG-Island Methylation has Non-Random and Tumour-Type- Specific Patterns," *Nature Genet.* 24:132-138.

Cross et al. (Mar. 1994) "Purification of CpG Islands Using a Methylated DNA Binding Column," *Nat. Genet.*6(3):236-244.

Cruz-Chu et al. (Web Release Pct. 13, 2006) "Water-Silica Force Field for Simulating Nanodevices," *J. Phys. Chem. B* 110:21497-21508.

Cruz-Chu et al. (2009) "Molecular Control of Ionic Conduction in Polymer Nanopores," *Faraday Disc.* 143:47-62.

Deamer et al. (Web Release Sep. 27, 2002) "Characterization of Nucleic Acids by Nanopore Analysis," *Acc. Chem. Res.* 35(10):817-825.

Derreumaux et al. (2001) "Impact of CpG Methylation on Structure, Dynamics and Salvation of cAMP DNA Responsive Element," *Nuc. Acids Res.* 29(11):2314-2326.

Dicke, R.H. (Jul. 1946) "The Measurement of Thermal Radiation at Microwave Frequencies," *Rev. Sci. Instrum.* 17(7):268-275.

Dimitrov et al. (2006) "Exploring the Prospects for a Nanometer-Scale Gene Chip," *IEDM Proceedings* :169-172.

(56) References Cited

OTHER PUBLICATIONS

Dimitrov et al. (2010) "Nanopores in Solid-State Membranes Engineered for Single-Molecule Detection," *Nanotechnology* 21:065502.
Dimitriov et al. (2005) "High Performance, sub-50nm MOSFETS for mixed signal Applications," *IEDM Tech Digest* :213-216.
Dimitrov et al. (2008) "Small-Signal Performance and Modeling of Sub-50nm nMOSFETs with FT above 460-GHz," *Solid State Electronics* 52:899-908.
Dimitrov et al. (2005) "High-Performance, sub 50nm nMOSFET with 290-GHz ft for Mixed Signam Amplification," *IEDM 2005 Proceedings*.
Dorset et al. (1975) "Excess Electrical Noie During Current Flow Through Porous Membranes Separating Ionic Solutions," *J. Membr. Biol.* 21: 291-309.
Dorvel et al. (2009) "Analyzing the Forces Binding a Restriction Endonuclease to DNA Using a Synthetic Nanopore," *Nuc. Acids Res.* 37(12):4170-4179.
Drmanac, R. (2001) "DNA Sequencing by Hybridization with Arrays of Samples or Probes," *Methods Mol. Biol.* 170:173-179.
Dudko et al. (Mar. 17, 2006) "Intrinsic Rates and Activation Free Energies from Single Molecule Pulling Experiments," *Phys. Rev. Lett.* 96:108101.
Dudko et al. (Jun. 2007) "Extraction Kinetics from Single-Molecule Force Spectroscopy: Nanopore Unzipping of DNA Hairpins," *Biophys. J.* 92:4188-4195.
Eads et al. (Apr. 15, 2000) "MethylLight: a High-Throughput Assay T-Measure DNA Methylation" *Nuc. Acids Res.* 28(8):e32-00.
Eckhardt et al. (Dec. 2006) "DNA Methylation Profiling of Human Chromosomes 6,20,22" *Nature Genet.* 38:1378-1385.
Esteller et al. (May 1, 2000) "Inactivation of the DNA Repair Gene O6-Methylguanine-DNA Methyltransferase by Promoter Hypermethylation is Associated with G to A Mutations in K-ras in Colorectal Tumorigenesis," *Cancer Res.* 60(9):2368-2371.
Esteller et al. (Apr. 5, 2000) "Promoter Hypermethylation and BRCA1 Inactiveation in Sporadic Breast and Ovarian Tumors," *J. Nat. Cancer Inst.* 92(7):564-569.
Esteller et al. (2000) "Epigenetic Inactivation of LKB1 in Primary Tumors Associated with Peutz-Jeghers Syndrom," *Oncogene* 19(1):164-168.
Esteller et al. (Apr. 15, 2001) "A Gene Hypermethylation Profile of Human Cancer," *Cancer Res.* 61(8):3225-3229.
Evans et al. (Apr. 1997) "Dynamic Strength of Molecular Adhesion Bonds," *Biophys. J.* 72:1541-1555.
Evans et al. (Jun. 1995) "Sensitive Force Technique to Probe Molecular Adhesion and Structural Linkages at Biological Interfaces," *Biophys. J.* 68:2580-2587.
Evans et al. (Apr. 1991) "Detachment of Agglutinin-Bonded Red Blood Cells. I. Forced to Rupture Molecular-Point Attachments," *Biophys. J.* 59:838-848.
Feinberg et al. (Feb. 28, 1983) "Hypomethylation of Ras Oncogenes in Primary Human Cancers," *Biochem. Biophys. Res. Commun.* 111(1):47-54.
Fenley et al (2003) "Approach to the Limit of Counterion Condensation," *Biopolymers* 30(13-14):1191-1203.
Ferguson et al. (Jun. 1, 1995) "Demethylation of the Estrogen Receptor Gene in Estrogen Receptor-Negative Breast Cancer Cells Can Reactivate Estrogen Receptor Gene Expression," *Cancer Res.* 55(11):2279-22283.
Ferreira et al. (Nov. 2006) "Enthalpy of the B-to-Z Conformational Transition of a DNA Oligonucleotide Determined by Isothermal Titration Calorimetry," *Biophysical Journal* 91(9):3383.
Fischbein et al. (Web Release Apr. 17, 2007) "Sub-10 nm Device Fabrication in a Transmission Electron Microscope," *Nano Lett.* 7(5):1329-1337.
Fisher et al. (Sep. 2000) "Stretching Single Molecules into Novel Conformation Using the Atomic Force Microscope," *Nature Struct. Bio.* 7(9):719-724.
Fologea et al. (Web Release Aug. 9, 2005) "Slowing DNA Translocation in a Solid-State Nanopore," *Nano Lett.* 5(9):1734-1737.

Fraga et al. (2003) "The Affinity of Different MBD Proteins for a Specific Methylated Locus Depends on their Intrinsic Binding Properties," *Nuc. Acids Res.* 31(6):1765-1774.
Frederick et al. (Nov. 25, 1988) "Methylation of EcoRI Recognition Site Does Not Alter DNA Conformation: The Crystal Structure of s(CGCGAm6ATTCGCG) at 2.0-A Resolution," *J. Biol. Chem.* 263(33):17872-17879.
Friedsam et al. (2003) "Dynamic Single-Molecule Force Spectroscopy: Bond Rupture Analysis with Variable Spacer Length," *J. Phys. Cond. Matter* 15:S1709-S1723.
Furini et al. (Sep. 2008) "Model-Based Prediction of the $\alpha$-Hemolysin Structure in the Hexameric State," *Biophys. J.* 95:2265-2274.
Geahigan et al. (Web Release Mar. 30, 2000) "The Dynamic Impact of CpG Methylation in DNA," *Biochemistry* 39:4939-4946.
Gill et al. (Jun. 2, 2006) "Metagenomic Analysis of the Human Distal Gut Microbiome," *Science* 312:1355-1359.
Goychuk et al. (Mar. 19, 2002) "Ion Channel Gating: A First-Passage Time Analysis of the Kramers Type," *Proc. Nat. Acad. Sci. USA* 99:3552.
Gracheva et al. (2006) "Simulation of the Electric Response of DNA Translocation through a Semiconductor Nanopore-Capacitor" *Nanotechnol* 17:622-633.
Gracheva et al. (2006) "Electrical Signatures of Single-Stranded DNA Translocation through a Semiconductor Nanopore-Capacitor" *Nanotechnol* 17:3160-3165.
Grubmuller et al. (Feb. 16, 1996) "Ligand Binding: Molecular Mechanics Calculation of the Streptavin Biotin Rupture Force," *Science* 271:997-999.
Géeron et al. (Feb. 2000) A Unified Theory of the B-Z Transition of DNA in High and Low Concentrations of Multivalent Ions, *Biophysical J.* 78(2):1070-1083.
Guthold et al. (2001) "The Rules are Changing: Force Measurements on Single Molecules and How they Relate to Bulk Reaction Kinetics and Energies," *Biomedical Microdevices* 3(1):9-18.
Gyurcsányi, R.E. (2008) "Chemically-Modified Nanopores for Sensing," *Anal. Chem.* 27(7):627-639.
Ha et al. (Oct. 10, 2002) "Initiation and Re-Initiation of DNA Unwinding by the *Escherichia coli* Rep Helicase," *Nature* 419:638-641.
Hark et al. (2000) "CTCF Mediates Methylation-Sensitive Enhancer Blocking Activity at the H19/Igf2 Locus," *Nature* 405(6785):486-489.
Harris et al. (2008) "Single-Molecule DNA Sequencing of a Viral Genome," *Science* 320:106-109.
Heinemann et al. (1992) "CCAGGC-m5C-TGC. Helical Fine Structure, Hydration, and Comparison with CCAGGCCTGG," *J. Biological Chem.* 267(11):7332-7341.
Heng et al. (Aug. 2004) "Sizing DNA Using a Nanometer-Diameter Pore," *Biophys. J.* 87(4):2905-2911.
Heng et al. (2005) "Beyond the Gene Chip," *Bell Labs Tech. J.* 10(3):5-22.
Heng et al. (Oct. 2005) "Stretching DNA using the Electric Field in a Synthetic Nanopore," *NanoLet.* 5(10):1883-1888.
Heng et al. (Feb. 2006) "The Electromechanics of *DNA* in a Synthetic Nanopore," *Biophys. J.* 90(3):1098-1106.
Henrickson et al. (Oct. 2000) "Driven DNA Transport into an Asymmetric Nanometer-Scale Pore," *Phys. Rev. Lett.*85(14):3057-3060.
Herman et al. (Jul. 1994) "Silencing of the VHL Tumor-Suppressor Gene by DNA Methylation in Renal Carcinoma," *Proc. Nat. Acad. Sci. USA* 91(21):9700-9704.
Herman et al. (Sep. 1996) "Methylation-Specific PCR: A Novel PCR Assay for Methylation Status of CpG Islands," *Nat. Acad. Sci.* 93:9821-9826.
Herman et al. (1997) "Distinct Patterns of Inactivation of P15INK4B and p16INK4A Characterize the Major Types of Hemtological Malignancies," *Cancer Res.* 57(5):837-841.
Heymann et al. (Jul. 1999) "Elastic Properties of Poly Ethelene Glycol Studied by Molecular Dynamics Stretching Simulation," *Chem. Phys. Lett.* 307(5-6):425-432.
Heymann et al. (Apr. 1999) "AN02/DNP-hapten Unbinding Forces Studies by Molecular Dynamics Atomic Force Microscopy Simulations," *Chem. Phys. Lett.* 303(1-2):1-9.

(56) References Cited

OTHER PUBLICATIONS

Ho et al. (Feb. 2008) "MeCP2 Binding to DNA Depends upon Hydration at Methyl-CpG," *Mol. Cell* 29:525-531.
Ho et al. (Jul. 2005) "Electrolytic Transport Through a Synthetic Nanometer-Diameter Pore," *Proc. Nat. Acad. Sci. USA* 102(30):10445-10450.
Hodges-Garcia et al. (Jan. 1995) "Investigation of the Influence of Cytosine Methylation on DNA Flexibility," *J. Biol. Chem.* 270(1):197-201.
Hodges-Garcia et al. (Aug. 1992) "Cytosine Methylation can Induce Local Distortions in the Structure of Duplex DNA," *Biochemistry* 31(33)7595-7599.
Hooge et al. (1971) "Fluctuations with a 1/f Spectrum in the Conductance of Ionic Solutions and in the Voltage of Concentration Cells," *Philips Res. Reports* 26:77-.
Hornblower et al. (Apr. 2007) "Single-Molecule Analysis of DNA-Protein Complexes Using Nanopores," *Nature Meth.* 4(4):315-317.
Hseih, C.L. (Oct. 1997) "Stability of Patch Methylation and its Impact in Regions of Transcriptional Initiation and Elongation," *Mol. Cell. Biol.* 17(10):5897-5904.
Hummer et al. (Jul. 2003) "Kinetics from Nonequilibrium Single-Molecule Pulling Experiments," *Biophys. J.* 85(1):5-15.
Im et al. (Aug. 2000) A Grand Canonical Monte Carlo-Brownian Dynamics Algorithm for Simulating Ion Channels, *Biophys. J.* 79(2):788-801.
Im et al. (2002) "Ions and Counterions in a Biological Channel: A Molecular Dynamics Study of OmpF Porin from *Escherichia coli* in an Explicit Membrane with 1M KCl Aqueous Salt Solution," *J. Mol. Biol.* 319:1177-1197.
International Search Report and Written Opinion, Corresponding to International Application No. PCT/US2009/068726, Mailed Sep. 27, 2010.
Irizarry et al. (May 2008) "Comprehensive High-Throughput Arrays for Relative Methylation (CHARM)," *Genome Res.* 18(5):780-790.
Issa, J.P. (Dec. 2005) "CpG Island Methylator Phenotype in Cancer," *Nature Rev.* 4:988-993.
Jeltsch, A. (2002) "Beyond Watson and Crick: DNA Methylation and Molecular Enzymology of DNA Methyltransferases," *Chem. Bio. Chem.* 3:274-293.
Jeltsch et al. (Aug. 1994) "Pausing of the Restriction Endonuclease EcoRi During Linear Diffusion on DNA," *Biochemistry* 33(34):10215-10219.
Jen-Jaconsen, L. (1997) "Protein-*DNA* Recognition Complexes: Conservation of Structure and Binding Energy in the Transition State," *Biopolymers* 44:153-180.
Jeong et al. (Oct. 2002) "A Study of Sapphire Etching Characteristics Using BCl3-Based Inductivity Coupled Plasmas," *Jap. J. Appl. Phys.* 41(10):6206-6208.
Johnson et al. (Jun. 2007) "Genome-Wide Mapping of in Vivo Protein-Dna Interactions," *Science* 316:1497-1502.
Jones et al. (Feb. 2007) "The Epigenomics of Cancer," *Cell.* 128:683-692.
Jones et. al. (Jun. 2002) "The Fundamental Role of Epigenetic Events in Cancer," *Nature Rev. Gen.* 3:415-428.
Kane et al. (Mar. 1997) "Methylation of the hMLH1 Promoter Correlates with the Lack of Expression of hMLH1 in Sporadic Colon Tumors and Mismatch Repair-Defective Human Tumor Cell Lines," *Cancer Res.* 57(5):808-811.
Kaneda et al. (Dec. 2007) "Enhanced Sensitivity to IGF-II Signaling Links Loss of Imprinting of IGF2 to Increased Cell Proliferation and Tumor Risk," *Proc. Nat. Acad. Sci. USA* 104(52):20926-20931.
Kasianowicz et al. (Nov. 1996) "Characterization of Individual Polynucleotide Molecules Using a Membrane Channel," *Proc. Nat. Acad. Sci. USA* 93(24):13770-13773.
Keyser et al. (Jul. 2006) "Direct Force Measurements of DNA in a Solid-State Nanopore," *Nature Phys.* 2:473-475.
Khulan et al. (2006) "Comprehensive Isoschizomer Profiling of Cytosine Methylation: The HELP Assay," *Genome Res.*16(8):1046-1055.

Kim et al. (2007) "SNP Genotyping: Technologies and Biomedical Applications," *Ann. Rev. Biomed. Eng.* 9:289-320.
Kinoshita et al. (Jul. 2000) "Methylation of the Androgen Receptor Minimal Promoter Silences Transcription in Human Prostate Cancer," *Cancer Res.* 60(13):3623-3630.
Kruger et al. (1995) "McrB: A Prokaryotic Protein Specifically Recognizing DNA Containing Modified Cytosine Residues," *EMBO* 14(11):2661-2669.
Laird, P.W. (Apr. 2003) "The Power and the Promise of DNA Methylation Markers," *Nature Rev.* 3:253-266.
Lander et al. (Feb. 2001) "Initial Sequencing and Analysis of the Human Genome," *Nature* 409:860-921.
Lederer et al. (Aug. 1986) "Solution Structure of a Short DNA Fragment Studied by Neutron-Scattering," *Eur. J. Biochem.* 161(1):191-196.
Lee et al. (Web Release Jul. 3, 2001) "Controlling the Transport Properties of Gold Nanotubule Membranes Using Chemisorbed Thiols," *Chem. Mater.* 13:3236-3244.
Lefebvre et al. (Feb. 1995) "Sequence Dependent Effects of CpG Cytosine Methylation: A Joint H-NMR and P-NMR Study," *Eur. J. Biochem.* 229:445-454.
Lesser et al. (1990) "The Energetic Basis of Specificity in the *Eco*-RI Endonuclease-DNA Interaction," *Science* 250:776-786.
Li et al. (Jul. 2001) "Ion-Beam Sculpting at Nanometre Length Scales," *Nature* 412:166-169.
Likharev et al. (Apr. 1999) "Single-Electron Devices and Their Applications," *Proceedings of the IEEE* 87(4):606-632.
Lin et al. (2011) "Imaging in Real-Time with FRET the Redox Response of Tumorigenic Cells to Glutathione Pertuurbations in a Microscale Flow," *Integr. Biol.* 3:208-217.
Lippman et al. (Mar. 2005) "Profiling DNA Meththylation Patterns Using Genomic Tiling Microarrays" *Nat Meth* 2(3):219224.
Luan et al. (Sep. 2008) "Strain Softening in Stretched DNA," *Phys. Rev. Lett.*101(11):118101.
Madou et al. (Nov. 1980) "The Silicon/Silica Electrode," *Phys. Stat. Sol. A* 57:705-712.
Manning (1978) "The Molecular Theory of Polyelectrolyte Solutions with Applications to the Electrostatic Properties of Polynucleotides," *Q Rev, Biophys.* 11(2):179-246.
Marcus et al. (May 2006) "Microfluidic Single-Cell MRNA Isolation and Analysis," *Anal. Chem.* 78(9):3084-3089.
Mardis, E.R. (2008) "The Impact of Next-Generation Sequencing Technology on Genetics," *Trends Genet.* 24(3):133-141.
Martin et al. (2001) "Controlling Ion Transport Selectivity in Gold Nanotubule Membranes," *Adv. Mater.* 13: 1351-1362.
Marziali et al. (2001) "New DNA Sequencing Methods," *Ann. Rev. Biomed. Eng.* 3:195-233.
Mathé et al. (Nov. 2004) "Nanopore Unzipping of Individual DNA Hairpin Molecules," *Biophys. J.* 87:3205-3212.
Mathé et al. (Jan. 2006) "Equilibrium and Irreversible Unzipping of DNA in a Nanopore," *Europhyd. Lett.* 73(1):128-134.
McGillivray et al. (1980) "Dual-Path Capacitance Compensation Network for Microelectrode Recordings," *Am. J. Physiol.* 238:H930-H931.
Meints et al. (Sep. 2001) "Dynamic Impact of Methylation at the M Hhal Target Site: A Solid-State Deuterium NMR Study," *Biochemistry* 40(41)12436-12443.
Melin et al. (2007) "Microfluidic Large-Scale Integration: The Evolution of Design Rules for Biological Automation," *Ann. Rev. Biophys. Biomol. Struct.* 36:213-231.
Miranda et al. (2007) "DNA Methylation: The Nuts and Bolts of Repression," *J. Cell. Physiol.* 213:384-390.
Mirsaidov et al. (2009) "Nanoelectromechanics of Methylated DNA in a Synthetic Nanopore," *Biophys. J. Lett.* 96(4):L32-L34.
Mirsaidov et al. (2010) "Slowing the Translocation of Double-Stranded DNA using a Nanopore Smaller that the Double Hlix," *Nanotechnology* 21:395501.
Mirsidov et al. (2010) "Molecular Diagnostics for Personal Medicine Using a Nanopore," *Advanced review* 2:367-381.
Mirsaidov (2008) "Optimal Optical Trap for Bacterial Viability," *Phys. Rev. E.* 78(2):021910.
Mirsaidov et al. (Oct. 2008) "Live Cell Lithography: Using Optical Tweezers to Create Synthetic Tissues," *Lab on a Chip* 8:2174-2181.

(56) References Cited

OTHER PUBLICATIONS

Mitra et al. (May 2003) "Digital Genotyping and Haplotyping with Polumerase Colonies," *Proc. Nat. Acad. Sci. USA* 100(10):5926-5931.
Morozova et al. (2008) "Applications of Next-Generation Sequencing Technologies in Functional Genomics," *Genomics* 92(5):255-264.
Muthukumar et al. (Dec. 2006) "Simulation of Polymer Translocation Through Protein Channels," *Proc. Nat. Acad. Sci. USA* 103(4):5273-5278.
Nair et al. (Jun. 2006) "Performance Limits of Nanobiosensors," *Appl. Phys. Lett.* 88:233120.
Nakamura et al. (1998) "Hypermethylation of the Metastasis-Associated S100A4 Gene Correlates with Gene Activation in Human Colon Adenocarcinoma Cell Lines," *Clin. Exp. Metastasis* 16(5):471-479.
Nakane et al. (2002) "Evaluation of Nanopores as Candidates for Electronic Analyte Detection," *Electrophoresis* 23(16):2592-2601.
Nakayama et al. (1998) "Hypomethylation Status of CpG Sites at the Promoter Region and Overexpression of the Human MDR1 Gene in Acute Myeloid Leukemias," *Blood* 92(11):4296-4307.
Nathan et al. (2002) "Bending and Flexibility of Methylated and Unmethylated EcoRI DNA," *J. Mol. Biol.* 316:7-17.
Nilsson et al. (2006) "Localized Functionalization of Single Nanopores," *Adv. Mater.* 18:427-431.
Noskov et al. (Oct. 2004) "Ion Permeation through the α-Hemolysin Channel: Theoretical Studies Based on Brownian Dynamics and Poisson-Nernst-Plank Electrodiffusion Theory," *Biophys. J.* 87:2299-2309.
Ohshiro et al. (Jan. 2006) "Complimentary Base-Pair-Facilitated Electron Tunneling for Electrically Pinpointing Complementary Nucleobases," *Proc. Nat. Acad. Sci.* 103(1):10-14.
Ohtanifujita et al. (1993) "CpG Methylation Inactivates the Promoter Activity of the Human Retinoblastoma Tumor-Suppressor Gene," *Oncogene* 8(4):1063-1067.
Ooi et al. (Jun. 2008) "The Colorful History of Active DNA Demethylation," *Cell* 133(7):1145-1148.
Ottow et al. (1998) "Determination of Flat-Band Potentials of Silicon Electrodes in HF by Means of AC Resistance Measurements," *J. Electroanalytical Chem.* 455:29-37.
Packer et al. (2002) "ParmGKB: The Pharmacogentics Knowledge Base," *Nuc. Acids Res.* 30(3):158-162.
Paegel et al. (2003) "Microfluidic Devices for DNA Sequencing: Sample Preparation and Electrophoretic Analysis," *Curr. Opin. Biotech.* 14:42-50.
Paez et al. (Jun. 2004) "EGFR Mutations in Lung Cancer: Correlation with Clinical response to Gefitinib Therapy," *Science* 304:1497-1500.
Panne et al. (1999) "The McrBC Endonuclease Translocates DNA in a Reaction Dependent on GTP Hydrolysis," *J. Mol. Biol.* 290(1):49-60.
Pearlman et al. (1990) "The Calculated Free Energy Effets of 5-Methyl Cytosine on the B to Z Transition in DNA," *Biopolymers* 29(8-9):1193-1209.
Phillips et al. (2005) "Scalable Molecular Dynamics with NAMD," *J. Comp. Chem.* 26:1781-1802.
Ramsahoye et al. (May 2000) "Non-CpG Methylation is Prevalent in Embryonic Stem Cells and May be Mediated by DNA Methyltransferase 3a," *Proc. Nat. Acad. Sci. USA* 97(10):5237-5242.
Rauch et al. (2003) "C5 Methylation of Cytosine in B-DNA Thermodynamically and Kinetically Stabilizes BI" *J. Am. Chem. Soc.* 125(49):14990-14991.
Rauch et al. (2005) "Towards an Understanding of DNA Recognition by the Methyl-CpG Binding Domain 1," *J. Biomol. Struct. Dyn.* 22(6):695-706.
Reu et al. (Mar. 2006) "Expression of RASSF1A, an Epigenetically Silenced Tumor Suppressor, Overcomes Resistance to Apoptosis Induction by Interferons," *Cancer Res.* 66(5):2785-2793.
Rivetti et al. (Mar. 1998) "Polymer Chain Statistics and Conformational Analysis of DNA Molecules with Bends or Sections of Difference Flexibility," *J. Mol. Biol.* 280:41-59.
Robertson, K.D. (May 2005) "DNA Methylation and Human Disease," *Nature Rev.* 6:597-610.
Robertson et al. (2007) "Single-Molecule Mass Spectrometry in Solution Using a Solitary Nanopore," *Proc. Nat. Acad. Sci. USA* 104(20):8207-8211.
Ronaghi, M. (2001) "Pyrosequencing Sheds Light on DNA Sequencing," *Genome Res.* 11:3-11.
Roux, B. (1995) "The Calculation of the Potential of Mean Force Using Computer Simulations," *Comp. Phys. Comm.* 91:275-282.
Rouzina et al. (Feb. 2001) "Force Induced Melting of DNA Double Helix 2. Effect of Solution Conditions" *Biophysical J.* 80:894-900.
Rouzina et al. (2001) "Force Induced Melting of the DNA Double Helix 1. Thermodynamic Anallysis," *Biophys. J.* 80:882-893.
Salisbury, M.W. (2003) "Fourteen Sequencing Innovations that Could Change the way you Work," *Genome Technol.* 35:40-47.
Sanger et al. (1977) "DNA Sequencing with Chine-Terminating Inhibitors," *Proc. Nat. Acad. Sci. USA* 74(12):5463-5467.
Sauer-Budge et al. (Jun. 2003) "Unzipping Kinetics of Double-Stranded DNA in a Nanopore," *Phys. Rev. Lett.* 90(23):238101.
Scofield, J.H. (Feb. 1994) "Frequency-Domain Description of a Lock-in Amplifier," *Am. J. Phys.* 62(2):129-133.
Scott et al. (2008) "3D Hydrodynamic Focusing in a Microfluidic Coulter Counter," *Rev. Sci. Instrum.* 79:046104.
Shaw et al. (2007) "Anton, A Special-Purpose Machine for Molecular Dynamics Simulation," International Symposium on Computer Architecture, ACM 1-12.
Shendure et al. (May 2004) "Advanced Sequencing Technologies: Methods and Goals," *Nat. Rev. Genet.* 5(5):335-344.
Sigalov et al. (Web Release Dec. 11, 2007) "Detection of DNA Sequences Using an Alternating Electric Fields in a Nanopore Capacitor," *Nano Lett.* 8(1):56-63 Plus Supporting Information.
Siwy et al. (Nov. 2002) "Fabrication of a Synthetic Nanopore Ion Pump," *Phys. Rev. Lett.* 89(19):198103.
Smeets et al. (Jan. 2008) "Noise in Solid-State Nanopores," *Proc. Nat. Acad. Sci.* 105(2):417-421.
Smeets et al. (2009) "Low-Frequency Noise in Solid-State Nanopores," *Nanotechnology* 20:095501.
Smeets et al. (2006) "Salt Dependence of Ion Transport and DNA Translocation Through Solid-State Nanopores," *Nano Lett.* 6(1):89-95.
Smet et al. (Jul. 1996) "The Activation of Human Gene MAGE-1 in Tumor Cells is Correlated with Genome-Wide Demethylation," *Proc. Nat. Acad. Sci. USA* 93(14):7149-7153.
Smith et al (Feb. 1996) "Overstretching B-DNA: The Elastic Response of Individual Double-Stranded and Single-Stranded DNA Molecules" *Science* 271:795-799.
Sonnefeld et al. (Jul. 2001) "Determination of Electric Double Layer Parameters for Spherical Silica Particles under Application of the Triple Layer Model using Surface Charge Density Data and Results of Electrokinetic Sonic Amplitude Measurements," *Colloid Surf. A-Physiochm. Eng. Asp.* 195:215-.
Stein et al. (2001) "Ion-Beam Sculpting at Nanometre Length Scales," *Nature* 412:166-169.
Stellwagon et al. (2003) "Probing the Electrostatic Shielding of DNA with Capillary Electrophoresis," *Biophysical J.* 84(3):1855-1866.
Stewart et al. (2000) "Methyl-Specific DNA Binding by McrBC, A Modification-Dependent Restriction Enzyme," *J. Mol. Biol.* 298:611-622.
Stoddarrt et al. (2009) "Single-Nucleotide Discrimination in Immobilized DNA Oligonucleotides with a Biological Nanopore," *Proc. Nat. Acad. Sci. USA* 106(19):7702-7707.
Storm et al. (Jul. 2003) "Fabrication of Solid-State Nanopores with Single-Nanometre Precision," *Nature Materials* 2(8):537-540.
Storm et al. (2005) "Fast DNA Translocation Through a Solid-State Nanopore," *Nano Lett.* 5(7):1193-1197.
Storm et al. (2005) "Translocation of Double-Strand DNA Through a Silicon Oxide Nanopore," *Phys Rev E.* 71: 051903-051910.
Suzuki et al. (Apr. 2004) "Epigenetic Inactivation of SFRP Genes Allows Constitutive WNT Signaling in Colorectal Cancer," *Nature Genet.* 36(4):417-422.

(56) References Cited

OTHER PUBLICATIONS

Tabard-Cossa et al. (Jun. 29, 2007) "Noise Analysis and reduction in Solid-State Nanopores," *Nanotech* 18:305505.

Takai et al. (Mar. 2002) "Comprehensive Analysis of CpG Islands in Human Chromosomes 21 and 22," *Proc. Nat. Acad. Sci. USA* 99(6):3740-3745.

Tardella et al. (Aug. 1985) "Highly Accumulated Electron Layer at a Semiconductor/Electrolyte Interface," *Phys. Rev. B*. 32(4):2439-2448.

Thorisson et al. (2005) "The International HapMap Project Web Site," *Genome Res*. 15:1592-1593.

Timp et al. (1999) "Nanoelectronics for Advanced Computation and Communications," In; *Nanotechnology* Timp, G. ed., Springer-Verlag, pp. 7-89.

Timp, G. (1998) "Progress Toward 10nm CMOS Devices," *Proc. IEDM* 98:615-618.

Timp et al. (2009) "Jamming Prokaryotic Cell-to-Cell Communications in a Model Biofilm," *Lab Chip* 9:925-934.

Timp et al. (May 2010) "Nanopore Sequencing: Electrical Measurements of the Code of Life," *IEEE Tran. Nanotechnol*. 9(3):281-294.

Van Dorp et al. (Mar. 2009) "Origin of the Electrophoretic Force on DNA in Solid-State Nanopores," *Nature Phys*. 5: 347-351.

Venter et al. (Feb. 2001) "The Sequence of Human Genome," *Science* 291:1304-1351.

Wang et al. (2006) "Fabrication of Patterns Sapphire Substrate by Wet Chemical Etching for Maskless Lateral Overgrowth of GaN," *J. Electrochem. Soc*. 153(3):C182-C185.

Wanunu et al. (2007) "Chemically Modified Solid-State Nanopores," *Nano Lett*. 7(6):1580-1585.

Weber et al. (Aug. 2005) "Chromosome-Wide and Promoter Specific Analyses Identify Sites of Differential DNA Methylation in Normal and Transformed Human Cells," *Nature Genetics* 37(8):853-862.

Weber et al. (Apr. 2007) "Distribution, Silencing Potential and Evolutionary Impact of Promoter DNA Methylation in the Human Genome," *Nature Genetics* 39(4):457-466.

William et al. (Apr. 2001) "Entropy and Heat Capacity of DNA Melting from Temperature Dependence of Single Molecule Stretching," *Biophys. J*. 80:1932-1939.

William et al. (Feb. 2001) "Effect of pH on the Overstretching Transition of Double-Stranded DNA: Evidence of Force-Induced DNA Melting," *Biophysical J* 80:874-881.

Wood et al. (Nov. 2007) "The Genomic Landscapes of Human Breast and Colorectal Cancers," *Science* 318:1108-1113.

Woodin, T. (2005) "Trends in Funding Science Education, 1994-2004," *Biochem. Mol. Biol. Ed*. 33(3):211-216.

Wu et al. (Dec. 2005) "Hypomethylation-Linked Activation of PAX2 Mediates Tamoxifen-Stimulated Endometrial Carcinogenesis," *Nature* 438(7070):981-987.

Xiong et al. (Apr. 1997) COBRA: A Sensitive and Quantitative DNA Methylation Assay *Nucleic Acids Res*. 25(12):2532-2534.

Yang et al. (Aug. 2005) "Determination of Protein-DNA Binding Constants and Specificities from Statistical Analyses of Single Molecules: MutS-DNA Interactions," *Nuc. Acids Res*. 33(13):4322-4344.

Yoder et al. (Aug. 1997) "Cytosine Methylation and the Ecology of Intragenomic Parasites," *TIG* 13(8):335-340.

Yuan et al. (2003) "Energy Landscape of Streptavidin Biotin Complexes Measured by Atomic Force Microscopy," *Biochemistry* 39(33):10219-10223.

Zhao et al. (2007) "Detecting SNPs Using a Synthetic Nanopore," *Nano Letters* 7(6):1680-1685.

Zhao et al. (Oct. 2008) "Stretching and Unzipping Nucleic Acid Hairpins Using a Synthetic Nanopore," *Nuc. Acids Res*. 36(5):1532-1541.

Zhumd et al. (1998) "Evaluation of Surface Ionization Parameters from AFM Data," *J. Colloid Interface Sci*. 207:332-343.

Applied Biosystems (2009) "The SOLiD 3 System: Enabling the Next Generation of Science," In; Applied Biosystems.

Notice of Allowance and reasons related thereto corresponding to U.S. Appl. No. 13/133,300, mailed Dec. 3, 2012—7 pages.

Office Action corresponding to U.S. Appl. No. 13/133,300, mailed Jun. 27, 2012.

Wang et al, BRCA1 promoter methylation predicts adverse ovarian cancer prognosis, 2006, Gynecologic Oncology, 101, 403-410.

\* cited by examiner

| (b) system | 0.1 M current (pA) | 0.1 M time (μs) | 1.4 M current (pA) | 1.4 M time (μs) |
| --- | --- | --- | --- | --- |
| T-A/A-T | 124 ± 2 | 2.71 | 646 ± 10 | 0.74 |
| C-G/G-C | 113 ± 2 | 3.94 | 618 ± 6 | 1.91 |
| T-A | 122 ± 3 | 1.35 | 650 ± 14 | 0.37 |
| A-T | 125 ± 3 | 1.35 | 643 ± 14 | 0.37 |
| C-G | 115 ± 3 | 1.82 | 621 ± 8 | 1.05 |
| G-C | 112 ± 3 | 2.12 | 615 ± 9 | 0.86 |
| none | 195 ± 5 | 0.72 | | |

Figure 8(d)

CHARACTERIZING STRETCHED POLYNUCLEOTIDES IN A SYNTHETIC NANOPASSAGE

STATEMENT REGARDING FEDERALLY SPONSORED RESEARCH OR DEVELOPMENT

This invention was made with United States government support under contract number R01 HG003713 awarded by the National Institute of Health and contract number PHY0822613 awarded by the National Science Foundation. The United States government has certain rights in the invention.

CROSS-REFERENCE TO RELATED APPLICATIONS

This application claims benefit of U.S. provisional patent application 61/287,974 filed Dec. 18, 2009 which is hereby incorporated by reference to the extent it is not inconsistent with the present disclosure.

BACKGROUND OF THE INVENTION

Provided are methods and devices for characterizing polynucleotides, such as determining nucleotide sequences in double stranded DNA.

DNA, the program for life, is encoded using four chemical bases called adenine (A), guanine (G), cytosine (C) and thymine (T), which are paired together in a complementary fashion (A to T and C to G) and ordered in a species-specific sequence. The aim of genomic science is to predict biological behavior using the information stored in the DNA sequence within each cell. But when the first draft sequence of the human genome emerged in early 2001,6 despite its enormous value to genetics, it quickly became apparent that our understanding of the relationship between the genetic code and cellular function was deficient. For example, only 5% of the human genome is conserved, and of that, only 30% lies within the exons of known protein-encoding genes.7 The rest lies in the so-called "dark matter" of the human genome—leading to efforts such as the ENCyclopedia Of DNA Elements (EN-CODE)8 that strive to identify regulatory components. Identifying genes and controlling regions, such as promoter sites turns out to be a major undertaking in itself.

To glean more information about how genetics informs cellular function, and therefore its affect on development and disease, it is essential that we learn to sequence rapidly and economically using a minute amount of material. The tasks can be categorized as follows. On one hand, in terms of de novo sequencing, not only are there many species with unsequenced genomes, but the human microbiome, the genome sequence of the many different species of bacteria living in or on humans, still remains a mystery. The microbiome of the flora of our gut alone is estimated to contain ~300 billion base-pairs (Gbp), or ~100× the human genome.9 On the other hand, the vast majority of the work ahead involves re-sequencing genomes with an already known base sequence. The first, obvious example is mutation sequencing where recent work has shown that the majority of human cancers do not always have mutations in the same locations, or even the same genes.10 Moreover, the mutations and genotype of the individual has been shown to be important for chemotherapeutic effectiveness: i.e. genomics can determine a drug's effectiveness on an individual.11

Sequencing can also provide clues to health and development beyond the actual genomic sequence itself. The proteins expressed by genes represent the machinery of the cell—they make things work. But an individual organism can express the same genes differently depending on the epigenetic profile. High-throughput sequencing aspires to determine this profile. For example, it can give information on DNA-binding protein interaction, using ChIP-seq to find the locations of occupied binding sites.12 With inexpensive, high-throughput sequencing, we will be able to determine the difference between these binding sites in different tissue and under different conditions. Moreover, using ChIP-seq we can also achieve single-base resolution of the genomic histone code, one of the epigenetic regulators of chromatin structure and gene expression.13 It can also be used to determine DNA methylation patterns, a reversible modification of cytosines (in mammals), which alters protein binding (see, e.g., U.S. Pat App. No. 61/139,056 hereby incorporated by ref.) Subsequent sequencing and alignment may be used to distinguish methylated from unmethylated cytosines, illuminating the methylation pattern.14 It may also be advantageous for gene expression studies to sequence the transcriptome; i.e. the sequence of the RNA extracted from cells or tissues. This can give detailed information about the levels of expression, the splicing variation, and even allow for the identification of new non-coding RNAs, which may be involved in the regulation and are parts of the "dark matter" of the genome.15

All of these "-omes" would be facilitated by technology that inexpensively and quickly determines sequence information from a genetic sample. For this reason, ultra-low cost sequencing technologies have been identified as a scientific priority and significant effort is being devoted to its study and development.

Since its development in 1977, the Sanger method of DNA sequencing has transformed biology—it is the standard to which all other methods of sequencing are compared. 16 The basis for Sanger sequencing is the polymerase chain reaction (PCR), which is used in combination with dideoxy-terminated nucleotides triphosphates to prematurely terminate the elongation reaction. The classical chain-termination method requires a DNA template, a DNA primer, a DNA polymerase, nucleotides and fluorescently labeled nucleotides that terminate DNA strand elongation. By mixing fluorescently labeled dideoxynucleotides with deoxynucleotides, the PCR reaction is prematurely terminated, leading to fragmentary single stranded copies of the template that differ in length with the last base fluorescently labeled with a different fluorescent moiety, depending on the base. Separating these fragments by size through electrophoresis, the sequence can be determined from the color of fluorescence produced at a given length.

Though functional, this procedure is problematic for several reasons. The template read length using this method is limited to ~800 bp. This introduces significant challenges, especially for de novo sequencing, requiring that either chromosome walking or shotgun sequencing be used, which are both time consuming and require re-assembly of the completed sequence. The chain termination reaction is also time consuming, as is electrophoretic separation, leading to the development of techniques for massively parallel methods for sequencing.17 But the overarching problems with Sanger sequencing method are the relatively large amounts of DNA required—amplification leads to errors—and the expense due to reagents for labeling and separation.

There are emerging technologies that have the potential to supersede conventional, Sanger sequencing and in some cases sequence the human genome for $1000 or less. Shendure et al have analyzed these technologies in detail.18 They can be loosely categorized as: bioMEMs, which is just an extension of conventional electrophoretic methods through miniaturization and integration; sequencing-by-hybridization, which uses the differential hybridization of oligonucleotide probes to decode the DNA sequence; massively parallel signature sequencing (MPSS), which is based on cycles of restriction digestion and ligation; and finally, non-enzymatic, real-time single-molecule sequencing.

BioMEMs has the advantage that it relies on the same tested principles as electrophoretic sequencing, which has already been used to sequence 10 11 nucleotides. Using variations of the Sanger process in conjunction with capillary array electrophoresis to separate deoxyribonucleotide triphosphate fragments, about 100 bp can be sequenced per minute at a cost of <$1 with an accuracy of about 99.99%, which is considered to be the gold standard, but it seems unlikely that a factor of 100,000× cost reduction will be achieved through scaling and integration alone. Hybridization sequencing has the advantage that the data collection method, i.e. scanning the florescence emitted by labeled DNA that has been hybridized to an array of probe sequences, is compatible with high-throughput, but probes have to be designed that avoid cross-hybridization to the wrong target. This renders 50% of the chromosome inaccessible. All methods like sequence-by-synthesis, cyclic-array sequencing on amplified molecules, and MPSS, which rely on some method of isolated clonal amplification are, first of all, costly and often problematic. For example, they may experience a low frequency of nucleotide misincorporation or non-incorporation, which manifests itself in signal decay through "dephasing". In contrast, cyclic-array sequencing on single molecules eliminates the costly PCR-amplification step, requires less starting material with no risk of de-phasing, but achieving the signal-to-noise required for single molecule detection is still a challenge.

According to Mardis,19 right now the Roche GS-FLX (454) sequencer uses emulsion PCR to produce 100 Mb of data in 7 h with a 250 bp read length (per bead) at a cost of $8439 or $84.40 per Mb. In contrast, a run in an Applied Biosystems SOLiD (sequencing by oligo ligation) sequencer requires 5 days and produces 3-4 Gb of sequence data with an average read length of 25-35 bp, costing $5.81 per Mb. Applied Biosystems estimates that their SOLiD sequencer will be able to sequence an entire human genome for only $10,000 in just 2 weeks. Following Shendure's analysis, 18 for re-sequencing, the error rate has to be less than the expected variation in the sequence. Since human chromosomes differ at approximately 1 in every 1000 bp, an error rate of 1/100 kbp would be needed to ensure confidence. If the accuracy of a raw read is 99.7% (current state-of-the-art), then ×3 coverage of each base will yield this error rate. To ensure a minimum ×3 cover of >95% of the diploid human genome, ×6.5 coverage, or about 40 billion raw bases at a cost per base of <$10000, or 4 million bases per $1. If an improvement over SOLiD performance is derived simply from an increase in the acquisition rate per device, we would therefore need to sequence at a rate of ~330,000 bp/s to reach a $1,000 genome. No assembly is required in re-sequencing a genome; the read needs only be long enough to allow it to be matched to a unique location in an assembled reference genome, and how it differs from the reference. In the mammalian genome only ~73% of 20-bp genomic reads SOLID uses can be assigned to a single unique location. Achieving >95% uniqueness will require reads >60 bp. Thus, a re-sequencing instrument that can deliver a $1,000 human genome with reasonable coverage and accuracy will need to achieve >60 bp reads with 99.7% raw-base accuracy, acquiring data at a rate of 330,000 bp/s or 1 bp/3 µs. A faster instrument with longer reads will be cheaper still.

Single molecule DNA sequencing represents the logical end-of-the-line in development of sequencing technology, which extracts the maximum amount of information from a minimum of material and pre-processing. When paired with a high-throughput and low cost instrument, it would change the genomic flow of data from a trickle to a deluge. Specifically, the low material requirement coupled with quick results would allow for easy sequencing of precious primary samples from human patients, e.g. allowing doctors to sequence a biopsy from a tumor to determine the best chemotherapy. Moreover, it would represent a leap forward in determining the epigenome, the non-genetic marks on DNA which affect gene expression.

SUMMARY OF THE INVENTION

Provided are methods, devices, and methods for making devices capable of sequencing DNA via confined electric field control across a nanopassage in a membrane, such as a nanopore, through which a polynucleotide is forced to traverse. Sequencing a single molecule of DNA with a nanopore is a revolutionary change in sequencing technology because it combines the potential for long read lengths (>5 kbp) with high speed (1 bp/10 ns), while obviating the need for costly procedures like PCR amplification or sample preparation due to the exquisite single molecule sensitivity. Moreover, electrical detection of DNA using a nanopassage could have several advantages over cyclic arrays or fluorescent microscopy. Usually single molecule sequencing relies on enzymatic incorporation of a fluorescently labeled mononucleotide through a polymerase and applying techniques that suppress the ambient radiation so that one molecule can be identified. In contrast, the nanopassage sequencing concept uses a radically new approach to detection that is reminiscent of Coulter's original idea of using objects within a constricted current path to alter, the electrical resistance.

Nanopore sequencing relies on the electric signal that develops when DNA translocates through a pore in a membrane. DNA is a highly charged polyanion. By applying an electric field to a nanometer-diameter pore in a thin membrane, individual DNA molecules are forced to move through the pore in a single-file sequential order, as if threading a needle. Because of unique composition of each base-type, each base has a characteristic electrical signature. Assessing the electrical signature over time as a single polynucleotide traverses a pore having a confined electric field provides a means for analyzing nucleotide sequence. In this manner, a pore can by used to analyze the sequence by reporting all of the signatures in a single read without resorting to multiple copies of DNA.

The methods provided herein provide the capability to reliably sequence a polynucleotide by a unique trapping method to ensure there is a sufficient residence time, on a base-by-base basis, as a polynucleotide traverses a nanopassage. The combination of a time-controlled electric field across a nanopassage having a well-defined geometry, results in a functional equivalent of a harmonic trap. The nanopassage is designed to provide at least a portion of the passage, such as a confine region, with a dimension sufficiently small such that the polynucleotide cannot traverse and transit without undergoing a deformation. In particular, when a nucleotide base or nucleotide base pair is forced into the confine region by an applied electric field that deforms the polynucleotide, lowering the electric field means the portion of polynucleotide within the confine region cannot exit the confine region, and is trapped. This trap means that electric measurements may be reliably made, effectively for as long as desired, to provide high-fidelity measurement on a specific region, including a specific base, of a DNA molecule. The electric field is switched to a sufficiently high magnitude to permit the trapped portion to deform and exit the confine region, and when the next base or base pair is in the confine region, the electric field is lowered to again trap the polynucleotide, but at a different axial position.

In an aspect, provided are methods of trapping a polynucleotide or sequencing a polynucleotide in a nanomembrane nanopassage. In an aspect, any of the methods provided herein related to a polynucleotide that is double stranded, such as double stranded DNA.

In an embodiment, provided is a method of characterizing at least a portion of a double-stranded polynucleotide by providing a membrane having a nanopassage that defines a confine region. The membrane separates a first fluid compartment from a second fluid compartment, and the nanopassage is in fluid communication with the first and second compartments. A polynucleotide is provided to the first fluid compartment. A driving voltage bias that is greater than a threshold voltage is established across the membrane to force a portion of the polynucleotide sequence into the nanopassage, wherein the polynucleotide portion has a confined portion positioned within the confine region and the confine region deforms the double-stranded polynucleotide structure by increasing axial rise from an undeformed axial rise value to a deformed axial rise value in the confine region or a region adjacent thereto. Electrical current is monitored through the nanopassage and a confine state identified from the monitored electrical current, wherein the confine state corresponds to the confined portion containing a confined nucleotide base-pair of the polynucleotide in the confine region. The driving voltage bias is reduced to a holding voltage that is less than or equal to the threshold voltage and that is greater than or equal to zero, thereby trapping the confined nucleotide base-pair in the nanopassage confine region for a trapping time. During the trapping, a nucleotide base-pair dependent current blockade is measured through the nanopassage confine region having the confined nucleotide base-pair, to characterize the confined nucleotide base-pair, thereby characterizing at least a portion of the polynucleotide.

In an embodiment, the method further comprises establishing a translocation voltage bias that is greater than the threshold voltage to force the confined nucleotide base-pair out of the confine region in a direction that is toward the second compartment. The monitoring, identifying, reducing and measuring steps are repeated to thereby characterize a confined nucleotide base-pair that is at a position upstream from the previously characterized confined nucleotide. For example, the characterized confined nucleotides base-pair can be nucleotide base-pairs adjacent to each other in said polynucleotide. In this manner, the characterization may be continuous polynucleotide base-pair or base sequencing. In an aspect, the method relates to characterizing a contiguous portion of the polynucleotide, wherein the contiguous portion corresponds to at least 10% of the entire length of the polynucleotide. In another aspect, the contiguous portion corresponds to the entire length of the polynucleotide, or at least 90%, 95% or 99% of the entire length. In an aspect, the entire length of the polynucleotide is sequenced.

In an embodiment, the method relates to a polynucleotide that translocates unidirectionally from the first compartment to the second compartment.

In another aspect, the method further comprises determining the threshold voltage for the nanopassage and the polynucleotide. The threshold determination may be empirical, such as by monitoring electric current through the nanopassage under different electric field conditions to identify when the polynucleotide is capable of translocating and when the polynucleotide is reliably trapped over a desired trapping time, as described herein.

In an aspect, the characterization is one or more of identifying a nucleotide-type, a nucleotide base-pair type or nucleotide methylation state. In an aspect the nucleotide is a naturally-occurring nucleotide. The method, however, is compatible for any type of nucleotide, so long as the nucleotide provides an electrically-detectable signal that is distinct from other nucleotides sought to be differentiated.

In an aspect, the characterization is methylation content, methylation pattern, or methylation content and pattern, such as further described in 61/139,056. In another aspect, the characterization is determining at least a portion of the polynucleotide sequence.

The method is optionally further described in terms of a deformed axial rise value, such as a value that is at least 20% greater than the undeformed axial rise value. In an aspect, the undeformed axial rise is about 0.34 nm per base-pair or less, corresponding to the double helix of double stranded DNA so that the deformed axial rise is about 0.4 nm or greater. In an aspect, the deformed axial rise value is selected from a range that is greater than or equal to 0.34 nm and less than or equal to 0.7 nm. In general, the axial rise is sufficiently small such that there is not physical permanent damage to the polynucleotide.

In another embodiment, the characterization comprises determining the sequence of at least 2000 contiguous bases. The methods and systems provided herein are compatible with sequencing a wide range of polynucleotide lengths, including lengths that are less than 2000 bases, such as by manipulating membrane capacitance. For example, capacitance values ranging from about 10 to 400 pF are used in various embodiments. In general, the larger the capacitance the slower the electrical response in the system, as characterized from the associated time constant for the system (e.g., the product of the electrolyte resistance and membrane capacitance) compared to the translocation time (e.g., product of the polynucleotide length and translocation velocity). Contemplated herein is miniaturization to significantly reduce membrane capacitance, thereby decreasing the minimum detectable strand length. For example, the time constant may be reduced substantially (such as to values less than 1 ns), such as by the use of composite membranes made of $Si_3N_4$ and polyimide.

In an aspect, the invention is further described in terms of the nanopassage. For example, a nanopassage having a confine region with a maximum cross-sectional area that is less than or equal to the cross-sectional area of hydrated double stranded DNA. In an aspect the maximum cross-sectional is defined by two axes, which are both comparable to or less than 2.9 nm in length, since the hydrated diameter of double-stranded DNA ranges from 2.6 to 2.9 nm. Thus, the maximum cross-sectional area is 8.41 $nm^2$. A nanopassage may also have a confined region with a minimum cross-sectional area that is greater than or equal 1.6×1.6 $nm^2$. For an area less than this the double-stranded DNA molecule will denature and translocate through the pore one strand at a time. (40).

In an aspect the nanopassage is a pore having a diameter that is less than or equal to the effective diameter of a hydrated DNA double helix. In an aspect, the nanopassage is a tapered nanopore having a maximum diameter that is less than or equal to 2.9 nm and a minimum diameter centered in said confine region that is selected from a range that is greater than or equal to 1.6 nm and less than or equal to 2.9 nm. In an aspect, the taper relates to a maximum diameter at a membrane surface and a minimum diameter in the central portion of the membrane. In an aspect, the minimum dimension is at the midpoint between the top and bottom surfaces of the membrane and the taper is linear and can be described by a taper angle. In an aspect, the taper angle is selected from a range that is greater than or equal to 10° and less than or equal to 30°. In an aspect, the membrane has a thickness that is greater than or equal to 5 nm and less than or equal to 100 nm.

In an embodiment, the process relates to trapping the polynucleotide at a desired base-pair for a trapping time. In an aspect, the trapping time is selected from a range that is greater than or equal to 10 ns and less than or equal to 60 second. In an aspect, the trapping time is for a sufficiently long time to provide a high-fidelity read of the current blockade through the nanopassage for the confined base-pair. Accordingly, in an aspect, the holding voltage is applied for a holding time sufficient to provide high-fidelity assessment of said confined nucleotide base-pair. "High fidelity" refers to a measurement related to a specific base or base-pair that is sufficiently reliable that it is capable of being statistically distinguished from a measurement related to a different specific base or base-pair. For example, for measurements that are noisy, prolonging the measurement time may provide a more reliable average value and reduce the associated standard deviation, thereby providing a measurement of sufficient fidelity, e.g., high fidelity, to provide a statistically significant difference with a measurement obtained for a different base or base-pair. "High fidelity" also refers to the ability to correctly identify the base or base-pair more than 95% of the time, such as by providing a p-value of 0.05 at the 95% confidence level.

In an aspect, the translocation voltage is less than the driving voltage bias.

In an aspect, the polynucleotide travels in a direction from the first compartment to the second compartment at a translocation velocity that is greater than or equal to 1 nucleotide per 10 nanoseconds or greater than or equal to 1 nucleotide base pair per 10 nanoseconds.

In an embodiment, any of the methods provided herein further relate to diagnosing a medical condition for a patient from whom the polynucleotide is obtained, such as a medical condition that relates to a specific polynucleotide sequence or to methylation parameter/profile.

In an embodiment, the invention relates to one or more characteristics of the translocation voltage bias. In an aspect, the translocation voltage bias is a voltage pulse having a duration that is less than or equal to 1 µs. In an aspect the magnitude of the translocation voltage bias is at least two times greater than said holding voltage.

In an aspect, the membrane is a $Si_3N_4$ membrane, such as SiN membrane having a thickness selected from a range that is greater than or equal to 5 nm and less than or equal to 30 nm.

In another embodiment the invention is a method of trapping a portion of a double-stranded polynucleotide in a membrane nanopassage by providing a membrane having a nanopassage that defines a confine region, wherein the membrane separates a first fluid compartment from a second fluid compartment, and the nanopassage is in fluid communication with the first and second compartments. A polynucleotide is provided to the first fluid compartment and a threshold voltage for the membrane and the polynucleotide is determined. A driving voltage bias is established across the membrane that is greater than the threshold voltage, to force a portion of said polynucleotide sequence into the nanopassage confine region, wherein the nucleotide portion in the confine region is deformed and the confine region deforms the double-stranded polynucleotide structure by increasing axial rise from an undeformed axial rise value to a deformed axial rise value in said confine region or a region adjacent thereto. The driving voltage bias is decreased to a holding voltage bias, wherein the holding voltage bias is less than the threshold voltage, thereby trapping the polynucleotide portion in the nanopassage confine region for a trapping time, wherein at least one nucleotide base-pair is fixably positioned in the nanopassage confine volume.

In an aspect the threshold voltage is determined empirically. In an aspect the threshold voltage is determined by referring to a specification supplied by the manufacturer, such as depending on specific membrane composition and configuration, nanopassage size or geometry, DNA characteristic (e.g., length), electrolyte composition, electrode geometry, etc.

In an aspect, the method further comprises measuring a blockade current through the nanopassage having at least one nucleotide base-pair positioned in the confine volume and sequentially forcing the polynucleotide through the confine volume nucleotide base-pair by nucleotide base-pair by switching an electric field from a translocation voltage bias that is greater than the threshold voltage to the holding voltage bias at a switching frequency. In this manner, the holding voltage bias is applied when a nucleotide base-pair is positioned in the confine region, and the sequentially forcing step provides a nucleotide base-pair stepwise movement of the polynucleotide through the confine region in a direction from the first compartment to the second compartment so that every nucleotide base-pair within a contiguous length of the polynucleotide is trapped in the confine region and the blockade current is measured for each trapped nucleotide base-pair.

In an aspect, the holding voltage is applied for a holding time that is sufficient to provide high-fidelity measurement of the blockade current for the nucleotide base-pair positioned in the confine volume. In an aspect, the holding voltage bias corresponds to no voltage difference across the membrane. Alternatively, the holding voltage is an AC voltage. Alternatively, the holding voltage is a small positive or a small negative bias.

In an embodiment, the nanopassage confine region that traps the portion of polynucleotide has a maximum cross-sectional area that is 8.41 $nm^2$ and a minimum cross-sectional area of 2.56 $nm^2$. In an aspect, the polynucleotide is DNA, such as double stranded DNA forming a double helix, having a length, such as a length that is greater than or equal to 200 base pairs or shorter lengths.

In an embodiment, six or fewer base pairs are trapped in the nanopassage interior volume, or in the confine region.

In an aspect, the nanopassage is a pore having a minimum diameter that is smaller than an average diameter of said polynucleotide that is trapped. In an aspect, the nanopassage is a tapered pore having a maximum diameter at one surface and a minimum diameter positioned between the two membrane surfaces or at the opposite surface of the membrane. In an aspect, the taper is from each membrane surface and meet in between the surfaces, or at about the middle between the two surfaces.

In an aspect, the method relates to measuring an electrical blockade current across the nanopassage for said trapped portion.

In another embodiment, the invention is a method of sequencing a double-stranded polynucleotide. In an aspect, a membrane is provided having a nanopassage that defines a confine region having a minimum dimension that is less than an average axial diameter of the hydrated double-stranded polynucleotide, wherein the membrane separates a first fluid compartment from a second fluid compartment, and the nanopassage is in fluid communication with the first and second compartments. A polynucleotide is provided to the first fluid compartment. A driving voltage bias that is greater than a threshold voltage is established across the membrane to force a portion of the polynucleotide sequence into the nanopassage, wherein the polynucleotide portion has a confined portion positioned within the confine region. An electrical current through the nanopassage is monitored and the confined portion is identified as a confined nucleotide base-pair from the monitored electrical current. The driving voltage bias is reduced to a holding voltage that is less than or equal to the threshold voltage and that is greater than or equal to zero, thereby trapping the confined nucleotide base-pair in the nanopassage confine region for a trapping time. A nucleotide-dependent current blockade is measured through the nanopassage confine region having the confined nucleotide base-pair, to identify the confined nucleotide base-pair, thereby characterizing at least a portion of the polynucleotide. A translocation voltage bias is established that is greater than the threshold voltage to translocate the polynucleotide in a direction that is toward the second compartment, wherein the translocation moves the polynucleotide by one base-pair through the confine region. The monitoring, identifying, reducing and measuring steps are sequentially repeated to thereby identify a confined nucleotide base-pair that is at a single base-pair sequential position difference from the previously characterized confined nucleotide base-pair.

In an aspect, any of the methods provided herein relates to repeating the measuring step over the entire polynucleotide length, thereby sequencing the entire polynucleotide. In an aspect, any of the methods provided herein relates to uniquely identifying one nucleotide of the confined nucleotide base-pair with one strand of said double stranded polynucleotide, such as assigning a base to either the 5' or 3' strand.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

DETAILED DESCRIPTION OF THE INVENTION

Figure 1:
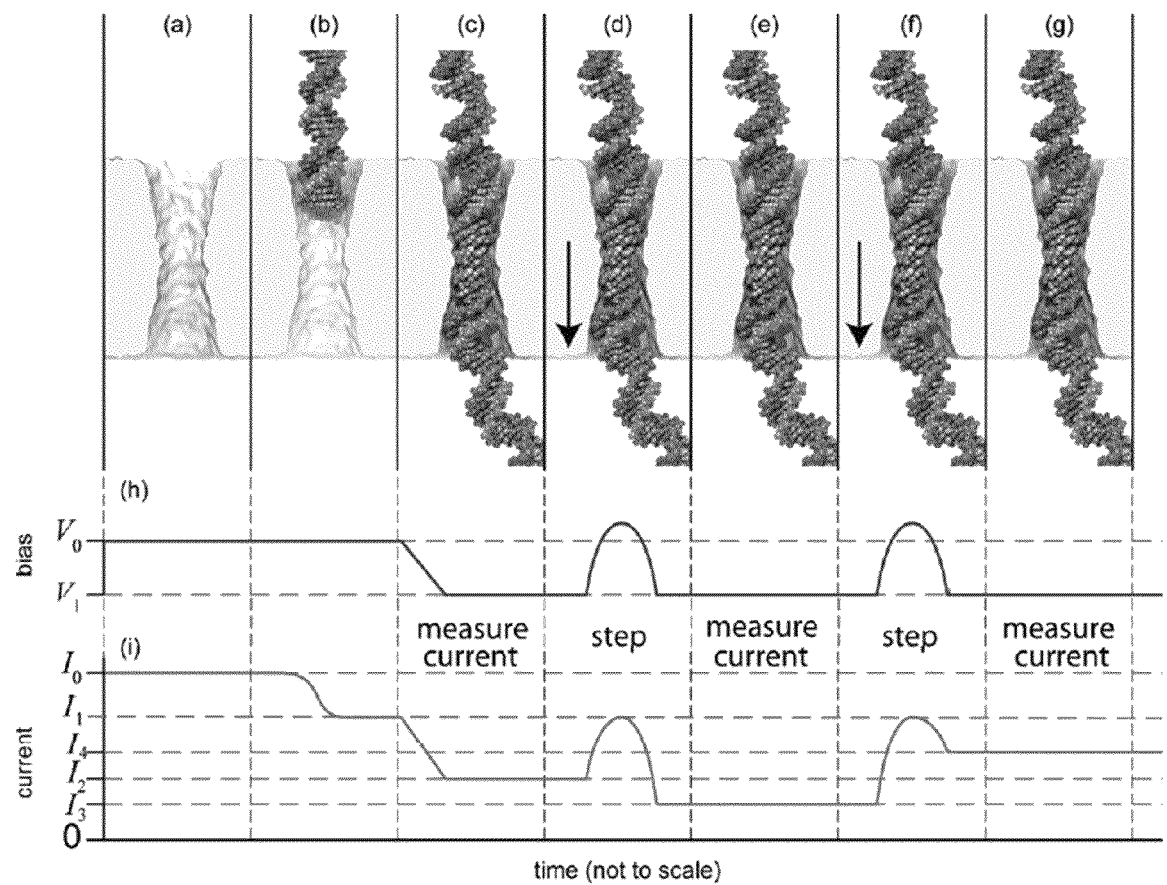
FIG. 1: Sequencing dsDNA with a solid-state nanopore showing a sequence of polynucleotide interactions (a)-(g) with a nanopore and corresponding applied voltage (h) and detected current (i) through the nanopore. (a) The driving bias of $V_0$, such as $V_0 > V_{threshold}(V_T)$ causes a flow of ionic current, $I_0$ through the pore. (b) Eventually, the driving bias forces a molecule of DNA into the pore opening, the molecule stretches and threads the pore (c). Consequently, the ionic current through the pore is at least partially blocked. The molecule is trapped by lowering the driving voltage to $V_1 < V_T$. (d) Using a series of voltage pulses, the DNA advances through the pore. The current is modulated distinctly by each base-pair (see FIG. 8). (e) The blockade current is measured using low noise, phase-sensitive lock-in techniques. (f-g) shows repeating of the cycle. (h) Diagram of the bias to the membrane by the Ag/AgCl electrodes immersed in the solution during each step in the process. (i) Diagram of the ionic pore current. Bottom panel is a schematic of one embodiment of a nanopassage and corresponding confine region, with respect to double stranded DNA.
Figure 1:
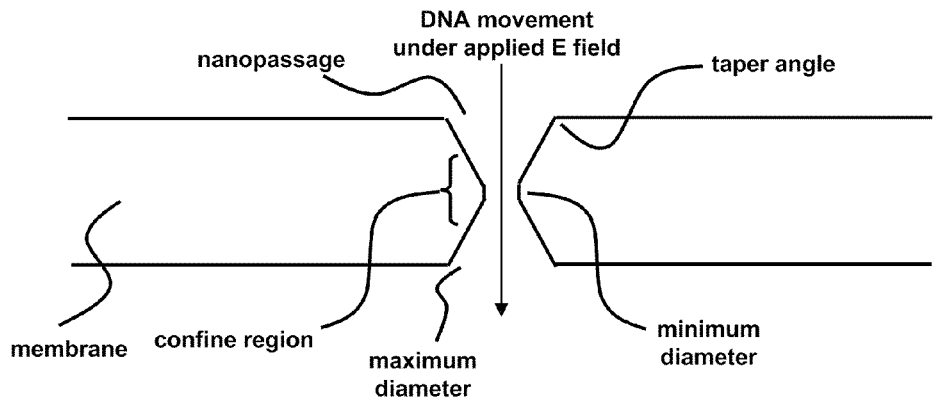

As used herein, "double stranded" refers to two complementary polynucleotide strands having base pair bonding in a double helix confirmation, such as for double stranded DNA in a double-helical confirmation.

"Confine region" refers to that portion of the nanopassage wherein the double-stranded polynucleotide must deform to enter, traverse and/or exit. In the examples provided herein, the deformation is achieved by applying an electric field across the nanopassage such that the polynucleotide, which is charged, experiences a force sufficient to deform or stretch thereby permitting entry, traverse and/or exit through the confine region and, therefore, traverse the nanopassage. When the force on the polynucleotide is removed, such as by lowering or removing the applied electric field, the polynucleotide cannot enter, traverse and/or exit the confine region. In an aspect only a portion of the nanopassage is a confine region, such as a portion that is centrally located with respect to the membrane surfaces. In another aspect, substantially all or all of the nanopassage is the confine region.

Accordingly, "driving voltage" refers to the voltage applied across the nanopassage required to initially force the polynucleotide into the nanopassage, and specifically into the confine region of the nanopassage. "Threshold voltage" refers to the voltage across the nanopassage required, once the polynucleotide has entered the confine region, for the polynucleotide to unidirectionally traverse through the confine region and out of the nanopassage. "Holding voltage" refers to a voltage that is sufficiently low that the portion of the polynucleotide in the confine region is unable to exit the confine region. In this manner, the holding voltage is less than the threshold voltage and the driving voltage. In an aspect, the threshold voltage is less than the driving voltage, such that polynucleotide controllably traverses the nanopassage and confine region in a manner that is electrically measurable. Generally the holding voltage is greater than zero (e.g., the polarity of the electric field is not reversed). However, so long as the confined portion of the polynucleotide cannot move in the opposite direction, the holding voltage can, if desired, be less than zero (e.g., reversed polarity).

"Fluid communication" refers to a nanopassage that permits flow of electrolyte, and specifically ions in the electrolyte from one side of the membrane (e.g., first fluid compartment) to the other side of the membrane (e.g., second fluid compartment), or vice versa.

"Deforms" refers to the membrane nanopassage having a geometry that makes it not possible for the polynucleotide to traverse or move in a direction from one fluid compartment to the other without the polynucleotide changing conformation. In particular, with respect to the double helix geometry, it is necessary for the axial rise between adjacent base pairs to increase before that portion of the polynucleotide can enter the confine region. This increase in axial rise is achieved by applying an electric field across the nanopassage such that polynucleotide. This change in axial rise is also referred to as stretch.

"Confine state" refers to whether a nucleotide or nucleotide base pair is uniquely positioned in the confine region or whether a nucleotide or nucleotide base pair is not uniquely positioned in the confine region, such as a base pair that is moving out of the confine region.

"Current blockade" refers to the measured current, at the holding voltage when there is a nucleotide base or nucleotide base pair trapped in the confine region. The magnitude of the current blockade depends on the type of base or base pair in the confine region including base identity and base methylation state. For embodiments where there is more than one base or more than one base pair in the confine region, the plurality of bases in the confine region will affect the current blockade and sequential measurements of current blockade as the polynucleotide traverses the confine region may be used to uniquely identify bases and base pairs.

The methods provided herein are capable of characterizing double stranded DNA such as by evaluating the percentages of base type, providing sequence determination over a select length of the polynucleotide, or sequencing entire lengths. In addition, characterizing may refer to assessing a methylation parameter, state and/or pattern.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

Example 1

Synthetic Nanopore for Sequencing Double-Stranded DNA

Sequencing a single molecule of DNA extracts the maximum amount of information from a minimum of material and pre-processing. When paired with a high-throughput and low cost sequencing instrument, it could change the flow of genomic data from a trickle to a deluge—thrusting genomics within the grasp of personalized medicine. Provided in this example is a nanopore instrument that sequences the genome in a cost effective manner, currently for less than $1000. Nanopore sequencing relies on the electric signal that develops when a single, polyanionic DNA molecule is forced by an electric field to translocate through a pore. The nanopore sequencing concept is revolutionary because it combines the potential for long read lengths (>5 kbp) with high speed (1 bp/10 ns), while obviating the need for costly and error-prone procedures like PCR amplification due to the exquisite single molecule sensitivity. However, high fidelity reads demand stringent control over both the molecular configuration in the pore and the translocation kinetics. The molecular configuration determines how the ions passing through the pore come into contact with the nucleotides, while the translocation kinetics affect the time interval in which the same nucleotides are held in the constriction as the data is acquired. Until now, no nanopore prototype proffered for sequencing has shown any prospect of satisfying both of these specifications at the same time.

A solid-state pore with a diameter (d) smaller than the effective diameter of the polynucleotide, e.g., the double helix, is used to sequence double-stranded DNA (dsDNA). We have shown that there exists a voltage threshold for dsDNA permeation through pores d<3 nm, consistent with the notion that the molecule must be stretched by the applied electric field to translocate through the pore.[2-4] We show here that if the voltage is rapidly switched from a value above the stretching threshold to zero during a translocation, dsDNA can be held in a pore indefinitely with a base-pair (bp) trapped in the constriction, for sufficiently small pore diameters (i.e.

d<2 nm for double stranded DNA). Our recent experiments with d~2.5 nm pores indicate that we can weakly trap λ-DNA for as long as 56 s, which is about 59,000× longer than the duration of a typical translocation (900 μs) observed for voltages above the stretching threshold.[5] Moreover, stretching dsDNA causes the bps to tilt as they translocate through the pore, which in turn modulates the electrolytic current. Accordingly, we measure a sequence-dependent blockade signal when the molecule is trapped, to discriminate A-T from C-G bps. One concern with sequencing dsDNA in this manner relates to determining which nucleotide is on which strand, e.g. distinguishing A-T from T-A. However, our molecular dynamics (MD) simulations show that the orientation of the by tilt caused by the confinement is maintained during translocation with the nucleotides on one strand always lagging their complement on the other. This combined with a nanometer-scale slit geometry for the pore that forces the current near the nucleotides indicates that a unique sequence of dsDNA can be characterized by first trapping the molecule and then using lock-in measurements of the blockade current to read bps with 3 pA precision.

Using this strategy to sequence a genome involves satisfying two requirements: 1. the ability to capture and trap a long dsDNA molecule in a d~2.0 nm pore; and 2. a nanopore with signal-to-noise performance commensurate with 3 pA current resolution. Corresponding to these requirements, this example specifically focuses on two items:

1. Determining conditions for trapping a long (>5 kbp) dsDNA molecule in a nanopassage, such as a 2.0×1.0 nm nano-slit. A long read length is a primary advantage associated with nanopore sequencing, but our experience shows that it is difficult to capture DNA >5 kb in <2.5 nm diameter pores. On the other hand, we observe that short DNA strands (<100 bp) can be forced to translocate through the pore at a high rate. Long DNA strands are forced away from the high field region in the constriction by the electro-osmotic flow through the pore. Thus, the capture rate is adversely affected by the large radius of gyration, which depends on the DNA persistence and contour lengths, and the pore surface charge, and the large voltage required to stretch dsDNA. We fabricate and test nanometer-scale 2.0×1 nm slits in ultra-thin (~10 nm) silicon nitride membranes, formed by electron-beam ablation in an electron microscope with a probe corrector to improve the brightness of the smaller diameter electron beams. Then, using pH to soften the DNA along with chemical surface treatments and atomic layer deposition to modify the pore charge, we further analyze conditions for trapping dsDNA, informed by quantum/molecular mechanics (QM/MM) simulations.

2. We also produce a low noise, high sensitivity instrument having a nanopassage suitable for sequencing dsDNA. To satisfy the electric field specification for stretching, the signal-to-noise required for single by discrimination, and the high-speed requirement for stepping between bps in a trap, we can fabricate nano-slits ranging from 2.5×1 nm to 1.6×0.7 nm in ultra-thin (~10 nm) nitride membranes, using MD in combination with Brownian dynamics to discover a pore geometry that maximizes the blockade signal. To mitigate the noise we can minimize the parasitic membrane capacitance associated with the substrate by using 1 μm×1 μm nitride membranes 10 nm thick fabricated on a sapphire substrate. Together these efforts should produce a nano-slit instrument with a bandwidth >330 kHz and rms-noise specification <0.4 pA suitable for reading a bp, that can step at high speed from one by to the next for re-sequencing a genome for less than $1000.

To sequence DNA using a nanopore, one must first find a robust, nanoporous structure of an appropriate size—comparable to or even less than the size of DNA to maximize the signal. The prospects for low cost, high-throughput nanopore sequencing are currently being explored using as prototypes either α-hemolysin (α-HL) and its mutants, or nanopores in solid-state membranes. Since the translocation velocity through the pore can be very high—about 1 bp/10 μs for α-HL and ~1 bp/10 ns for a solid-state pore—a single DNA molecule may be sequenced quickly and inexpensively, so long as the bases are discriminated electrically. Single base resolution on a translocating strand has not been demonstrated in the art. High fidelity reads demand stringent control over both the molecular configuration in the pore and the translocation kinetics. Control of the molecule configuration determines how the ions passing through the pore come into contact with the nucleotides in the constriction, while the translocation kinetics affect the time interval in which the same nucleotides are held in the constriction and data is acquired. Until now, none of the nanopore prototypes proffered for sequencing have shown any prospect of simultaneously satisfying both of these specifications.

Kasianowicz et al were among the first to adopt α-HL nanopores to detect and sort single DNA molecules.20,21 α-HL is a mushroom shaped heptamer that assembles across a phospholipid membrane. It is composed of seven identical subunits arranged around a central axis; the transmembrane portion is a β-barrel about 5 nm long with a minimum diameter of 1.5 nm. By placing this protein within a lipid membrane, an electric field induced flow of ions through the protein can be measured. If ssDNA or RNA is added to the anodic side, the translocation through the α-HL pore and resulting current blockade can be detected. The correspondence between current blockades and translocation of DNA between compartments was demonstrated by quantifying the DNA in the cathodic compartment using competitive PCR.20

There are limitations to using α-HL for sequencing, however. First are the obvious structural limitations—the protein structure is difficult to change in a predictable way. Though it is possible to introduce subtle mutations into the protein, gross structural changes are inordinately difficult. Chief among these structural limitations in α-HL are the length of the nanopore, and hence the thickness of the membrane, and the diameter of the pore. For example, the α-HL channel is only 1.5 nm in diameter—it will not admit dsDNA. The shape and length of the nanopore also means that it is functionally impossible to measure only one base at a time, making the sequence, which lies within the pore nontrivial to interpret, as multiple nucleotides are contributing to the signal. Finally, the lipid bilayer presents another limitation. The lipid bilayer membrane, which is usually suspended over a Teflon orifice, is typically 25-100 μm in diameter and only 5 nm thick. It ruptures after a few hours of use or after cycling the electrolyte a few times and the large size of the membrane produces a capacitance that adversely affects the frequency and noise performance.

Bayley et al.22 recently engineered α-HL in such a way to improve the signal to noise ratio, i.e. to hold a nucleotide in place for a longer period of time, in order to perform more averaging. By modifying the α-HL such that a cyclodextrin is placed in the β-barrel, the time that the pore is occluded by a single nucleotide can be extended. This allows more accurate measurements (>90%) of what nucleotide is in the pore based on blockade current. This method was used in combination with an exonuclease to determine the composition of ssDNA using an exonuclease to cleave off individual dNMPs, and then measure them as they are captured by the α-HL nanopore. This could potentially be used on raw, genomic dsDNA, and is even sensitive to base modifications such as cytosine methylation. However, it suffers from a crippling problem of logistics: i.e. how to transport the cleaved nucleotides from the exonuclease to the pore, ensuring that they arrive in the same sequence as found in the original DNA strand, that none escape (missing a base), and that the exonuclease does not outpace the pore. Tethering the exonuclease to the nanopore has been proffered as a solution, but this scheme is a nontrivial extension to the original nanopore sequencing concept.

We use a solid-state pore with a diameter smaller than the double helix to sequence a dsDNA. In contrast to α-HL, the size and shape of the pore in a solid-state membrane can be controlled on a sub-nanometer scale, allowing for a specific geometry to be tailored to the purpose. Solid-state pores also offer vastly improved stability: they are resilient in much harsher chemical and thermal environments useful for denaturing the DNA, as well as allowing for easier integration with other electrical or microfluidic components. Through microfabrication techniques, the solid-state membrane can be reduced to sub-micrometer scales, in principle, mitigating parasitic capacitance effects and improving electrical performance. There are several different methods available to create nanopores in thin membranes, such as ion-beam milling,[23] ion-track etching,[24] silicon dioxide reflow[25] or electron-beam ablation.[26] These techniques may be used on a variety of different membrane materials—allowing for different chemical properties, such as surface charge density, and electrical properties, such as capacitance. Thus, semiconductor nanofabrication technology is a key aspect of our approach.

To sequence dsDNA we first trap a molecule in a pore with d~2 nm; and then use low-noise, lock-in measurements of the sequence-dependent blockade current to discriminate between bases. There exists a voltage threshold for permeation of dsDNA through pores <3 nm in diameter, consistent with the notion that the molecule must be stretched by the applied electric field to translocate through the pore.[2-4] We show that if the voltage is rapidly switched during a translocation from a value of above the stretching threshold to value below, it is possible to weakly trap λ-DNA for as long as 56 s in a d~2.5 nm pore, which is about 59,000× longer than the duration of a typical translocation (900 μs) observed for voltages above the stretching threshold. Moreover, stretching dsDNA causes the base-pairs to tilt as they translocate through the pore, which in turn modulates the electrolytic current. Accordingly, we measure a sequence-dependent blockade signal when the molecule is trapped, suggesting we can discriminate A-T from C-G bps. Thus, our findings indicate that nanopores with d~2.5 nm afford us some control over both the translocation kinetics and the molecular configuration in the pore. Performance may be optimized and improved, making it suitable for high-throughput low cost sequencing.

In the sequencing process, we operate a nanopore like tweezers, repeatedly trapping dsDNA in the pore while performing high frequency, narrow band, lock-in measurements to resolve signatures of the base-pairs in the pore current. FIG. 1 illustrates schematically an exemplary process for sequencing DNA. The experimental apparatus has two chambers, each filled with electrolyte separated by a membrane with a nanopore in it that is <3 nm in diameter. dsDNA is injected in the cis chamber. A driving bias (see FIG. 1(h)), $V0$, is then applied and a corresponding ionic current (FIG. 1(i)), $I0$, flows in the absence of dsDNA through a nanopore (FIG. 1(a)). The driving bias causes dsDNA in the vicinity to migrate towards the pore and eventually it is captured by the field as shown in FIG. 1(b). The driving bias above threshold stretches the DNA, enabling it to thread the pore as shown in FIG. 1(c). At the onset of a current blockade, when a sequence-dependent blockade current, $I1$, is detected, feedback is used to reduce the voltage to $V_1$ and trap the molecule. At this time a lock-in measurement of the current, $I2$, is used to discriminate between the bases. After the measurement, the DNA is induced to advance by applying a voltage pulse greater than the threshold for the translocation—such as by moving one base at a time through the pore if switched sufficiently fast—until the current, $I3$, indicates the location of another base. And then the cycle continues from a measurement of $I3$ to a measurement of $I4$.

Requirements of a nanopore instrument for sequencing dsDNA include: 1. The geometry of the constriction must be stringently controlled as it determines the sensitivity and the electric field distribution. 2. The frequency response and noise performance have to be commensurate with switching the membrane voltage on a 10 nsec time scale for stepping from one base-pair to the next and detecting a single base-pair. 3 The molecule must be trapped in the pore for sufficient time to discriminate individual base-pairs. These three aspects are addressed in this example.

Figure 2:
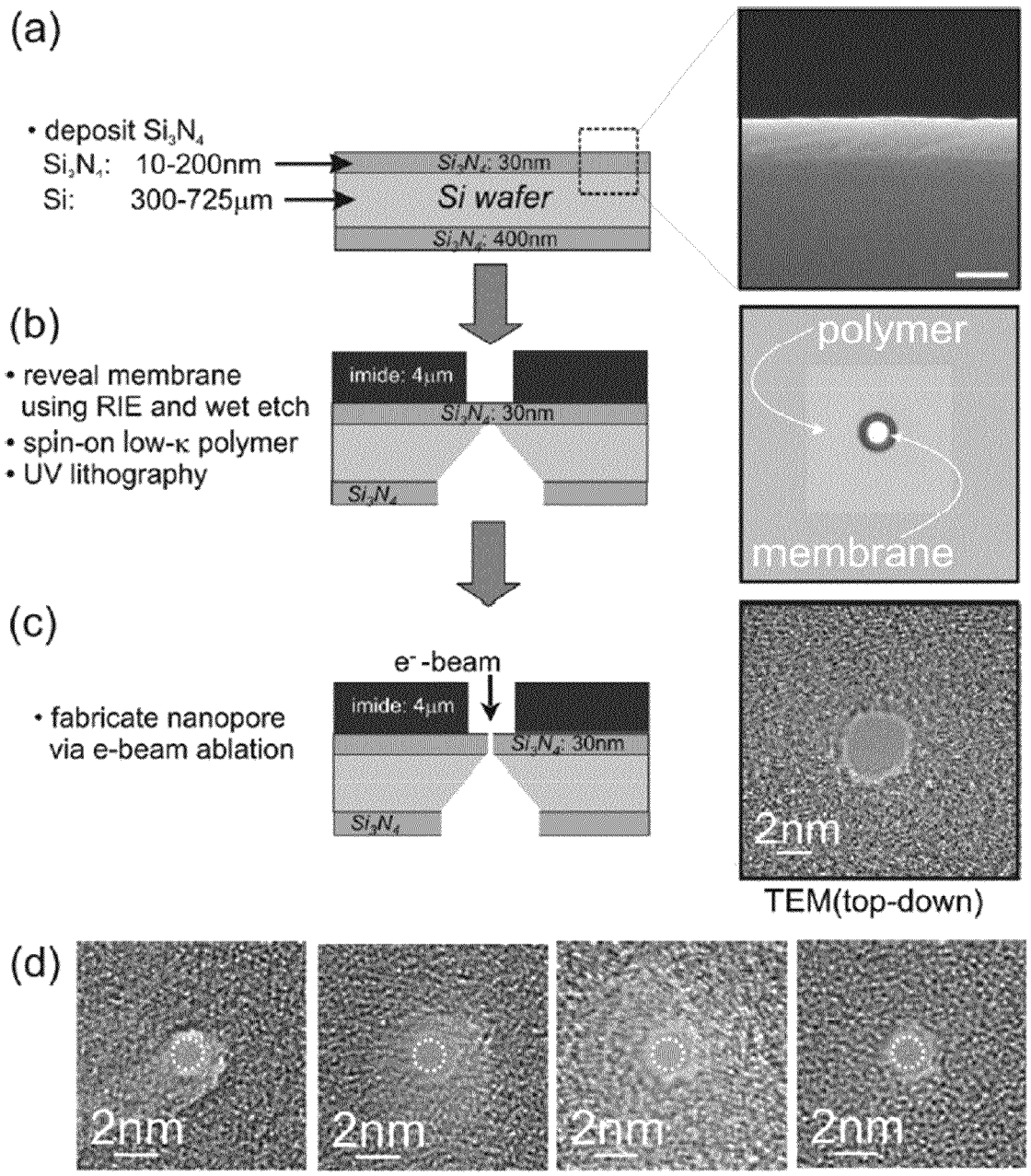
FIG. 2: (a) Membranes are formed by depositing a Si3N4 layer onto a silicon substrate. An SEM cross-section through the membrane structure is shown on the right. (b) DUV lithography and a combination of dry and wet etching through the backside of the wafer reveal the membrane. Subsequently, a photosensitive polyimide layer on the front surface is deposited and patterned to reduce the stray capacitance. An optical micrograph of a 10 µm window in polyimide used to define the membrane area is shown on the right. (c) After revealing the membrane, a pore is sputtered in it using a tightly focused, high energy electron beam. A nanopore through the membrane is shown on the right. (d) An array of 1.8 nm nanopores sputtered back-to-back in different membranes using similar conditions.

Fabrication of a Solid-State Nanopore <2.6 nm in Diameter. A unique aspect of the approach provided herein relates to the pore geometry; the thickness and composition of the membrane can all be controlled with sub-nanometer precision using semiconductor nanofabrication practices. This precision translates directly into control of the distribution of the electric field, (which has already led to the development of the most sensitive device for charge measurement: the single electron transistor.) Following several innovations[23-26] in the fabrication of solid-state nanopores, we develop methods for producing nanometer diameter pores in robust membranes as illustrated in FIG. 2. For example, we produce silicon nitride membranes by depositing an LPCVD Si3N4 film, ranging from 30 nm to 200 nm thick (nominally), on the top of a 300 μm thick (float-zone) Si handle wafer. To control the hydrophobicity, we control the amount of oxygen, silicon and nitride in the film. To reduce the thickness, either the nitride membrane is sputtered in a 5 μm×5 μm area using focused-ion beam milling or it is uniformly etched in 20:1 H2O:49% HF for 30-40 min at room temperature. Afterward, a polyimide photoresist with thickness of 3.6±0.6 μm is spin deposited on top of the chip, and a 5 μm window is opened over the membrane using UV lithography as shown in FIG. 2(a). The polyimide is used primarily to reduce the parasitic substrate capacitance.

A nanometer-size pore is subsequently sputtered into membranes like these using a tightly focused (1.6 nm spot-size) 9° α (cone angle), high energy (200 kV) electron beam emanating from a JEM-2010F transmission electron microscope (TEM) operating in convergent beam diffraction mode. Using TEM images taken at different tilt angles, we model the pore geometry as two intersecting cones (bi-conical) each with >20° cone angle.[26] By stringently controlling the beam conditions and membrane thickness (guaranteed by Electron Energy Loss Spectroscopy) it is possible to produce pores with practically the same geometry with sub-nanometer precision, as illustrated by the array in FIG. 2(d).

We use a new tool, a JEOL-2200F, which is an upgraded version of the JEM-2010F. The 2200F has a piezo-stage for atomically precise control over the sample position, and an aberration probe corrector that allows for increased (8×) brightness with a smaller probe. This corrector enables us to sputter with a smaller (<1.6 nm) spot which, in combination with the piezo-stage, provides more precise control over the pore geometry. This system facilitates the production of various nanometer-sized passages, such as a nanopassage having a 2.0×1.0 nm nano-slit with a 1 nm beam to closely conform to the twisting, propeller-like, helical shape of B-form dsDNA.

Electrical Characterization of a Solid-State Nanopore.

B-form dsDNA is a stiff, highly charged polymer with a solvated, helical structure about 2.6-2.9 nm in diameter, according to neutron scattering, that depends on the sequence and the number of strongly bound water molecules included in the primary hydration shell. So, precise, sub-nanometer control over the geometry of the nanopore, and the thickness and composition of the membrane translates directly into control of the distribution of the electric field, and accordingly the configuration of dsDNA in the constriction during a translocation.

When an electric field is applied across a membrane with a bi-conical pore d<3 nm in it that is immersed in electrolyte, the voltage is effectively focused onto that portion of the molecule near the center of the membrane over a region about 1-3 nm wide.2,3 This means that dsDNA has to first diffuse within range of the pore to be driven through it by the electric field. The rate of DNA capture is roughly given by $R=2\pi CDr$, with R the capture rate, C the concentration of DNA, D the diffusion constant of DNA in free solution, and r the radius of probable capture by the pore, dependent on the voltage applied.17 Once it is inside the pore, there are three main forces that affect the DNA. The first and strongest force is the electric field, acting primarily on the negatively charged phosphate backbone of DNA. The electric field causes electrophoretic motion of the DNA, driving it forward into the pore while the positively charged ion cloud surrounding it is driven back. There is an electrostatic interaction with the pore walls, and/or a nonpolar (van der Waals) interaction. And finally, there is a drag force associated with the movement of the polymer in solution, which is essentially a frictional force.

To determine the microscopic origin of the net force exerted on DNA in a nanopore at a given transmembrane bias, we use MD to simulate the system.27 We find three regimes for the dependence of the net force F on the applied electric field E, which we categorize according to the pore diameter. For a pore diameter >5 nm, the interactions with the pore itself are negligible, which makes sense considering the small Debye length (~1 nm) and the weak interaction of the van der Waals (r-6 dependence). When the pore diameter is between 3.6 and 5 nm, the electrolyte still behaves as it does in bulk solution, but direct interaction between the DNA and the pore surface becomes important. Finally, when d<3.6 nm, the viscosity of water in a thin film between DNA and a nanopore surface is larger than in the bulk and depends on the shearing velocity if DNA is moving. In this regime, the interactions between DNA and the pore can be much stronger and the microscopic details of the pore surface strongly affect the friction. A nonlinear dependence of the force on the applied electric field is expected, which is optimal for sequencing, as it allows the force and velocity of DNA translocation to be easily affected. Moreover, it forces DNA to move into and through the pore single file as more than one double helix cannot fit in the pore at the same time, occluding the electrolytic current through the pore and maximizing the signal.

When forced into a pore smaller than the double helix, the leading edge of the dsDNA penetrates the membrane to a constriction ~2.5 nm in diameter. If the differential force acting on the leading nucleotides is insufficient to stretch the helix, the translocation stalls there, but as the bias increases and the differential force exceeds that required to stretch dsDNA, the molecule is pulled towards the center of and eventually through the membrane. The two DNA strands do not pass through pores with diameters 1.6<d<2.5 nm in the same way, however. The confinement causes the basepairs to tilt.2,3 For diameters <1.6 nm, dsDNA unzips and the strands translocate through the pore one at a time.3

Figure 3:
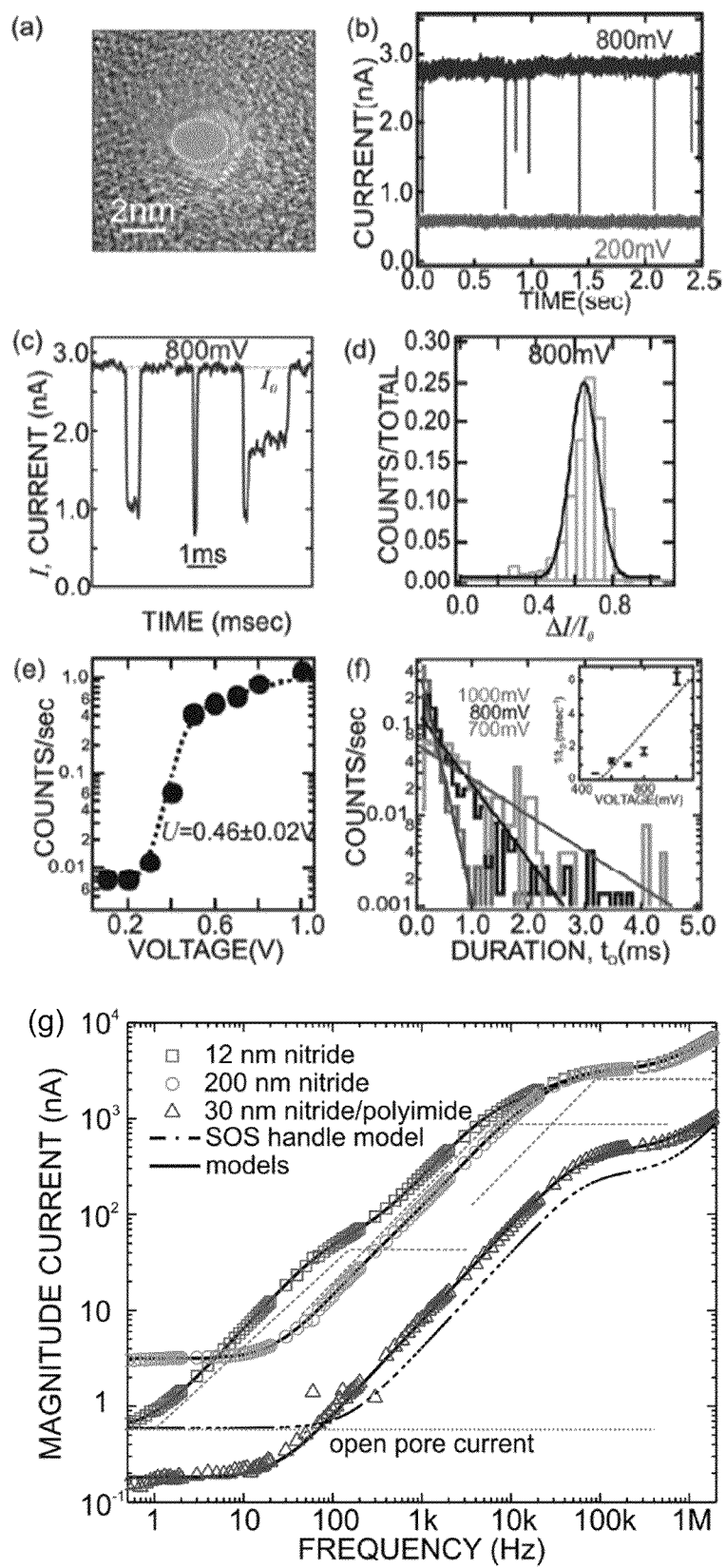
FIG. 3: a) A TEM micrograph of a 2.5×2.0 nm nanopore in a silicon nitride membrane 15 nm thick. (b) Electrolytic current measured in 100 mM KCl at 800 mV (top trace) and 200 mV (bottom trace) through the pore shown in (a) as a function of time. The frequency of blockades decreases dramatically with voltage; at 200 mV no transients are observed, suggesting no translocation through the nanopore and that the threshold voltage is greater than 200 mV. (c) Three examples of current blockades observed in the pore shown in (a) as a function of time at V=800 mV under the same conditions as (b). The open pore current at this voltage is about 2.85 nA. These current blockades are associated with λ-DNA translocating through the pore. (d) The frequency of blockades observed at 800 mV with a particular change in current normalized to the open pore current in the same pore. (e) The frequency of blockades observed with the same pore as a function of membrane voltage illustrating the frequency drop as voltage decreases below 0.5V. The dotted line represents a fit to the data. (f) Distributions illustrating the frequency as a function of the duration of a current blockade, $t_D$, above threshold at 1.0 V (smallest x-intercept), 800 mV (middle x-intercept) and 700 mV (largest x-intercept). The distribution depends sensitively on the voltage. Inset: tD-1, as a function of the applied voltage. (g) Magnitude of the pore current as a function of frequency measured through 3 different membranes: one with a nitride layer 12 nm thick; another with a 200 nm thick nitride layer and the third with a 30 nm thick nitride layer with a polyimide coating along with corresponding fits to the data (solid lines) (h) Schematics of the lumped element model for a composite polyimide/nitride membrane with a nanopore in it. The model is superimposed on the physical geometry (not to scale) and used to analyze the frequency responses shown in (a). The Faradic impedances, double-layer capacitances, depletion capacitance and series resistances are all represented and fit using ADS. (i) Simplified lumped element model derived from (h) (from Smeets (31)).
Figure 3:
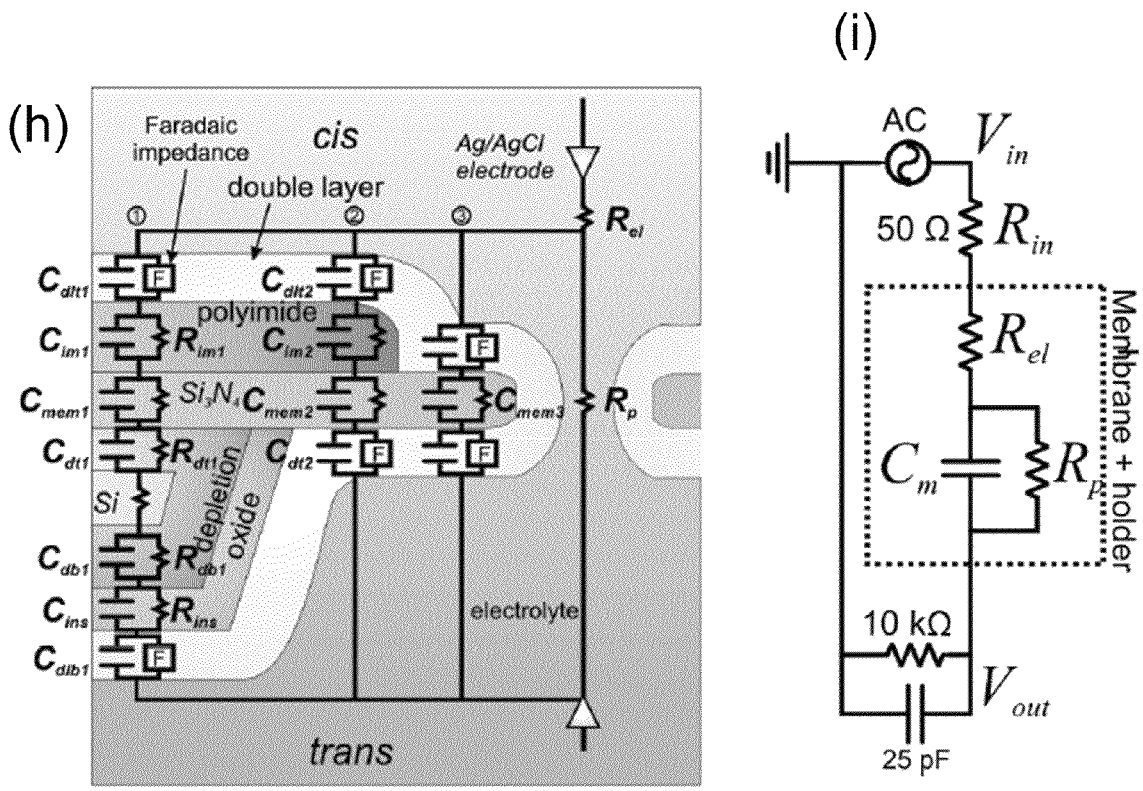

We test the electromechanics of dsDNA in a nanopore with a 2.5×2.0±0.2 nm cross-section—smaller than the DNA double helix—in a membrane 15.0±2.2 nm thick shown in FIG. 3(a). (This represents an early attempt to fabricate a nano-slit using the 2010F. Although the pore is elliptical, the beam diameter ~1.6 nm is too large to effectively sputter a slit with eccentricity ~1.) When λ-DNA is injected into the electrolyte at the negative (cis) electrode and 800 mV applied across the membrane, current transients like those shown in FIG. 3(b) are observed. The current transients occur randomly as a function of time as illustrated in the figure, but the interarrival time decreases with increasing concentration of DNA on the cis side of the bi-cell. There is a variety of transients, some of which are illustrated in FIG. 3(c). The distribution of transients can be represented by a blockade with a peak value at 62±11% of the open pore current (i.e. $\Delta I/I0=0.62\pm0.11$) as shown in FIG. 3(d). A blockade is supposed to be the reduction of the electrolytic current through the pore due to the translocation of DNA. In support of this interpretation, MD estimates indicate a $\Delta I/I0=0.4\pm0.1$ blockade through a 2.0 nm diameter pore in 100 mM KCl.

FIG. 3(b) illustrates threshold behavior, showing a dearth of transients found in a current trace measured at 200 mV in comparison with 800 mV. FIG. 3(e) summarizes the frequency of blockade events observed as a function of the voltage applied across the membrane over the range from 100 mV to 1V. Generally, we observe that the number of blockades rises abruptly over a range of ~200 mV near a threshold that is sensitive to the pore diameter. If we assume that each blockade corresponds to dsDNA permeating the pore, then the permeation rate can be described by the transition-state relation of the Kramers type:4 $R=R0V/(1+\exp[q^*(U-V)/kT]$, where R0 is a frequency factor, q*U is the effective barrier height, q*V is the reduction in the energy barrier due to the applied potential, and kT is the thermal energy. Using this relation, the data are fit and the results overlaid on the scatter plot in FIG. 3(e). We find a threshold of U=0.46±0.02V with q*=0.8±0.2e, which presumably corresponds to the force required to stretch the leading nucleotides in the pore—below this voltage DNA is not supposed to permeate the membrane. This conclusion is supported by prior work2-4 which shows that the threshold depends on pH, pore diameter, membrane thickness, dsDNA sequence and methylation profile. Typically, for a 2 nm diameter pore in a 10 nm thick membrane at pH 8, the threshold voltage is ~3V.

The duration of the blockade grows longer with the DNA contour length,26 which supports the interpretation of the blockade current as a translocation across the membrane. The dependence of the blockade duration on the membrane voltage offers more support for this interpretation. FIG. 3(f) shows the frequency of current transients associated with λ-DNA as a function of duration with the voltage as a parameter. If the blockade duration corresponds with the interval that DNA blocks the pore, then the average transient width tD signifies the time required for 48.502 kbp λ-DNA to translocate through the pore. We find that tD=0.160±0.01 ms, 0.53±0.06 ms, 1.1±0.1 ms, 0.82±0.07 ms and 2.49±0.25 ms for voltages of 1.0V, 800 mV, 700 mV, 600 mV and 500 mV respectively. The corresponding translocation velocity estimated from the quotient ranges from 1 bp/3.3 ns at 1V or 1 bp/11 ns at 800 mV to 1 bp/50 ns at 500 mV, which is consistent with MD simulations performed under similar conditions. The inset to FIG. 3(f) shows a plot of the voltage dependence of the reciprocal of the average transient width, i.e. $1/tD$, measured above threshold. $1/tD$ falls abruptly near the threshold value, which is consistent with the idea that the molecule may become trapped in the pore near the threshold voltage. The line in the inset is a least-squares fit to the data, which has a slope of 11 $V^{-1}$ $s^{-1}$ with a voltage-intercept of 0.53V, which is comparable to the threshold voltage inferred from FIG. 3(e).

These observations are in sharp contrast with prior work on larger diameter pores,29,30 and measurements that we performed on a 3.6×3.2±0.2 nm pore with a cross-section larger than the DNA double helix cross-section in a 31.5±2.0 nm thick nitride membrane. We observe current blockades at much lower transmembrane bias in the 3.6×3.2 nm pore—into the millivolt range. If we assume that each blockade corresponds to dsDNA permeating the pore and fit to the transition-state relation, we find a threshold voltage of U<0.06±0.02V with q*=1.0±0.2e (data not shown.) And if the blockade duration corresponds with the interval that DNA blocks the pore, and the average transient width tD signifies the time required for 48.502 kbp λ-DNA to translocates through the pore, then for the 3.6×3.2 nm pore, tD=0.031±0.007 ms 0.0321±0.007 ms, 0.0677±0.003 ms, and 0.403±0.26 ms for voltages of 600 mV, 400 mV, 200 mV and 100 mV, respectively, which is consistent with prior estimates of the translocation velocity >1 bp/10 ns.29,30

The high translocation velocity observed in a solid-state nanopore at the high voltage required to stretch DNA demands a nanopore with a high frequency response to detect blockades, otherwise they cannot be resolved reliably (and so typically we use quantitative PCR to count the molecules that permeate the membrane through the pore.) FIG. 3(g) shows the frequency responses of four types of membranes: two associated with different nitride thicknesses, 12 nm and 200 nm, on a silicon substrate, a third associated with a composite 30 nm nitride membrane coated with a 3.6 μm polymer film, all on a silicon substrate, and a fourth a simulation of a 12 nm nitride membrane on a sapphire substrate—each membrane contains a nanopore ranging in diameter from 2-5 nm. Generally, we find that the current frequency response consists of two components: one associated with the conductance through the pore, which predominates at low frequency and is manifested by zero-slope versus frequency; and another due to the displacement current associated with the membrane capacitance and associated parasitics. While both depend linearly on the applied voltage, the displacement current increases with frequency, which is why the current grows so large at high frequency.

Detailed models that precisely capture the frequency response of the nanopores (FIG. 3(h)), which are rooted in the physical structure and reflect, in a limited way, the distributed nature of the electrical parameters are developed. In addition to the capacitance of dielectric materials such as polyimide, Si3N4, the models also account for the depletion layer capacitance in the Si handle, the dielectric loss in each case, the resistivity of the substrate, the resistivity of the KCl electrolyte, the double layer that is associated with the interface between a charged surface and an electrolyte solution, and the Faradic impedances associated with charge transfer: Fits to the data are represented by the solid lines in FIG. 3(g): the models accurately account for the frequency response. For economy, to illuminate the relationship between the ac pore current, i, and the ac voltage, $v_m$, responses across the membrane, we use the simplified model shown in FIG. 3(i) due to Smeets et al.31 This model is comprised of an effective capacitance Cm representing the membrane in parallel with the pore resistance Rp and in series with the electrolyte/electrode resistance Rel. According to the model, the Fourier transform of the frequency response functions are given by:

$$i(\omega) = \frac{(1+j\omega R_p C_m)}{R_p + R_{el}(1+j\omega R_p C_m)} v_{in} \rightarrow v_m(\omega) =$$

$$i(\omega)\frac{R_p}{(1+j\omega R_p C_m)} = \frac{R_p}{R_p + R_{el}(1+j\omega R_p C_m)} v_{in} \cong \frac{1}{1+j\omega C_m R_{el}} v_{in}$$

so that $v_m(t) = v_{in} e^{-t/C_m R_{el}}$. Thus, the transient voltage response time is determined by the time constant: Cm Rel. If Cm is reduced by mitigating the effect of parasitics, then the high-frequency response is determined by the time constant associated with the window capacitance and the load resistance, which consists of the amplifier load in series with the electrolytic resistance. The window capacitance is controlled by the membrane thickness and the area, while the series resistance can be minimized by increasing the electrolyte concentration. For example, FIG. 3(g) illustrates the dramatic effect that parasitics associated with the substrate have on the frequency response. After replacing the handle wafer with sapphire instead of silicon, the pore conductance now predominates the current response up to a frequency of fz0=½πRpCm~200 Hz and the membrane capacitance is substantially reduced to Cm=1.6 pF. With this capacitance and 1M KCl, the voltage response time is ~4 nsec, which is fast enough to move from one base-pair to the next at 1 bp/10 ns.

In addition to the capacitance of dielectric materials such as polyimide and Si3N4, the models also account for the depletion layer capacitance in the Si handle, the dielectric loss in each case, the resistivity of the substrate and the KCl electrolyte, the double layer that is associated with the interface between a charged surface and an electrolyte, and the Faradic impedances associated with charge transfer. To determine the parameters governing the model, which are delineated in Table 1, the values of the various lumped elements were first estimated from the geometry and then the data was fit using a least-squares minimization algorithm to converge to the final values. Fits to the corresponding models are represented by the solid lines in FIG. 3(g).

This model accurately accounts for the frequency response of the current. And since it is derived from the physical structure, it can be used to elucidate strategies for improving the signal-to-noise through changes in the pore-membrane structure. For example, the membrane voltage determines the electric field in the pore, which affects the translocation kinetics as well as the potential barrier associated with the molecule in the constriction and therefore the blockade current. To illuminate the relationship between the ac pore current, i, and the ac membrane voltage, $v_m$, response across the membrane, we used for economy the simplified version of the model of FIG. 3(h) shown in FIG. 3(i). This model is comprised of an effective capacitance Cm representing the membrane in parallel with the pore resistance Rp and in series with the electrolyte/electrode resistance Rel. According to the model, the Fourier transform of the frequency response functions and the corresponding membrane voltage response are provided so that $v_m(t)$ is obtained, as described above. Thus, the transient voltage response time is determined essentially by the time constant: CmRel. As illustrated in Table 1, typically, fits to the data yield effectively Cm=100 pF and Rel=10 kΩ for 1M KCl electrolyte so that τ~1 μsec. If Cm or Rel is reduced by mitigating the effect of parasitics, then the high-frequency response can be improved.

The so-called "membrane" capacitance is actually dominated by parasitic capacitances associated with the seal area over the handle wafer and the cabling, while the electrolyte resistance is determined mainly by the electrolyte concentration and the Ag/AgCl electrodes geometry relative to the pore. We can reduce the parasitic capacitance by using: 1. thicker Si3N4 membranes; 2. composite membranes consisting of thick polyimide on a thin miniaturized Si3N4 membrane; or by 3. eliminating depletion in the handle wafer; or 4. eliminating cabling; and/or by using capacitance compensation through external circuitry, which has been used successfully for patch clamping. While capacitance compensation can provide a vast improvement in the high frequency performance, it also contributes noise,5 so mitigation of the parasitic capacitance through miniaturization of the membrane still offers the most promising route to high fidelity electrical measurements as evident from the improvement illustrated by 30 nm thick nitride/polymer composite membrane shown in FIG. 3(a). FIG. 3(a) also illustrates the effect the parasitic capacitance associated with the substrate has on the frequency response. After replacing the handle wafer with sapphire instead of silicon, the pore conductance now predominates the current response up to a frequency of fz0=½πRpCm~200 Hz and the membrane capacitance is substantially reduced to Cm=1.6 pF. With this capacitance and 1M KCl, the membrane voltage response time becomes CmRel~4 nsec, which is faster than the DNA translocation velocity (1 bp/10 ns).

Further improvements can be gleaned from miniaturization and repositioning the Ag/AgCl electrodes closer to the pore. For a micro-disk geometry embedded between two dielectrics, it can be shown that the resistance follows the law: (¼R)(1/t), where R is the radius and t the exposed thickness. Thus, we can use a composite nitride/polyimide membrane 1 µm×1 µm in area with embedded Ag/AgCl electrodes 1 µm thick sandwiched between the polyimide and the nitride, 1 µm in diameter encircling the membrane, all on a sapphire substrate. We estimate electrolyte resistance to be ~500 for 1M KCl—representing an improvement of 200×.

We expect the largest signal for the smallest pore diameter, but if the bandwidth is too narrow, it is difficult to resolve the signature associated with the translocation of a single basepair. (Repeated measurements made using multiple pores with multiple copies of DNA or multiple passes with a single molecule doesn't really solve this problem.) So, following Smeets et al.31 we sought a compromise between signal-to-noise and bandwidth by analyzing in detail the electrical characteristics of solid-state nanopores, representing them by the equivalent lumped element circuit shown in FIG. 3(i).

The noise power spectra, corresponding to the measured frequency response of the same three nanopores in FIG. 3(g), are shown on FIG. 4(a) along with the spectrum of a 300 MΩ resistor, a value comparable to the pore resistance. We analyze the noise into components that can be categorized as: 1. thermal noise associated with the resistance of the electrolyte and the pore resistance 2. 1/f or flicker noise that is related to the carrier density in the pore; 3. dielectric noise associated with the membrane and holder; and 4. noise originating with the measurement amplifier. FIG. 4(a) shows the measured noise spectra superimposed on the fit of the thermal (black), 1/f (red), dielectric noise (cyan) and amplifier noise (green) contributions along with the total (orange). The thermal noise density associated with pore resistance, is negligible over the band. At low frequencies, the noise power density is inversely proportional to the frequency, which is indicative of the presence of excess, or 1/f, noise. Its noise power spectrum is modeled by: $S_{1/f} = I^2 \alpha / N_c f^\beta$, where I is the current through the device, α is the Hooge parameter (an empirically determined proportionality constant), Nc is the total number of current carriers, f is the frequency, and β is an exponent that is typically unity. This portion of the spectrum can be described with β=1.085±0.010, depending on the electrolyte concentration. At frequencies >1 kHz, 1/f noise becomes negligible, and the spectrum exhibits linear frequency dependence up to about 50 kHz. The noise in the range 1-50 kHz is dominated by dielectric noise with a spectrum of the form: $S_d = 4k_B TDC_D (2\pi f)$, where kB is Boltzmann's constant, T is the absolute temperature, and D and CD are the loss tangent and capacitance of the dielectric material. This capacitance and loss tangent are directly related to the lumped elements comprising the circuits in FIG. 3(i): e.g. the loss tangent is the tangent of the angle between the Cm capacitor impedance vector and the negative reactance. Finally, above 50 kHz, the spectrum is strongly affected by the bandwidth of the amplifier (~55 kHz). The amplifier noise (referenced to the amplifier input) has a density spectrum: $S_{amp} = 4\pi^2 f^2 \in_s^2 Cm^2/(1+4\pi^2 f^2 \tau_{sr}^2)$ where $\in_s^2$ is the thermal voltage noise of the series (KCl and AgCl electrode) resistance, $\tau_{sr}$=RsrCm and Rsr is the uncompensated series resistance. The dip >50 kHz is due to the amplifier, which we have modeled as a low pass filter.

Figure 4:
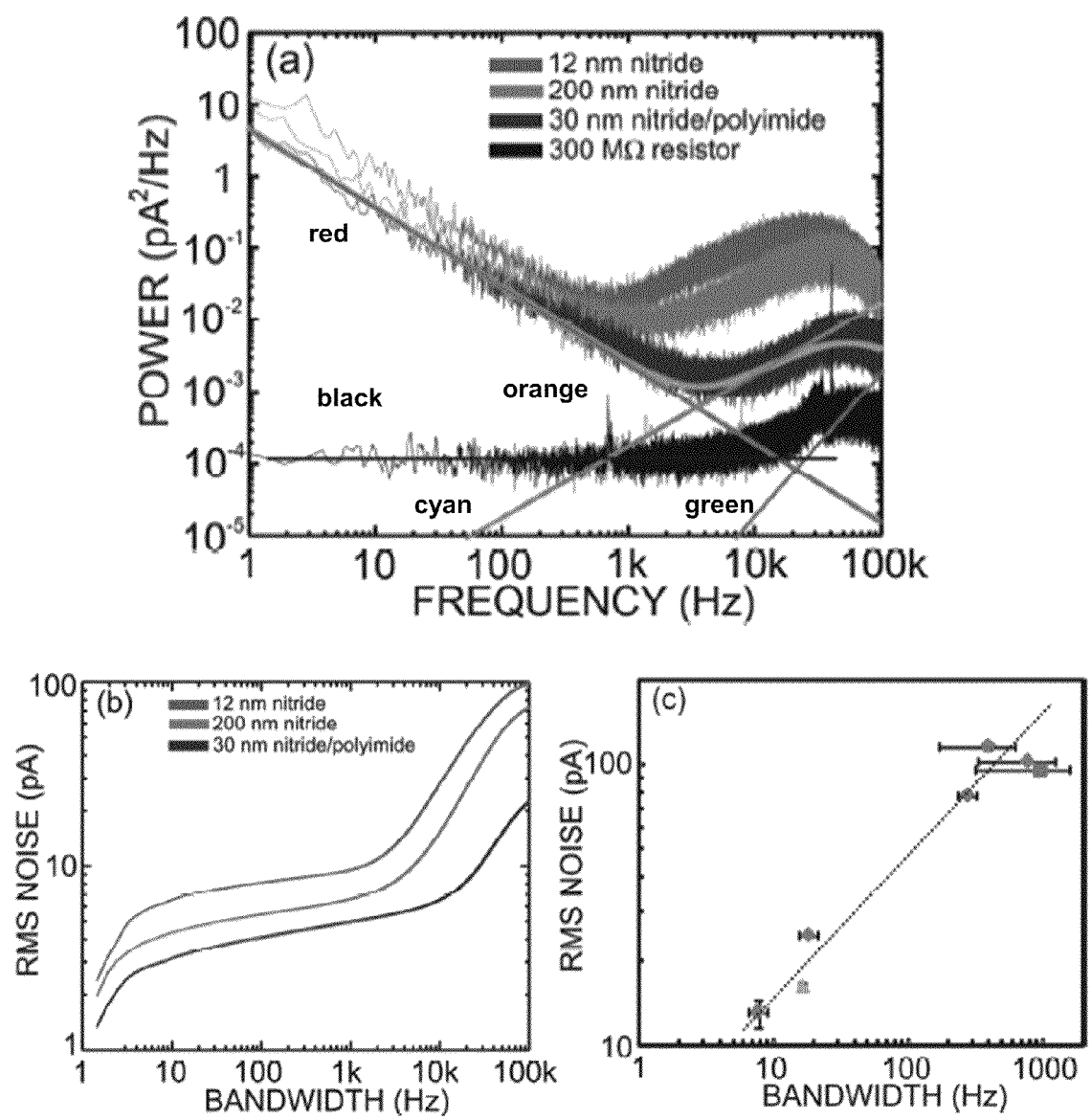
FIG. 4: (a) Noise power spectra of 3 nanopores measured in FIG. 3(g) with different effective capacitance. From bottom to top, a 300MΩ resistor, a 5 nm pore in polyimide covered Si3N4 membrane, a 4 nm pore in ~200 nm Si3N4 membrane, and a 3 nm pore in 12 nm Si3N4 membrane. The low frequency 1/f noise (red line), the high frequency dielectric noise (cyan line) along with the amplifier noise (green) are analyzed for a 5 nm pore in polyimide coated membrane. The fit to the total noise is shown in orange. (b) The rms current noise as a function of bandwidth. The capacitive noise predominates at high frequency. (c) The rms-current noise increases with effective capacitance. (d) Effect of electrolyte concentration on noise power spectra for a 3 nm pore in 12 nm thick nitride. 1/f noise depends on electrolyte concentration while dielectric noise does not. (e) λ-DNA current blockade through two 3.0±0.2 nm diameter pores: one in a 30 nm thick nitride membrane (top trace) and another in the same membrane that is also coated with 3.6 µm thick polyimide layer (bottom trace) except for a 10 µm window. The peak-to-peak noise is dramatically improved with polyimide.
Figure 4:
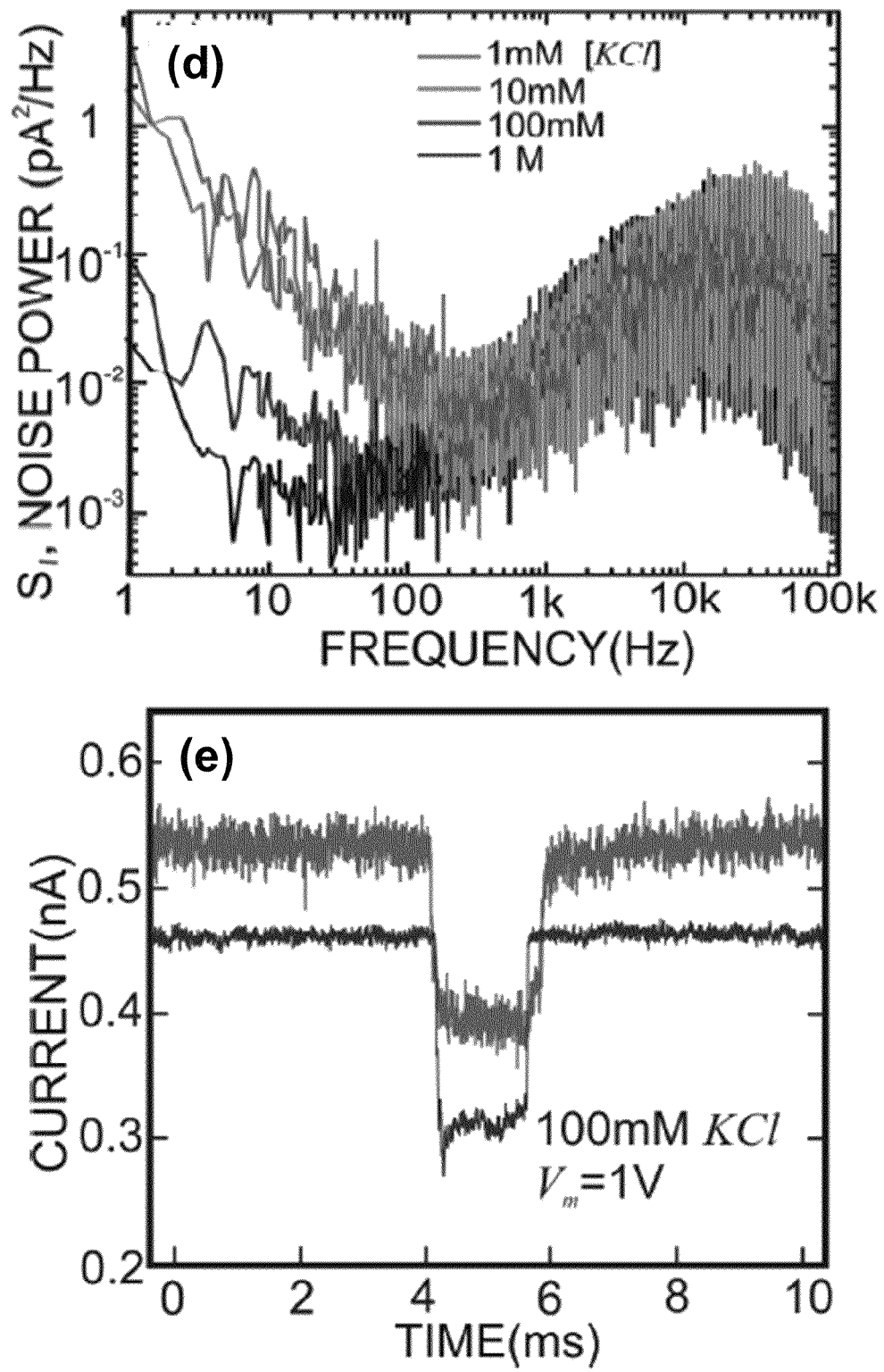

From this analysis we deduce that the dielectric capacitance dominates the total noise. FIGS. 4(b,c) shows how the rms-current noise increases with bandwidth and capacitance over the range from 8 pF-900 pF. Thus, reducing the membrane capacitance is the key to improving both the frequency and noise performance.

Trapping a Single DNA Molecule in a Nanopore:

The data of FIG. 3(f) indicates that dsDNA can be trapped in a nanopore that is smaller in diameter than a canonical double helix, if the membrane voltage is switched to a value below threshold while the molecule is translocating through the pore. To examine this further, first we force dsDNA into a 2.5 nm pore and then, once a blockade in the current is detected, reduce the transmembrane bias at high-speed while the molecule is still in the pore. Once the dsDNA is in the pore, if the bias is reduced below the stretching threshold, the pore functions like a trap in resisting the motion of the molecule. FIGS. 5(a) and (b) show data demonstrating that it is possible to weakly trap a single λ-DNA molecule once it is translocating through the pore by switching the electric field at high-speed. During normal operation, a transmembrane bias of 800 mV, which is above threshold according to FIG. 3(d), is applied across the membrane resulting in an open pore current >3 nA. Once the onset of a blockade like that shown in the inset to FIG. 5(a) is detected by a differentiator, a programmed delay of about 200 µs is introduced before a latch switches the voltage from 800 mV to 200 mV—a value well below the threshold. All the while, the pore current is monitored. According to the ac models we have developed, the membrane voltage tracks the voltage applied to the Ag/AgCl electrodes, but with a longer time constant (<500 ns). Corresponding to the abrupt change in voltage, a current transient occurs on a sub-microsecond time scale. The transient sometimes saturates the current amplifier immediately after switching from 800 mV for an interval of about 1-3 ms, even with compensation. (This occurs because i=CdV/dt is still too large since dV/d/=0.6V/10 ns). Eventually, the current returns to the open pore value, 10, but not before we observe a sharp transient like that shown near t=7.709 s in FIG. 5(a).

Figure 5:
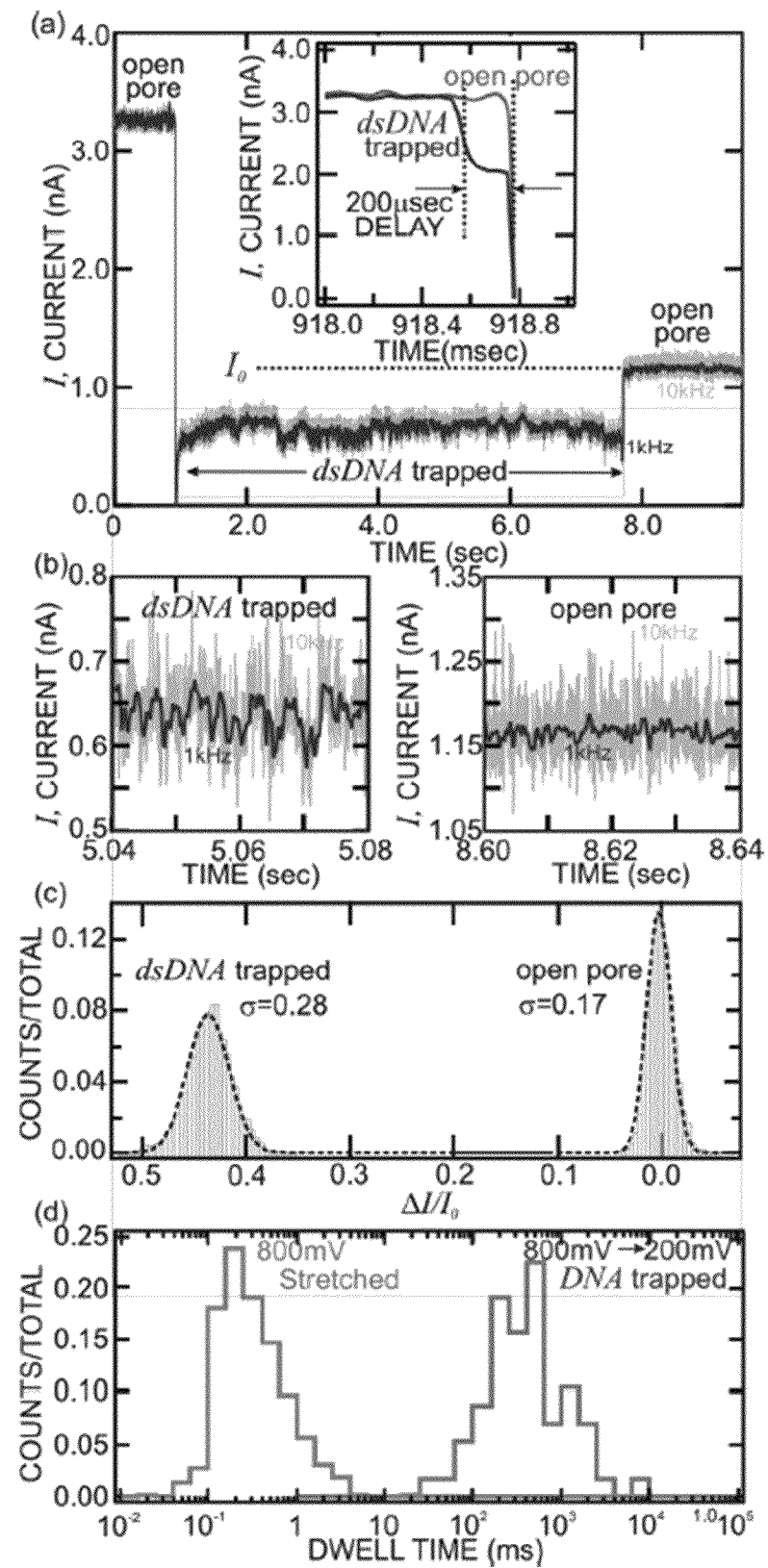
FIG. 5: (a) Triggered by the onset of a blockade in the 2.5 nm pore, the voltage across the pore is switched from 800 mV (above the threshold for stretching) to 200 mV (below threshold). As a result, the duration of the current transient (blue) increases from about 200 µs to about 6.73 s. The transient observed at 7.709 s reflects a single DNA nucleotide base or base-pair exiting the pore. The grey trace represents data taken at a 10 kHz bandwidth; the blue trace is the same data with a 1 kHz (8-pole Bessel) filter. Inset: Detail showing the onset of a current transient and the 200 µs built-in delay executed before triggering the voltage step. (b) A magnified view of the pore current observed during (left) and after (right) the blockade, showing the magnitude of the current fluctuations. The blockade fluctuations are related to bps translocating at 1 bp/221 µs. (c) Distribution of the current as a function of $\Delta I/I0$ during the blockade (left) and the open pore (right). (d) The distribution of dwell times observed at 800 mV (grey), and after the voltage is switch from 800 mV to 200 mV to the return to I0 (blue).

We assume that transients like these are indicative of the λ-DNA molecule exiting the pore after 6.73 s. So, we reasoned that the current blockade observed during the time interval from t=0.9814 to 7.709 s must be evidence of a weakly trapped λ-DNA molecule in the pore. Consistent with this inference, we do not observe a current blockade at 200 mV when there is no onset of a blockade at 800 mV. Moreover, the 3.6×3.2 nm pore at a constant bias of 200 mV shows a distribution of blockade durations that peaks near 200 μs, but does not exceed 1 ms, which makes the long (6.73 s) duration shown in FIG. 5($a$) extraordinary. The fluctuations illustrated in FIG. 5($b$) also support the mechanism of pore current blocked by a λ-DNA: we observe that for t<7.709 s the amplitude of the current fluctuations increases relative to the open pore value found for t>7.709 s. FIG. 5($c$) delineates the relative change of the current fluctuations during the blockade from the open pore current. Focusing on the data filtered with a low-pass 1 kHz filter, the ΔI/I0 width of the histogram taken from the blockaded current is 0.28I0, while the open pore histogram measured over the same 3 s interval is only 0.17I0 wide, indicating a signal beyond the noise for t<7.709 s, that is likely due to base-pairs translocating through the pore. Different base-pairs can be resolved if the signal is averaged over a sufficient time.

If the molecule is weakly trapped in the pore, then the average translocation velocity must have slowed substantially to a value of about (48.5 kbp–200 μs×1 bp/11 ns)/500 ms=1 bp/221 μs, which is about ×20,000 times slower than the velocity estimate for tD obtained at 800 mV. After repeating this type of measurement hundreds of times on the same pore, a comparison between the distribution of the duration of blockades observed with a transmembrane bias of 800 mV, and the time that expires between the triggered voltage switch from 800 mV to 200 mV and the return of the current to the open pore value reveals the dichotomy illustrated in FIG. 5($d$). While the peak in the distribution obtained at a constant bias of 800 mV occurs near tD=200 μs, the distribution found when the voltage is switched from 800 mV to 200 mV occurs near tD~500-600 ms. If we assume that the molecule is weakly trapped, then the translocation velocity at the peak must have slowed substantially to a value of about (48.5 kbp–200 μs×1 bp/11 ns)/500 ms=1 bp/17 μs, which is more than ×1500 times slower than the velocity at 800 mV. We do not observe blockades >4 ms at constant bias, however, we have observed blockades after switching as long as 6.7 s. The distribution of the normalized blockade current ΔI/I0 with a constant bias of 800 mV is ΔI/I0=0.62±0.11 wide, while the blockades measure after switching the voltage from 800 mV to 200 mV is ΔI/I0=0.46±0.07 wide, which overlap within the error.

Figure 6:
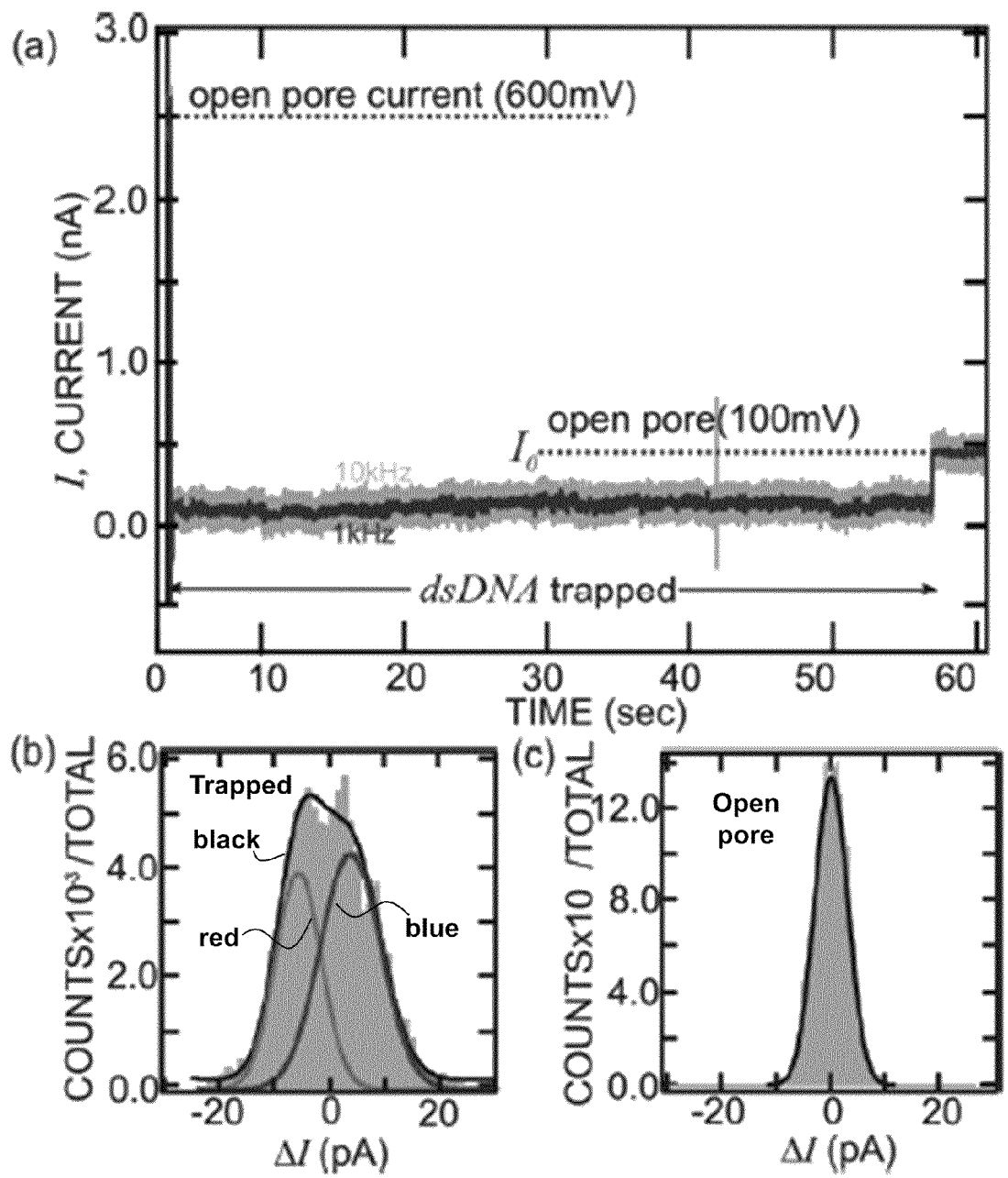
FIG. 6: Trapping a λ-DNA molecule in a nanopore. (a) A 56 s current blockade. Triggered by the onset of a blockade in a 2.5 nm pore, the membrane voltage is switched from 600 mV (above threshold, $V_T$) to 100 mV (below threshold, $V_T$). As a result, the width of the current transient (blue) increases from about 900 µs to ~56 s. The transient observed at 58.8 s is supposed to indicate a λ-DNA molecule exiting the pore. The grey trace represents data taken at 10 kHz bandwidth; the blue trace is the same data with a 1 kHz filter. (b) Distribution of the current during the blockade for t<58.8 s observed in the interval 40.0-40.5 s (left), and the open pore for t>58.8 s (right) The distribution for the trapped molecule can be fit to two Gaussians: one (solid blue) offset from the median ($\Delta I=0$) by +2.86 pA with a width of 7.6 pA; and another (solid red line) offset by −6.51 pA with a width of 5.8 pA. The black line represents the sum. (c) Signal from base-pairs translocating through an open pore. (d) Histograms showing the distribution of dwell times observed at 600 mV (left-most histogram) and the distribution of elapsed time spanning the instant when a blockade event triggers the voltage switch from 600 mV to 150 mV (blue) or 100 mV (red) to the return of the current to the open pore value seconds later. The peak in the distribution of current blockade durations (blue) increases from about 900 µs to about 200 ms, increasing ×200.
Figure 6:
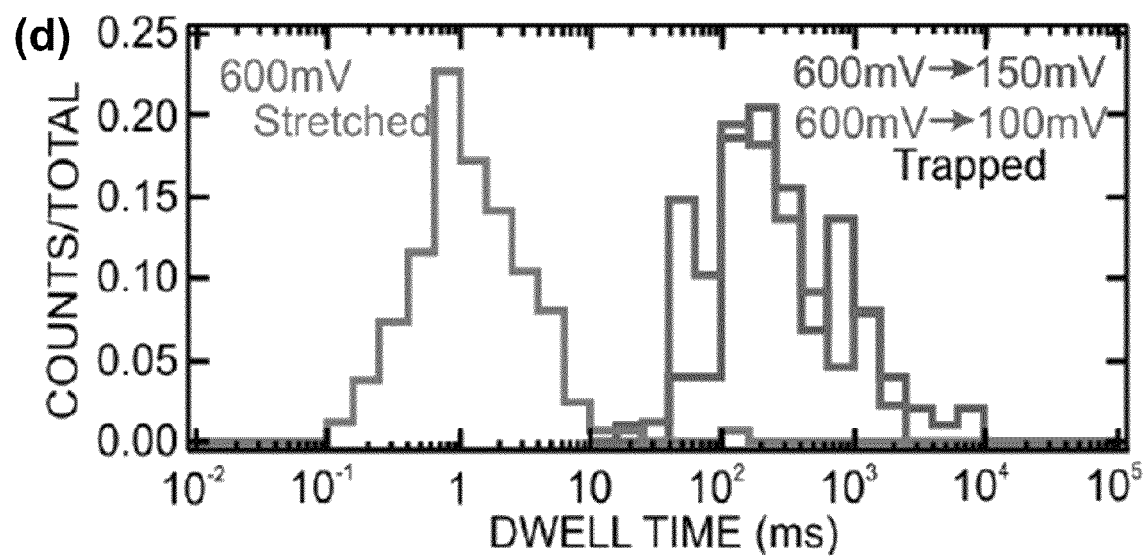

In support of these conclusions, we have made similar findings on three pores with similar geometries. FIG. 6($a$) shows an interesting event obtained from a 2.5 nm pore, which represents another trapped λ-DNA molecule. First, a bias of 600 mV (above threshold) is applied across the membrane, and then, once the onset of a blockade is detected, a delay of about 200 μsec is introduced before the voltage is switched from 600 mV to 100 mV (below threshold), while the current is monitored. Eventually, the current returns to the open pore value, near t=58.8 s in FIG. 6($a$). We assume that this transient is indicative of the molecule exiting the pore after 56 s, corresponding to a translocation velocity of >1 bp/1.8 ms.

With the molecule trapped under the conditions (i.e. for t<58.8 s), we filter the current data shown in FIG. 6($a$) using a 20-1 kHz bandpass filter and formed histograms of the current fluctuations using 0.5 s windows. Each window shows a histogram similar to that shown in FIG. 6($b$), which can be represented by the superposition of two Gaussian distributions: one (solid blue) offset from the median (ΔI=0) by ΔI=+2.86 pA with a width of 7.6 pA; and another (solid red) offset by ΔI=−6.51 pA with a width of 5.8 pA. We attribute these separate peaks to resolved C-G/G-C and A-T/T-A bps, respectively. The base-pairs can be resolved in this case because of the correspondingly longer (~2 ms) time that the base-pair is trapped in the constriction compared with the (200 μs) trap time for the molecule in FIG. 5($a$). In particular, as shown in FIG. 6($d$), the trapping or holding time (indicated as dwell time on the x-axis), significantly increases when the voltage is decreased from a threshold or driving voltage (600 mV) sufficient to stretch the DNA to a correspondingly lower holding voltage of 150 mV or 100 mV. The blockade duration increases from about 900 μs to about 200 ms.

Figure 7:
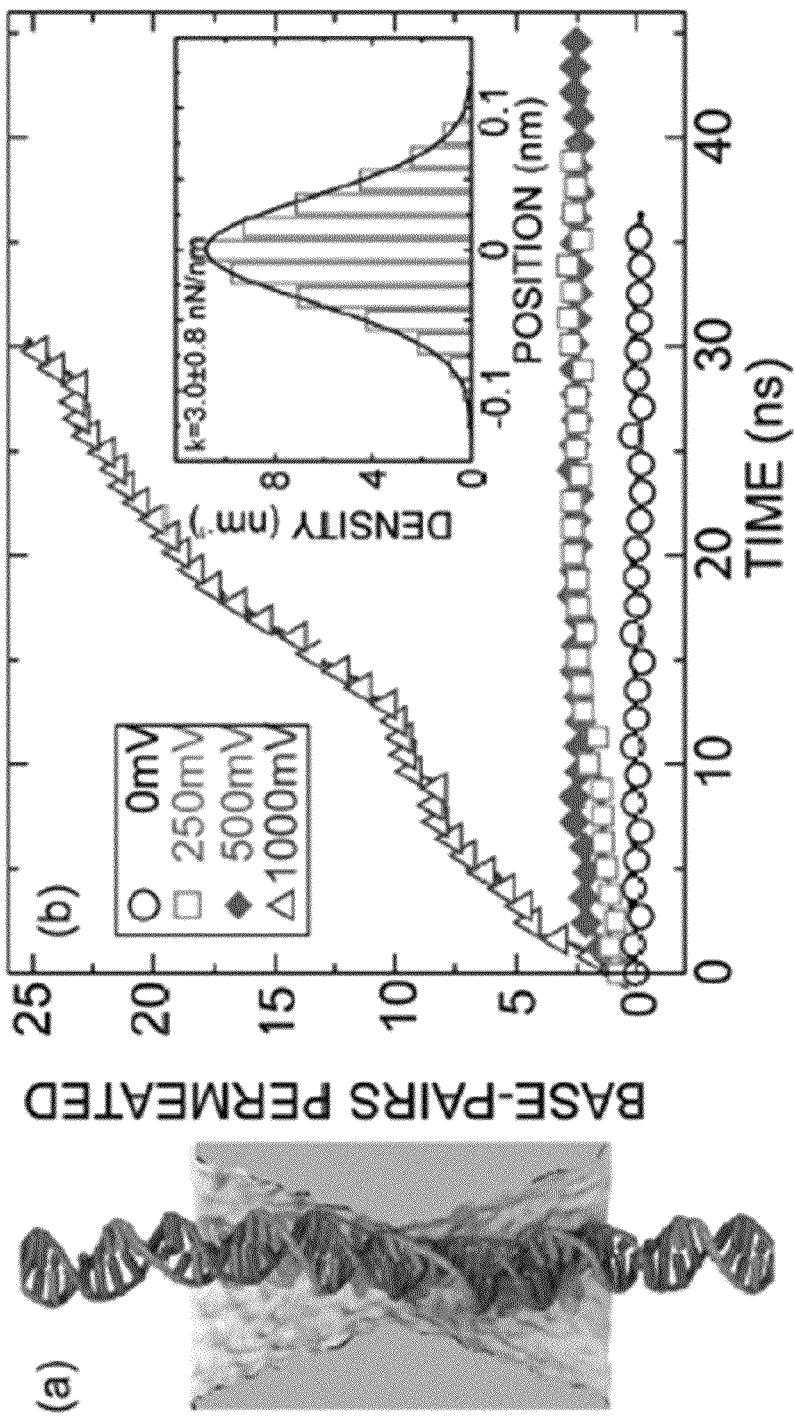
FIG. 7: MD simulation of the nanopore trap. (a) Snapshot of the simulated system that includes dsDNA, a 2.6 nm×2.1 nm-cross section pore, water and ions (not shown) at a transmembrane bias of 250 mV. The molecular conformation is stretched in the constriction beyond the 0.34 nm about 8-20%. (b) The number of basepairs permeating through this pore in four MD simulations carried out applying different biases. The simulations predict a voltage threshold for restarting the translocation between 500 mV and 1.0V. (Inset) Histogram of the displacements of the basepair nearest to the center of the membrane in a simulation carried out at a 0V bias. The solid line shows the distribution for a harmonic trap with a k=3.0±0.8 nN/nm spring constant.

Trapping a Single DNA molecule in a Nanopore (Simulation): We use all-atom MD simulations in conjunction with Brownian Dynamics and QM/MM methods to both visualize and test the interactions between the dsDNA and the pore, and optimize the instrument for sequencing. For example, MD simulations of the experiments described above demonstrate that the motion of the dsDNA can be slowed or effectively stopped when the driving voltage is turned off, that there exists a threshold voltage for restarting the translocation process and that the base-pairs can be resolved if signal is averaged long enough. FIG. 7($a$) illustrates the simulated system at a 250 mV transmembrane bias, which includes an effectively infinite fragment of dsDNA, a nanopore of a 2.6 nm×2.1 nm cross-section, and 100 mM KCl. The molecular conformation in the constriction is stretched beyond 0.34 nm per basepair by about 8-20%. DNA transport is observed only when a bias of 1V is applied, as illustrated in FIG. 7($b$). At 0.25 and 0.5V, the DNA's motion is arrested, following a small initial displacement caused by stretching. (This threshold should be smaller than the threshold for stretching the leading nucleotides, since the molecule is already in the pore.) By analyzing dsDNA's displacements at 0V, we determine that the pore acts as a harmonic trap with an effective spring constant of 3.0±0.8 nN/nm, as shown in the FIG. 7($b$) inset.

Theoretical studies have shown that the probability of an escape from a trap depends sharply on the force applied to the molecule, explaining the threshold seen in FIG. 7($b$). The threshold force for restarting the motion among a regular array of harmonic wells, q*E, is determined by the product of the effective spring constant, k, and the separation between bases x0: i.e. q*E~kx_0. The trap profile should be invariant for displacing dsDNA by one basepair, so x_0=0.5*0.34 nm. Thus, the upper bound of the force required to displace dsDNA between two adjacent traps is 480 pN.

Figure 8:
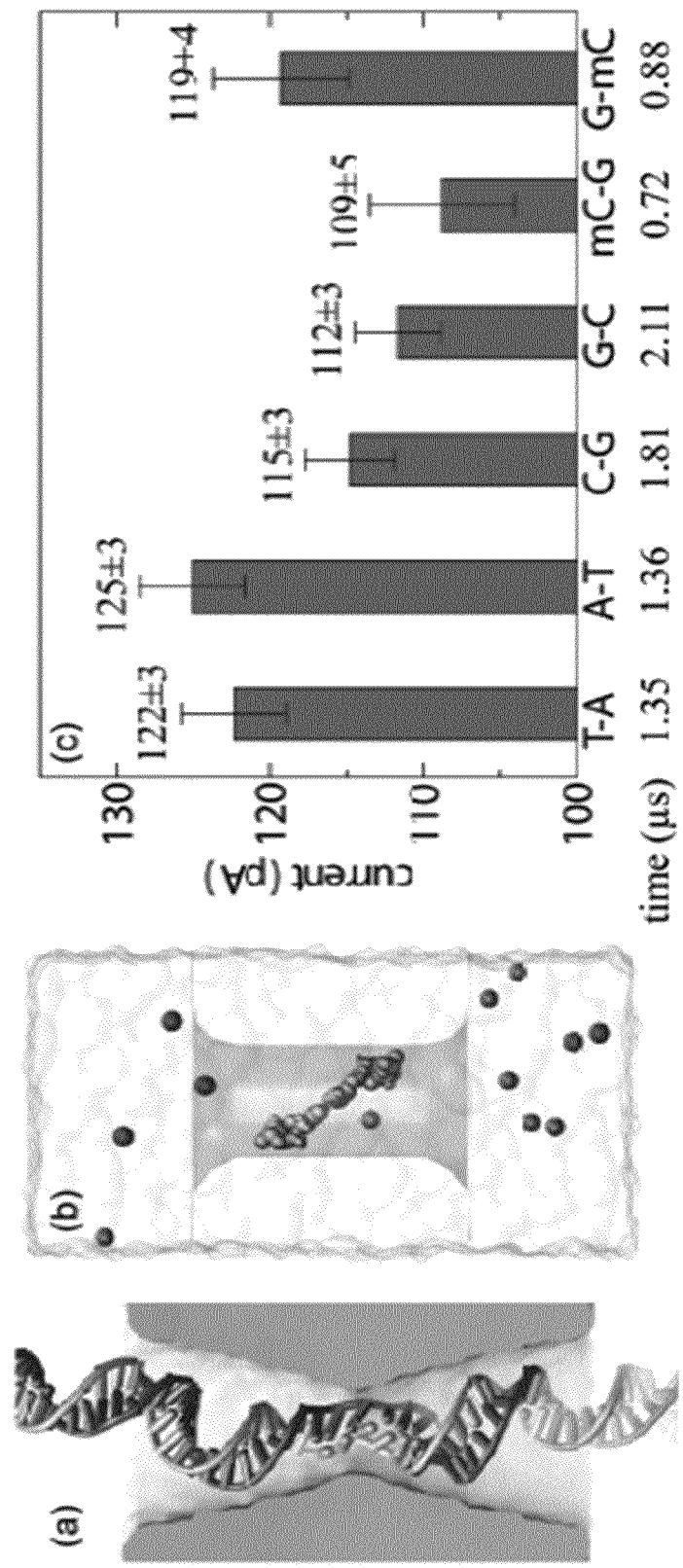
FIG. 8: Sequencing dsDNA by measuring the ionic current. (a) A snapshot of dsDNA trapped in a 2.0-nm-diameter pore. The DNA preserved its canonical B-form structure outside the pore constriction, whereas in the constriction it is stretched. (b) Snapshot of a simulation system used to determine the sensitivity of the ionic current blockade to the type and orientation of the confined basepair. A phantom nanopore of a 1.9 nm diameter and a 0.1M KCl solution is used for these simulations. (c) The simulated values of the ionic current for each basepair system under an effective bias of 750 mV with a pore current, I0=195.0±5.2 pA (estimated from a 717.4 ns simulation). The error bars show the standard errors of the average currents. The total simulation time for each system is specified in the bottom row. (d) Table of absolute valies of the current computed at 0.1M and 1.4M KCl salt concentrations.

We expect that, in a d=2.0 nm pore, the conformation of the trapped DNA molecule will resemble that shown in FIG. 8($a$) with the stretching exaggerated by the narrower constriction. Such a trap is used as part of a sequencing protocol whereby the translocation kinetics of dsDNA in a pore is stringently controlled and measurements can then be performed, taking the time necessary to extract information from the pore current about the identities of the nucleotides in the constriction. A concern with sequencing dsDNA in this manner is determining which nucleotide is on which strand, e.g. distinguishing A-T from T-A. However, our simulations show that the orientation of the basepair tilt, caused by the confinement, is maintained during translocation with the nucleotides of one strand always lagging their partners on the other. It is, therefore, possible to determine the sequence of dsDNA without ambiguities between A-T and T-A or G-C and C-G. Two properties of the trapped dsDNA make sequencing possible. First, the ions passing through the pore are forced to come in contact with nucleotides in the constriction. Second, because trapping the DNA allows current data to be acquired over long time intervals while the same nucleotides are held near the constriction, the sequence-dependent current values can be averaged for accuracy. For sufficiently low biases, the electric potential of the nucleotides presents an energy barrier to the passage of ions. Because the passage rate is exponentially related to the height of these barriers, differences in the heights for different sequences can have substantial effects on the I-V characteristics.

To demonstrate the feasibility of distinguishing trapped DNA nucleotides by measuring the ionic current, six systems containing single T-A, A-T, C-G, G-C, mC-G, and G-mC bps are each simulated using a combination of MD and Brownian dynamics. Here, X-Y denotes a system in which a cation passing through the nanopore along the direction of the electric field encounters nucleotide X first; mC denotes methylated cytosine. In our setup shown in FIG. 8(b), the reversing bias is equivalent to replacing an X-Y basepair with Y-X. FIG. 8(c) shows the absolute values of the current computed from these simulations. We find that systems containing A and T have significantly different values of ionic current than those containing G and C. Moreover, pairs with the same chemical makeup, but different orientations are distinguishable by the value of the blocked current (for example, mC-G and G-mC). The accuracy of the measurement increases as a square root of the number of translocated ions and, given sufficient averaging time, all combinations of the nucleotides should be distinguishable. Hence, our simulations demonstrate the feasibility of distinguishing the identity of tilted basepairs confined in a nanopore by measuring the pore current. This is supported by the observation of a signal attributed to base-pairs slowly translocating through a 2.5 nm pore shown in FIG. 6(c). The separation in current between A-T and C-G, which is $\Delta I=9.4$ pA in FIG. 6(b) is smaller than the prediction (13 pA) for a 2 nm pore, but the trap is also weaker.

In summary, this example demonstrates sequencing dsDNA in a nanopore with a diameter smaller than the double helix. The electric field, in combination with the size of the pore, induce a stretching transition in the constriction that facilitates control of both the molecular configuration and the translocation kinetics at the same time. Thus, high fidelity reads are possible since control of the molecular configuration (base-pair tilt) determines how the ions passing through the pore come into contact with the nucleotides in the constriction, while the translocation kinetics affect the time interval in which the same nucleotides are held in the constriction and data is acquired. MD simulations, extrapolated from our experiments, indicate that to discriminate between A-T and T-A base-pairs on dsDNA, we demand at minimum that $\Delta I \sim 3$ pA for a 2.0 nm pore (in 100 mM KCl). (This signal is not optimized: e.g. it seems likely that the signal will be larger with increased electrolyte concentration and a slit geometry). Therefore, for signal-to-noise >2, we need peak-to-peak noise <1.5 pA or an rms value of Irms~1.5 pA/8=0.2 pA. If dielectric noise associated with the capacitance predominates, then where D is the dielectric loss constant (D~0.2 for our membranes). For a bandwidth $\Delta f \sim 1$ kHz, we estimate that $DC_m \sim 1$ pF is required to discriminate between base-pairs, which is a factor 10× smaller than the typical membrane capacitance. On the other hand, a $1000 genome, corresponds to an estimated throughput of 330,000 bp/sec, which translates to a capacitance of 10 fF for the same noise power specification. A 10 fF parallel plate capacitance in a 10 nm thick silicon nitride would have an area of about 1 µm×1 µm, which is accessible with current semiconductor microfabrication technology. Improvements in the signal may also be achieved using a nano-slit geometry to force the current closer to the nucleotides by leveraging recent improvements in TEM technology.

Example 2

Base Discrimination

It is now possible to trap a single molecule of double-stranded DNA (dsDNA), by stretching it using a nanopore, smaller in diameter than the double helix, in a solid-state membrane. By applying an electric force larger than the threshold for stretching, dsDNA can be impelled through the pore. Once a current blockade associated with a translocating molecule is detected, the electric field in the pore is switched in an interval less than the translocation time to a value below the threshold for stretching. This leaves the dsDNA stretched in the pore constriction with the base-pairs tilted, while the B-form canonical structure is preserved outside the pore. In this configuration, the translocation velocity is substantially reduced from 1 bp/10 ns to ~1 bp/2 ms in the extreme, which facilitates high fidelity reads, allowing us to discriminate between A-T and C-G base-pairs. Using Molecular Dynamics simulations to extrapolate to smaller diameters and higher salt concentration, we find that it is possible to distinguish all of the trapped dsDNA base-pairs by simply measuring the current. Further optimizing conditions permits the dsDNA sequence to be determined without ambiguities between A-T and T-A or G-C and C-G from the stretched base-pair in the trapped configuration. The difference between C-G and A-T base-pairs can be resolved in this case because of the longer (~2 ms) time each base-pair spends in the constriction.

This assertion is corroborated by even longer duration measurements of blockade currents associated with streptavidin bound, 100 bp long, C-G and A-T biotinylated duplexes trapped by the electric field in a pore in a configuration represented schematically in FIG. 9(a). Streptavidin has an extraordinary affinity for biotin, which we leverage to measure the blockade current for a trapped biotin-DNA duplex in a 2.5×2.3±0.2 nm pore (U=0.17±0.04V from λ-DNA blockade frequency) in a 23.1±2.0 nm thick membrane immersed in 1M KCl for transmembrane biases ranging from 200 mV to 1V. At low voltage, the duration of a blockade is interminable—the blockade ends only if the voltage is manually reversed and the dsDNA is impelled out of the pore, streptavidin and all. However, the dwell time is an exponentially decreasing function of the applied voltage as illustrated in FIG. 9(b). Nevertheless, the duration of a blockade can still exceed 10 s even at a transmembrane bias of 1V, which is extraordinary (23) and suggests that the load derived from the electric force on the trapped DNA may sometimes be shared between the membrane and the biotin-streptavidin bond. (DNA binding to the membrane could be attributed to salt-induced absorption on silica in the nitride(24).) However, neither the dwell time distribution nor the voltage dependence seems to depend on C-G or A-T variants. The distribution of dwell times observed at 1V is shown in FIG. 9(c) for both DNA variants.

Figure 9:
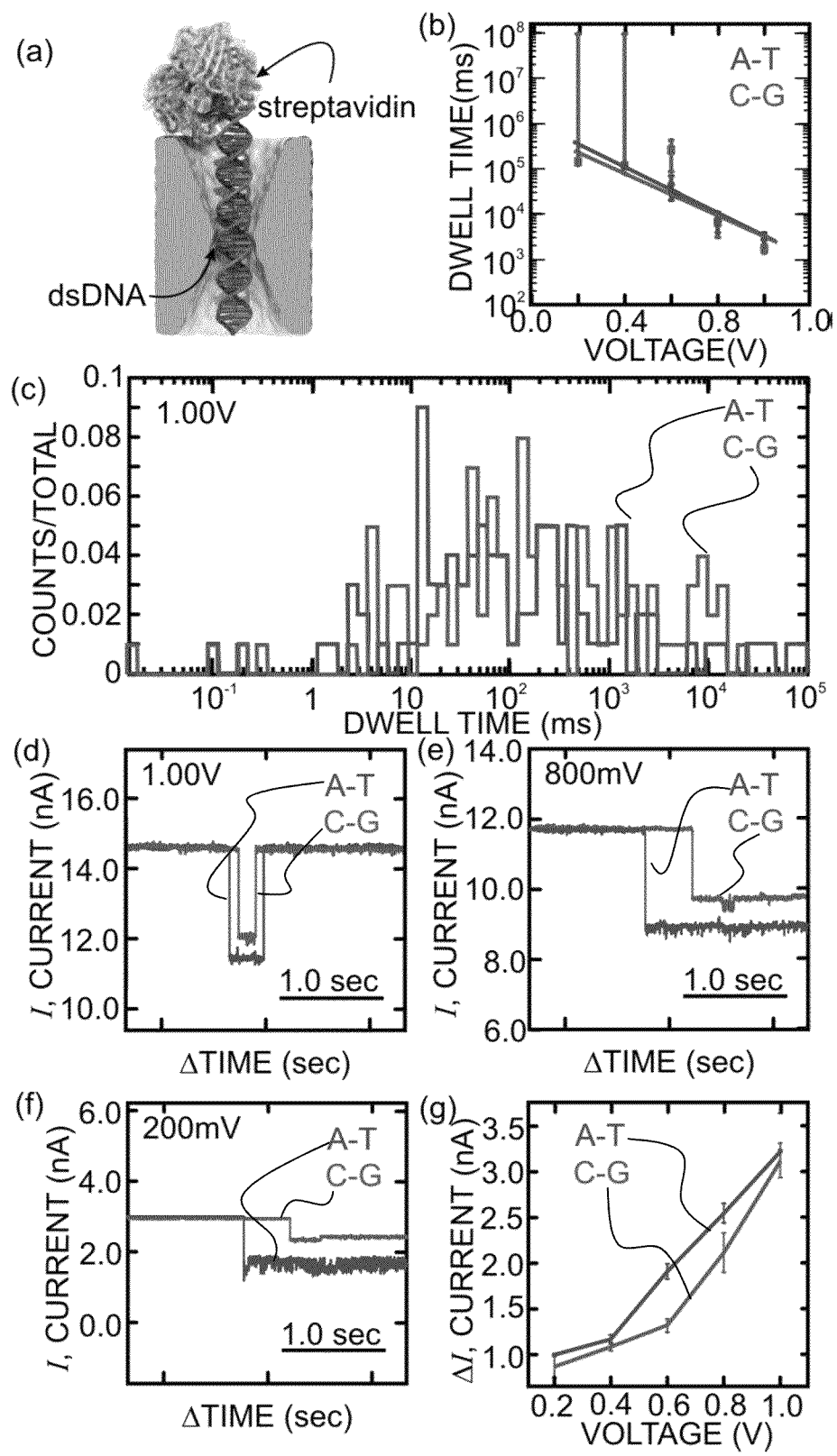
FIG. 9 Streptavidin bound biotin DNA duplex trapped by the electric field in a nanopore. (a) Model of biotinylated dsDNA bound to streptavidin in a 2.6 nm×2.1 nm cross-section pore in a 23 nm thick membrane. The molecular conformation is stretched in the constriction beyond the 0.34 nm about 8-20%, depending on the applied voltage. (b) The dependence of the peak dwell time for both C-G and A-T duplexes on the membrane voltage at high salt, 1M KCl. (c) The distribution of dwell times inferred from the blockade current for both C-G and A-T duplexes measured for streptavidin bound biotin DNA at 1V. The residence time in the pore is extraordinarily long even at high voltage. (d,e,f) Current blockades measured at 1V, 0.8V and 0.2V transmembrane bias in 1M KCl in a 2.6×2.1 nm pore associated with C-G and A-T duplexes biotinylated to streptavidin. The difference in blockade current can be used to discriminate C-G from A-T. (g). Summary of the difference between the open pore current and the blockade current measured for C-G and A-T duplexes at 1M KCl.

In our analysis of the blockades due to the two variants, C-G and A-T, we focus on dwell times at the peak of the distribution or longer and on traces with essentially the same open pore current measured after intervening flushes and cleans. FIGS. 9(d-f) show typical current blockades for observed at 1V for the peak in the dwell time distribution, and at 0.8V and 200 mV for dwell times >10 sec, respectively. Clearly, it is easy to discriminate C-G base-pairs stretched in the pore from the smaller blockade current associated with either A-T—the difference is 533±98 pA at a transmembrane bias of 1V, 789±57 pA at 800 mV and 323±83 pA at 200 mV. FIG. 9(g) summarizes the differences between the blockades associated with the two dsDNA variants and open pore current for the same pore as a function of transmembrane bias. This summarizes events observed with an open pore current of I0=2994±51 pA at 200 mV; I0=6134±72 pA at 400 mV; 8174±728 pA at 600 mV; I0=11.909±0.259 nA at 800 mV; and I0=14.785±0.203 pA at 1V. It seems that C-G can easily be discriminated from A-T under these conditions over a range of voltage. Apparently, the increase in molarity (10×) and larger voltage (10×) exaggerate the effect of stretching on the blockade current. This must be the case since larger pore diameter 3.5×2.4±0.2 nm does not reveal a difference between C-G and A-T beyond for the same salt in the same voltage range. However, high salt may not be an optimal electrolyte for sequencing long DNA strands if λ-DNA is absorbed onto the membrane for 1M KCl and remains trapped in the pore indefinitely over hrs.

Figure 10:
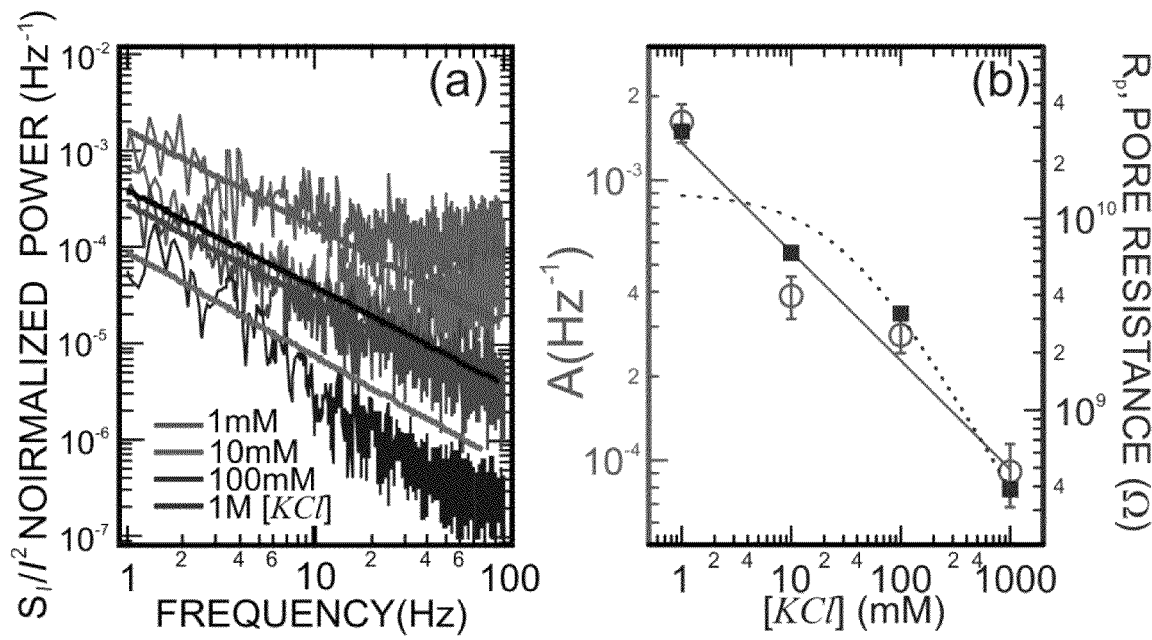
FIG. 10 shows the dependence of the coefficient A measured in a pore with a 2.4±0.2 nm diameter in a 12 nm thick nitride membrane.

Detailed modeling of DNA translocation: As illustrated in FIG. 4(c), we find that the noise spectrum <100 Hz is sensitive to the electrolyte concentration while the high frequency (>100 Hz) noise is not. Hooge suggested that I/f noise occurs in bulk conductors due to the fluctuating mobility of charge carriers that produces current fluctuations. In contrast, there are surface models in which charge traps located on the pore surface have a fluctuating charge state that affects the ionic current and likewise exhibits a 1/f characteristic. The two models can be differentiated by the dependence on the coefficient A on the pore conductance. FIG. 10 shows the dependence of the coefficient A measured in a pore with a 2.4±0.2 nm diameter in a 12 nm thick nitride membrane: the resistance follows a A~$R_p^\gamma$ law with γ=1.06±0.15. Generally, we find that γ=1.03±0.44 over a factor of 10,000× in pore resistance, in support of Hooge's phenomenological picture.

Thus, reducing parasitic capacitances, electrolyte resistance and amplifier noise are all key elements for improving both the frequency and noise performance. From the close correspondence between our models and the measurements of the frequency response, we assert that this can be accomplished by either: 1. using a composite membrane consisting of polyimide and silicon nitride layers to reduce the effect of parasitic elements such as the depletion layer in the substrate; 2. replacing the silicon handle wafer altogether with a dielectric substrate; 3. using Ag/AgCl electrode positioned within microns of the pore; or eliminating the cable capacitance. For example, FIG. 4(e) explicitly shows the improvement in the signal to noise ratio that can be gleaned by using a composite polyimide-nitride membrane. The figure compares a current blockade associated with a single λ-DNA translocating through a d=3.0±0.2 nm pore in a 30 nm thick nitride membrane 50 □m×50 □m in area with a pore of the same diameter in the same type of membrane but with a polyimide layer 3.6 □m thick coating it, reducing the exposed area to 10 □m. We observe a substantial reduction in the peak-to-peak noise in both the open and blockade pore current (62 pA to 20 pA), which will facilitates signal extraction.

Figure 11:
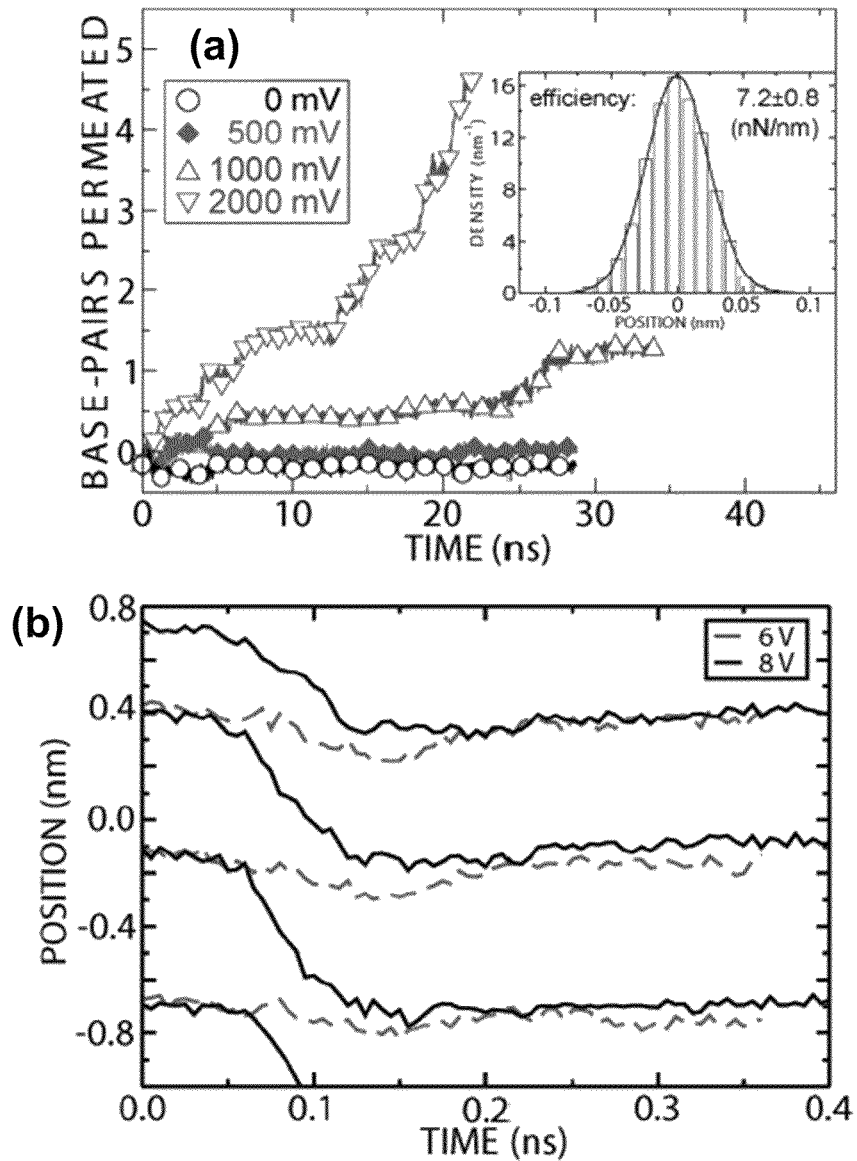
FIG. 11 (a) The number of base-pairs permeating through a nanopore (2.0 nm diameter) (compare against the larger 2.6 nm×2.1 nm-cross section pore of FIG. 7(b)) in four MD simulations carried out at different biases. The simulations predict a voltage threshold between 0.5V and 1.0V. (Inset) Histogram of the displacement of the base-pair nearest to the membrane's center at a 0V bias. The solid line shows the distribution expected for a harmonic trap with a 6.6 nN/nm spring constant. (b) Stepwise advancement of dsDNA by a single base-pair in a 2 nm pore. The position of the nucleotides near the constriction are plotted versus time. In these simulations, a half-sine voltage pulse was applied from 0.0 to 0.2 ns with amplitudes of 6 and 8 V. At 6 V there is a small displacement of the nucleotide during the application of the pulse, after which the nucleotide returns to its initial position. However, at 8V the molecule translates so that the final position of the nucleotides near the center of the pore are near the initial positions of the nucleotide directly below, constituting a nucleotide step.

MD confirms our understanding of the mechanism of this process, indicating: (i) the motion of the dsDNA can be effectively stopped when the driving voltage is turned off; and (ii) it is feasible to distinguish trapped DNA base-pairs through simple current measurements. FIGS. 7 and 11 illustrate two simulated systems, which include fragments of dsDNA, 100 mM KCl, and pores having 2.6 nm×2.1 nm (FIG. 7) and 2.0×2.0 nm (FIG. 11) cross-sections. The molecular conformation within the 2.6 nm×2.1 nm pore shown in FIG. 7(a) is stretched by about 8-20%. As illustrated in FIG. 7(b), at 250 and 500 mV, the dsDNA's motion in the pore is arrested following a small initial displacement allowed by stretching. Only when a bias of 1V is applied is dsDNA transport observed. By analyzing dsDNA's displacements at 0V (shown as inset to FIG. 7(b)), we determine that the pore acts as a harmonic trap with an effective spring constant of k=3.0±0.8 nN/nm. A similar analysis for the 2 nm pore shown in (see FIG. 11) indicates still larger distortions in the stretched DNA. The base-pair rise increases from 0.34 nm to 0.41 nm at 0V; due to a trap with k=7.2±0.8 nN/nm. (For a d=1.6 nm, the spring constant is even higher: k=19.69±0.06 nN/nm.)

As shown in FIGS. 7(b) and 11(b), MD reveals that a constant applied voltage of 0.5V is insufficient to restart translocation in a pore with a diameter smaller than the double helix. However, the DNA moves in the direction of the applied electric force when 1.0V is applied. Therefore, a threshold voltage exists between 0.5 and 1.0V. The probability of an escape from a trap depends sharply on the force applied to the molecule, explaining the thresholds. The force required to restart the motion is essentially determined by the product of the spring constant, k, and the separation between bases x0, which we estimate to be about 0.48 nN, 1.5 nN and 4.1 nN for the 2.6, 2.0 and 1.6 nm pores respectively.

Based on these observations, we have developed a strategy to control the translocation and ostensibly to trap bases at fixed positions within a pore indefinitely. Due to the periodicity of dsDNA, we find that the translocation through an undersized pore can proceed in discrete steps in response to a very high-speed voltage pulse. FIG. 13(e) shows DNA nucleotides near the pore constriction during and after the application of a half-sine voltage pulse with a duration of 0.2 ns and amplitudes of 6 and 8V. For the 6V pulse, the nucleotides are displaced slightly (0-0.2 ns), but return to their original positions after it subsides. On the other hand, the 8V pulse causes a single base-pair step so that the final position of the base-pair is near the initial position of the base-pair directly below it. Thus, we find a tendency for the portion of the molecule near the constriction to translate in discrete steps, so that the pore can be used as a turnstile stepping base-pairs one at a time by applying voltage pulses. These simulations clearly demonstrate that stepping DNA in a d<2.5 nm pore is feasible, provided the voltage can be switched fast enough.

This type of trap process can be used in a sequencing protocol whereby the translocation kinetics of dsDNA in a pore are stringently controlled and measurements are performed to extract the identities of the nucleotides from the pore current. One difficulty with sequencing this way is determining which nucleotide is on which strand, e.g. distinguishing A-T from T-A. However, our in silico experiments show that the base-pair tilt, caused by the confinement, is maintained during a translocation with the nucleotides of one strand always lagging their partners on the other. At low bias, the electric potential of the nucleotides in the tilted configuration presents a peculiar energy barrier to the ions with a passage rate that is exponentially related to the height. The differences in heights for different sequences should therefore have substantial effects on the current.

To demonstrate the feasibility of distinguishing the nucleotides by measuring the current, pores containing single T-A, A-T, C-G, and G-C base-pairs were each simulated as illustrated in FIG. 8. Here, X-Y denotes a system in which a cation passing through the pore along the direction of the electric field encounters nucleotide X first. Due to the symmetry of the setup, a reverse bias is equivalent to replacing X-Y with Y-X. The table shown in FIG. 8(d) shows the absolute values of the current computed at salt concentrations of 100 mM and 1.4M KCl. In the first two rows for each concentration, we have combined the current values for the base-pairs containing T and A, and the base-pairs containing C and G to highlight the fact that these could be clearly discriminated. We find that the systems containing A and T have significantly different values of current than those containing G and C.

The simulated current blockades for single, tilted C-G and A-T base pairs do not match the sequence-dependent blockades measured using streptavidin-DNA constructs and we don't expect they should. We attribute this discrepancy to the difference in the conformations of DNA and to the protein over the pore. In the measurement, streptavidin anchors a dsDNA molecule in the pore constriction. We have previously shown the protein in this configuration can markedly affect the pore current—even causing enhancements above the open pore value. Moreover, under the influence of the applied field, dsDNA can stretch in a sequence-dependent way altering the pore volume available for ion conductance. Sensitive to this effect, the measurements show a difference between blockade currents produced by A-T and C-G strands. In contrast, MD shows the effect of single base-pairs on the ionic current blockade, assuming that the conformations of the base pairs in the pore are the same. Through a combination of MD and BD simulations, we expect to reproduce the sequence-specific ionic blockades measured with streptavidin.

To obtain a more accurate estimate of the ionic current and allow for broader exploration of conditions to optimize base-pair discrimination, we have developed a BD model of the nanopore system with the interactions derived from all-atom MD simulations. By modeling water implicitly and using a much larger timestep than can be used in all-atom MD simulations, the BD simulations show a $10^4$-$10^5$-fold increase in performance. BD simulations of the pore current have been done before.[62-64] However, in contrast to these studies, advances in computing power allow us to derive all the parameters of the BD simulations from all-atom MD simulations. To do this, we make use of umbrella sampling and the WHAM method to obtain the potential of mean force (PMF) functions for the interactions. Our BD model takes three types of input: (i) PMF functions that model the interaction between all pairs of ion types, (ii) 3D PMF maps that model the environment (including the solution, the pore, and the DNA) for each type of ion and each DNA basepair, and (iii) 3D maps of the diffusivity for each type of ion.

Figure 12:
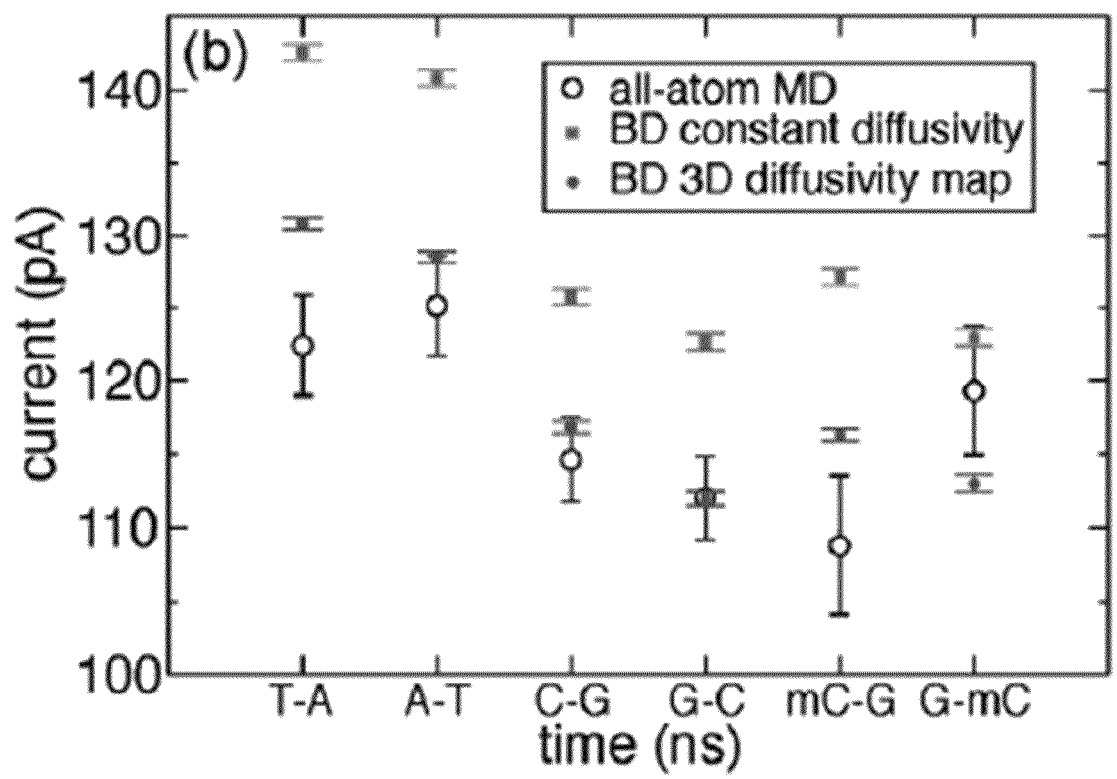
FIG. 12 Sub-millisecond simulations of ionic current blockades using atomically precise Brownian Dynamics (BD). The simulated ionic current using microsecond all-atom and 100-microsecond BD trajectories is platted as a function of base-pair type, with X-Y and Y-X indicating bases on different strands. mC-G denotes methylated cytosine. The much greater efficiency of the BD simulations allows for much longer runs and therefore much smaller error bars at a fraction of the computational cost.

Generating the PMF functions for interactions between the ions via the WHAM method involved performing many MD simulations with the distance between the ions restrained to a different value for each simulation. Likewise, generating the 3D PMF maps required restraining ions to different positions on a 3D hcp lattice around the pore and DNA basepair. All these PMF functions implicitly include the mean effect of water molecules. The diffusivity maps are computed from these same simulations using the velocity correlation functions. To validate our BD model, we simulate with the same parameters used in the all-atom MD simulations above and compared the ionic currents. For the pore containing no base-pair at 100 mM KCl we obtain a current of 193.0±0.45 pA for a 96 µs BD simulation, consistent with the MD value. FIG. 12 compares the pore currents for single base-pairs. For these systems, including position-dependent diffusivity in the model is crucial to obtaining quantitative agreement between the BD and MD simulations. The BD simulations permit us to obtain results in hours that we could not obtain in weeks of all-atom MD simulations. As shown in FIG. 12, we have demonstrated the feasibility of distinguishing base-pairs of the same chemical structure but different orientations, T-A can be easily distinguished from A-T and C-G can be readily distinguished from G-C.

Figure 13:
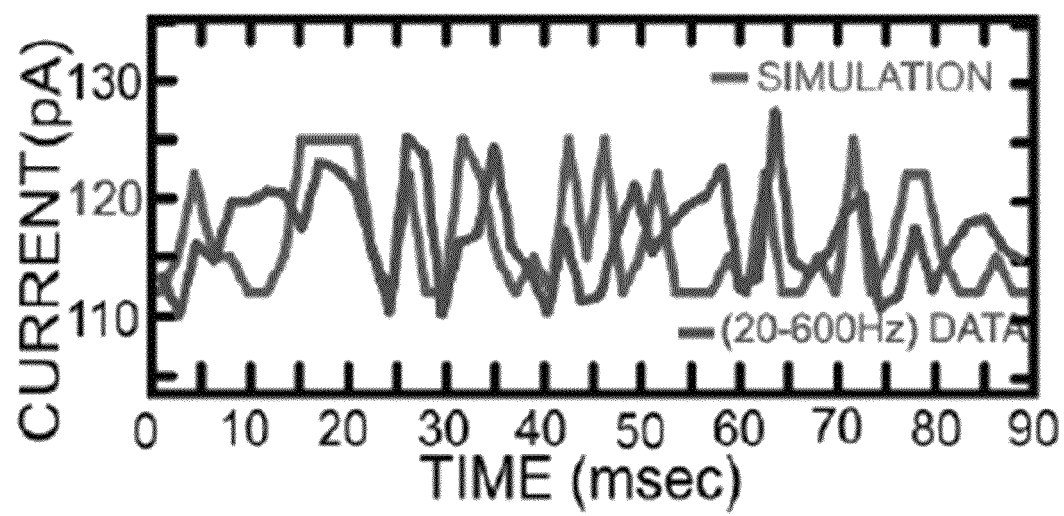
FIG. 13: Magnified view of blockade current measured near 58.8 s superimposed on a current trace comprised of the simulated current response estimated from the results in FIG. 12 for the last 50 bp of the 3' end of λ-DNA. The correlation coefficient between the measurement and the simulation is 0.31.
Figure 14:
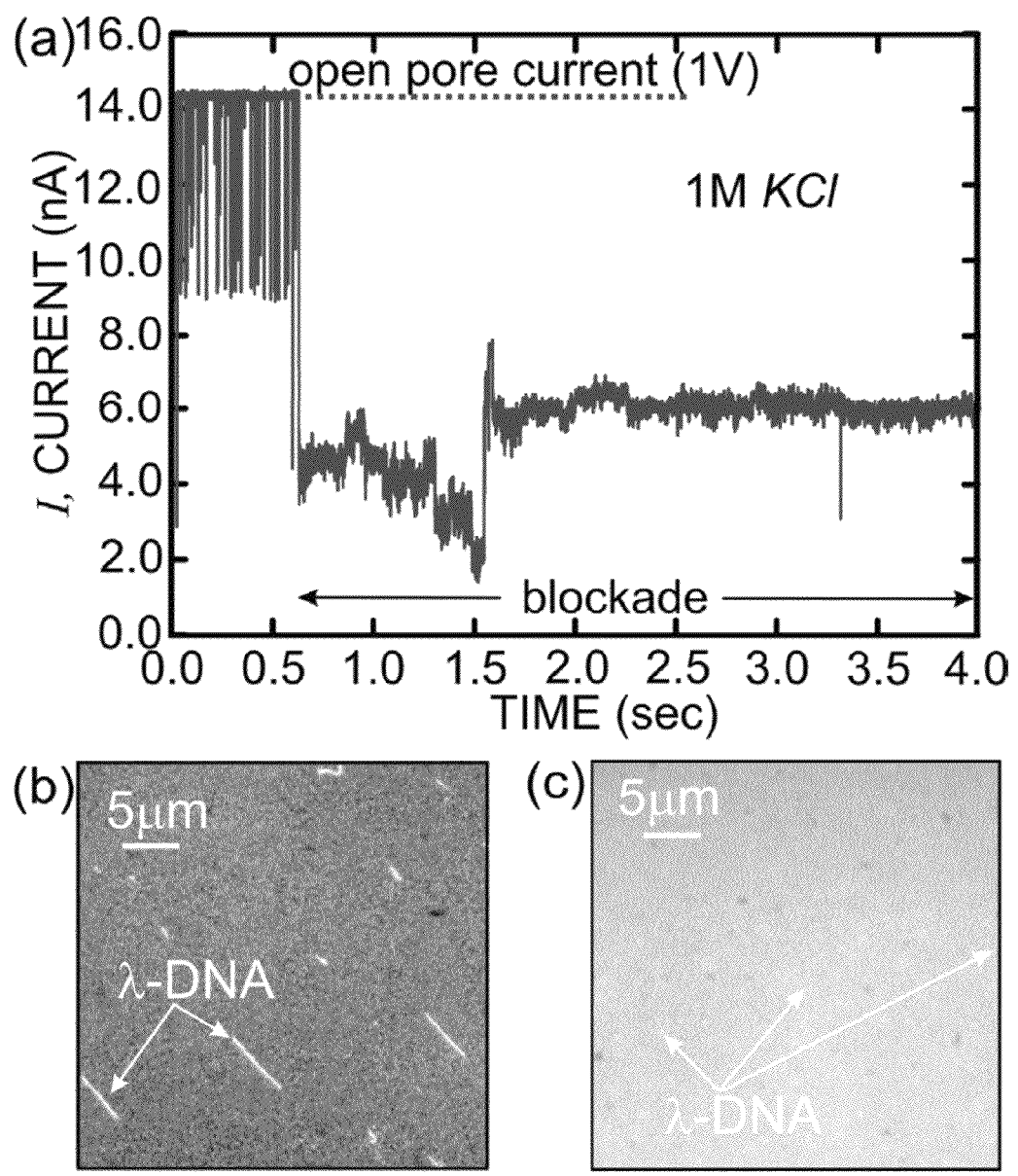
FIG. 14(a): Current blockades associated with λ-DNA measured at 1V in a high salt concentration (1M KCl) in a 2.6×2.1 nm cross-section pore in a 23 nm thick membrane. Near 0.6 s the DNA sticks to the pore. (b,c) Single molecule fluorescence of λ-DNA intercalated with YOYO fluorescent dye in high salt (1M KCl). The DNA is absorbed on silica (b), but not on silicon nitride membranes (c).

Finally, FIG. 13 illustrates the coincidence between this naive model of the pore current derived from the MD results of FIG. 12 for a single base-pair trapped in the constriction and the measurements obtained near 58.8 sec, just before the molecule exits the pore, assuming a uniform translocation velocity of 1 bp/2 ms. The current trace is extracted at the end of the blockade, which should amount to approximately the last 50 bps, and then compared with the corresponding sequence (from 48453-48502 bp) associated with the 3' end of λ-DNA. There is an offset in the current between the two traces of 117 pA, since neither the voltage nor the pore diameter used to extract the values used in the model coincide with the measurement. The correlation between the measurement and simulation is 0.31, which potentially indicates a lack of signal-to-noise required for sequencing with single base resolution or a non-uniform translocation velocity. However, this correspondence indicates the prospects for sequencing with single base resolution and provides a target to exceed through optimization of the pore geometry and electrolyte.

Optimization of the Pore and Electrolyte for Sequencing.

While both simulation and measurements indicate high electrolyte concentration for improved signal fidelity, high salt may not be an optimal for sequencing long DNA strands. We observed that at high salt concentration (1M KCl) λ-DNA adheres to the pore even at high transmembrane bias; apparently it is absorbed onto the membrane and it remains there for hours. A typical example is illustrated in FIG. 13(a) with a constant 1V transmembrane bias applied. While short duration (with a typical duration of ~6.8 ms) current blockades with $\Delta I/I0$~0.36 can be observed in the interval from 0-0.5 s, we also find an extended blockade event with $\Delta I/I0$>0.62, starting near 0.6 s, that persists interminably. We attribute the blockade to one or more dsDNA bound to the membrane in the pore. To alleviate this sticking we can use shorter strands or lower molarity electrolyte, higher or lower pH, and thinner membranes. On the other hand, the sticking frequency seems to increase with the DNA concentration, the salt concentration and if a divalent electrolyte such as $CaCl2$ is used in place of KCl.

Salt-induced absorption on silica is one of the most common methods for extracting DNA from cell homogenates and it is consistent with the observations we have made about the sticking conditions in a pore in a nitride membrane: i.e. DNA sticks at high molarity, but not at dilute concentrations. Although the mechanism is not understood, it is supposed that a high electrolyte concentration disrupts the shell of hydration around the DNA allowing a positively charged ion to form a salt bridge between the negatively charged silica and the negatively charged DNA backbone. We attribute the observation of the interminably trapped dsDNA to binding to oxide in a pore that is likely formed after sputtering exposure to air and/or electrolyte or surface treatments such as a O2 plasma or piranha clean. After plasma cleaning, CVD silicon nitride films seem to show high oxygen to silicon ratio (0.55), indicating severe oxidation, while the carbon content decreases and the silicon to nitrogen ratio increases (from 0.73 to 1.23.) according to XPS.

FIGS. 13(b,c) show a test of single molecule fluorescence obtained from DNA duplexes intercalated with YOYO-1 (a dimeric cyanine fluorescent dye) fluorochromes adsorbed onto a silanized silica coverslip and silicon nitride membrane in 1M KCl. The DNA molecules are first stained with YOYO 1 at a ratio of DNA base pairs to YOYO-1 molecules of 10:1 and diluted to 1.67 nM (in 1M KCl). Subsequently, the coverslips were cleaned using an O2 plasma (we also tested ethanol and H2SO4:H2O2 treatments and saw no difference) and then bonded them with a microfluidic, and subsequently immersed it a 1M KCl electrolyte containing the DNA. YOYO emits at 510 nm when excited with 457 nm wavelength. The fluorescence was observed using a Zeiss Axio-Observer inverted microscope with an Achroplan 100× oil immersion objective (1.3NA) equipped with a $1024 \times 10^{24}$ EMCCD camera (Andor, DU-888) operated at −70° C. The fluorescence channel is defined by excitation filter 438/24 nm center wavelength/bandwidth, dichroic mirror with 458 nm edge wavelength, emission filter at emission 483/32 nm. The excitation is provided by EXFO X-Cite 120 metal halide lamp operated at 12% iris. We clearly observe DNA sticking to the silica in FIG. 13(b), while we find a dearth of DNA sticking to the nitride membrane (the fluorescent DNA can be seen hovering near positions indicated by the arrows) treated with the same conditions as shown in FIG. 13(c). These data counter-indicates the use of high salt and silicon oxide surfaces for sequencing long DNA strands, and while nitride membrane seems more optimal than oxide, the concentration of dsDNA and electrolyte have to be optimized to avoid absorption in the pore where the surface to volume ratio is very high while still providing adequate signal.

STATEMENTS REGARDING INCORPORATION BY REFERENCE AND VARIATIONS

All references throughout this application, for example patent documents including issued or granted patents or equivalents; Patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). This application is related to U.S. Provisional Patent Application No. 61/139,056 filed Dec. 19, 2008 titled "Detecting and Sorting Methylated DNA using a Synthetic Nanopore", from which PCT Pub. No. WO 2010/080617 (GS 168-08) claims benefit, each of which is hereby incorporated by reference to the extent not inconsistent herewith.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a size or distance range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

Selected parameters for the model shown in FIG. 3(h) used to fit the measurements of three membranes shown in FIG. 3(g).

| Model parameters | 12 nm nitride 50 µm × 50 µm | Imide/ 30 nm nitride 10 µm × 10 µm | 200 nm nitride 500 µm × 500 µm |
|---|---|---|---|
| Rel Electrolyte Res. (kΩ) | 0.85 | 0.61 | 0.9 |
| Fdlt1 Top double layer Faradaic Coeff.(kΩ) | $2.80 \times 10^7$ | $7.30 \times 10^6$ | $4.00 \times 10^6$ |
| Cdlt1 Top double layer Cap. (pF) | 303000 | 303000 | 184000 |

TABLE 1-continued

Selected parameters for the model shown in FIG. 3(h) used to fit the measurements of three membranes shown in FIG. 3(g).

| Model parameters | 12 nm nitride 50 μm × 50 μm | Imide/ 30 nm nitride 10 μm × 10 μm | 200 nm nitride 500 μm × 500 μm |
|---|---|---|---|
| Rim1 Polyimide Res. (GΩ) | n/a | 122 | n/a |
| Cim1 Polyimide Cap. (pF) | n/a | 18.3 | n/a |
| Rmem1 Si3N4 Res. (GΩ) | 795 | 1600 | 3890 |
| Cmem1 Si3N4 Cap. (pF) | 1520 | 727 | 150 |
| Rdt Top depletion region Res. (kΩ) | 22.7 | 22.7 | 91.2 |
| Cdt Top depletion region Cap. (pF) | 308 | 308 | 46.7 |
| Rsi Si Res. (Ω) | 25 | 25 | 21.8 |
| Rdb Bottom depletion region Res. (kΩ) | 706 | 706 | 800 |
| Cdb Bottom depletion region Cap. (pF) | 895 | 399 | 300 |
| Rim2 Polyimide Res. (GΩ) | n/a | 1410 | n/a |
| Cim2 Polyimide Cap. (pF) | n/a | 0.007 | n/a |
| Rmem2 Si3N4 Res. (GΩ) | n/a | 15000 | n/a |
| Cmem2 Si3N4 Cap. (pF) | n/a | 3.7 | n/a |
| Cmem3 Si3N4 Cap. (pF) | 8.1 | 0.08 | 169 |

TABLE 2

References

1. D. Branton, D. W. Deamer, A. Marziali, H. Bayley, et al., "The potential and challenges of nanopore sequencing," *Nature biotechnology*, 26(10), 1146-1153 (2008).
2. J. B. Heng, A. Aksimentiev, C. Ho, P. Marks, Y. V. Grinkova, S. Sligar, K. Schulten, and G. Timp, "The Electromechanics of DNA in a Synthetic Nanopore," *Biophys. J.*, 90: 1098-1106 (2006).
3. J. B. Heng, A. Aksimentiev, C. Ho, P. Marks, Y. V. Grinkova, S. Sligar, K. Schulten, and G. Timp, "Stretching DNA using the Electric Field in a Synthetic Nanopore," *NanoLet.*, 5(10): 1883-1888 (2005).
4. U. Mirsaidov, W. Timp, X. Zou, V. Dimitrov, K. Schulten, A. P. Feinberg, and G. Timp "Nanoelectromechanics of Methylated DNA in a Synthetic Nanopore," *Biophys. J. Lett.* 96(4) (2009).
5. U. Mirsaidov, V. Dimitrov, J. Comer, D. Wang, W. Timp, A. Aksimentiev, and G. Timp "Trapping a Double-Stranded DNA Molecule in a Nanopore and the Prospects for Sequencing It," *Proc. Natl. Acad. USA accepted for publication* (2009).
6.. E. S. Lander, L. M. Linton, B. Birren et al., "Initial sequencing and analysis of the human genome," *Nature*, 409, 6822, 860-921 (2001).
7. G. Bejerano, D. Haussler, and M. Blanchette, "Into the heart of darkness: large-scale clustering of human non-coding DNA," *Bioinformatics*, 20, 1, i40-8 (2004).
8. E. Birney, J. A. Stamatoyannopoulos, A. Dutta et al., "Identification and analysis of functional elements in 1% of the human genome by the ENCODE pilot project," *Nature*, 447, 7146, 799-816 (2007).
9. S. R. Gill, M. Pop, R. T. DeBoy et al., "Metagenomic analysis of the human distal gut microbiome," *Science*, 312, 5778, 1355-1359, (2006).
10. L. D. Wood, D. W. Parsons, S. Jones et al., "The Genomic Landscapes of Human Breast and Colorectal Cancers," *Science*, 318, 5853, 1108-1113 (2007).
11. J. G. Paez, P. A. Janne, J. C. Lee ef al., "EGFR mutations in lung cancer: Correlation with clinical response to gefitinib therapy," *Science*, 304, 5676, pp. 1497-1500 (2004).
12. D. S. Johnson, A. Mortazavi, R. M. Myers et al., "Genome-wide mapping of in vivo protein-DNA interactions," *Science*, 316, 5830,1497-1502 (2007).
13. A. Barski, S. Cuddapah, K. R. Cui et al., "High-resolution profiling of histone methylations in the human genome," *Cell*, 129, 4, 823-837 (2007).
14. P. Callinan, and A. Feinberg, "The emerging science of epigenomics," *Human Mol. Gen.*, 15, R95 (2006).
15. O. Morozova, and M. A. Marra, "Applications of next-generation sequencing technologies in functional genomics," *Genomics*, 92, 5, 255-264 (2008).
16. F. Sanger, S. Nicklen, and A. Coulson, "DNA Sequencing with Chain-Terminating Inhibitors," *Pro.c Nat. Acad. Sci*, 74,12, 5463-5467 (1977).
17. A. Marziali, and M. Akeson, "New DNA sequencing methods," *Ann Rev Biomed Eng*, 3, 195-223, 2001.
18. J. Shendure, R. Mitra, C. Varma et al., "Advanced sequencing technologies: methods and goals," *Nature Reviews Genetics*, 5, 5, 335-344 (2004).
19. E. R. Mardis, "The impact of next-generation sequencing technology on genetics," *Trends Genetics*, 24, 3, 133-141 (2008).
20. J. Kasianowicz, E. Brandin, D. Branton et al., "Characterization of individual polynucleotide molecules using a membrane channel," *Proceedings of the National Academy of Sciences*, 93, 24, 13770 (1996).
21. M. Akeson, D. Branton, J. J. Kasianowicz et al., "Microsecond Time-Scale Discrimination Among Segments Within Single RNA Molecules," *Biophys. J.*, 77, 6, 3227-3233 (1999).
22. Y. Astier, O. Braha, and H. Bayley, "Toward Single Molecule DNA Sequencing: Direct Identification of Ribonucleoside and Deoxyribonucleoside-Monophosphates by Using an Engineered Protein Nanopore Equipped with a Molecular Adapter," *J. Am. Chem. Soc.*, 128, 5, 1705 (2006).

TABLE 2-continued

References

23. J. Li, D. Stein, C. McMullan et al., "Ion-beam sculpting at nm-length scales," *Nature*, 412, 166 (2001).
24. Z. Siwy, and A. Fulinski, "Fabrication of a synthetic nanopore ion pump," *Phys. Rev. Lett.*, 89, 4, (2002).
25. A. J. Storm, J. H. Chen, X. S. Ling et al., "Fabrication of solid-state nanopores with single-nanometre precision," *Nature Materials*, 2, 8, 537-540 (2003).
26. J. B. Heng, C. Ho, et al., "Sizing DNA using a nanometer-diameter pore," *Biophys. J.*, 87, 4, 2905 (2004).
27. B. Luan and A. Aksimentiev, "Strain softening in stretched DNA," *Phys. Rev. Let.* 101(11) 118101 (2008).
28. U. F. Keyser, B. N. Koelemean, S. VanDorp, D. Krapf, R. M. Smeets, S. G. Lemay, N. H. Dekker and C. Dekker, "Direct Force Measurements of DNA in a Solid-State Nanopore," *Nature Phys.*, 2, 473 (2006).
29. D. Fologea, J. Uplinger, B. Thomas, D. S. McNabb, and J. L. Li, "Slowing DNA translocation in a solid-state nanopore," *Nano Lett.* 5(9): 1734-1737 (2005).
30. A. J. Storm, et al. "Fast DNA translocation through a solid-state nanopore," *Nano Lett.* 5(7): 1193 (2005).
31. R. Smeets, U. Keyser, N. Dekker et al., "Noise in solid-state nanopores," *Proc. Nat. Acad. Sci.*, 105, 2, 417 (2008).
1. J. Shendure, R. Mitra, C. Varma et al., "Advanced sequencing technologies: methods and goals," *Nature Reviews Genetics*, 5, 5, 335-344 (2004).
2. E. R. Mardis, "The impact of next-generation sequencing technology on genetics," *Trends Genetics*, 24, 3, 133-141 (2008).
3. D. Branton, D. W. Deamer, A. Marziali, H. Bayley, et al., "The potential and challenges of nanopore sequencing," *Nature biotechnology*, 26(10), 1146-1153 (2008).
4. U. Mirsaidov, D. Wang, J. Comer, W. Timp, V. Dimitrov, J. Shim, A. Aksimentiev, and G. Timp "Trapping a Double-Stranded DNA Molecule in a Nanopore and the Prospects for Sequencing It," *Proc. Natl. Acad. USA, in review* (2009).
5. V. Dimitrov, U. Mirsaidov, D. Wang, T. Sorsch, W. Mansfield, J. Miner, F. Klemens, R. Cirelli, S. Yemenicioglu, and G. Timp, "Nanopores in Solid-State Membranes Engineered for Single-Molecule Detection," *Nanotechnology* accepted for publication (2010).
6. K. Schulten, J. C. Phillips, L. V. Kalé, and A. Bhatele, "Biomolecular modeling in the era of petascale computing, in David Bader, editor, *Petascale Computing: Algorithms and Applications*, pp. 165-181, Chapman and Hall/CRC Press, Taylor and Francis Group, New York (2008).
7. J. C. Phillips, R. Braun, W. Wang, J. Gumbart, E. Tajkhorshid, E. Villa, C. Chipot, R. D. Skeel, L. Kale, and K. Schulten, "Scalable molecular dynamics with NAMD," *J Comp. Chem*, 26: 1781-1802 (2005).
8. F. Sanger, S. Nicklen, and A. Coulson, "DNA Sequencing with Chain-Terminating Inhibitors," *Proc. Nat. Acad. Sci*, 74, 12, 5463-5467 (1977).
9. E. S. Lander, L. M. Linton, B. Birren et al., "Initial sequencing and analysis of the human genome," *Nature*, 409, 6822, 860-921 (2001).
10. J. C. Venter JC, M. D., Adams, E. Myers, P. W. Li, R. J. Mural, et al. "The sequence of human genome," *Science* 291: 1304-1351 (2001).
11. G. Bejerano, D. Haussler, and M. Blanchette, "Into the heart of darkness: large-scale clustering of human non-coding DNA," *Bioinformatics*, 20, 1, i40-8 (2004).
12. E. Birney, J. A. Stamatoyannopoulos, A. Dutta et al., "Identification and analysis of functional elements in 1% of the human genome by the ENCODE pilot project," *Nature*, 447, 7146, 799-816 (2007).
13. S. R. Gill, M. Pop, R. T. DeBoy et al., "Metagenomic analysis of the human distal gut microbiome," *Science*, 312, 5778, 1355-1359, (2006).
14. L. D. Wood, D. W. Parsons, S. Jones et al., "The Genomic Landscapes of Human Breast and Colorectal Cancers," *Science*, 318, 5853, 1108-1113 (2007).
15. J. G. Paez, P. A. Janne, J. C. Lee et al., "EGFR mutations in lung cancer: Correlation with clinical response to gefitinib therapy," *Science*, 304, 5676, pp: 1497-1500 (2004).
16. D. S. Johnson, A. Mortazavi, R. M. Myers et al., "Genome-wide mapping of in vivo protein-DNA interactions," *Science*, 316, 5830,1497-1502 (2007).
17. A. Barski, S. Cuddapah, K. R. Cui et al., "High-resolution profiling of histone methylations in the human genome," *Cell*, 129, 4, 823-837 (2007).
18. P. Callinan, and A. Feinberg, "The emerging science of epigenomics," *Human Mol. Gen.*, 15, R95 (2006).
19. O. Morozova, and M. A. Marra, "Applications of next-generation sequencing technologies in functional genomics," *Genomics*, 92, 5, 255-264 (2008).
20. A. Marziali, and M. Akeson, "New DNA sequencing methods," *Ann Rev Biomed Eng*, 3, 195-223, (2001).
21. J. Kasianowicz, E. Brandin, D. Branton et al., "Characterization of individual polynucleotide molecules using a membrane channel," *Proceedings of the National Academy of Sciences*, 93, 24, 13770 (1996).
22. M. Akeson, D. Branton, J. J. Kasianowicz et al., "Microsecond Time-Scale Discrimination Among Segments Within Single RNA Molecules," *Biophys. J.*, 77, 6, 3227-3233 (1999).
23. Y. Astier, O. Braha, and H. Bayley, "Toward Single Molecule DNA Sequencing: Direct Identification of Ribonucleoside and Deoxyribonucleoside-Monophosphates by Using an Engineered Protein Nanopore Equipped with a Molecular Adapter," *J. Am. Chem. Soc.*, 128, 5, 1705 (2006).
24. J. Clarke, H-C Wu, L. Jayasinghe, A. Patel, S. Reid and H. Bayley, "Continuous base identification for single-molecule nanopore DNA sequencing," *Nat. Nanotechnol.* 4 265-270 (2009)

TABLE 2-continued

References

25. S. Cockroft, J. Chu, M. Amorin, H. Bayley, and M. Ghadiri A single-molecule nanopore device detects DNA polymerase activity with single-nucleotide resolution. *J. Am. Chem. Soc.* 130(3): 818 (2008).
26. D. Stoddart, A. J. Heron, E. Mikhailova, G. Maglia, and H. Bayley, "Single-nucleotide discrimination in immobilized DNA oligonucleotides with a biological nanopore," *Proceedings of National Academy of Sciences* 106 (19): 7702-7707 (2009).
27. E. R. Cruz-Chu, T. Ritz, Z. S. Siwy, K. Schulten, "Molecular control of ionic conduction in polymer nanopores," Faraday Disc. 143: 47-62 (2009). C. R. Martin, M. Nishizawa, K. Jiarge, M. Kang, and S. B. Lee"" *Adv. Mater.* 13: 1351-1362 (2001).
28. C. Ho, R. Qiao, J. B. Heng, A. Chatterjee, R. Timp, N. R. Aluru, G. Timp, "Electrolytic transport through a synthetic nanometer-diameter pore", *Proceedings of National Academy of Sciences*, 102 (30): 10445-10450 (2005).
29. J. B. Heng, A. Aksimentiev, C. Ho, V. Dimitrov, T. W. Sorsch, J. F. Miner, W. M. Mansfield, K. Schulten, G. Timp, "Beyond the gene chip," Bell Labs Tech. Journ. 10(3): 5-22 (2005).
30. V. Dimitrov, A. Aksimentiev, K. Schulten, J. B. Heng, T. W. Sorsch, W. M. Mansfield, J. F. Miner, G. P. Watson, R. Cirelli, F. Klemens, J. Bower, E. Ferry, A. Taylor, A. Kornblit, B. Dorvel, Q. Zhao, and G. Timp, "Exploring the Prospects for a Nanometer-scale Gene Chip," IEDM Proceedings. 169-172 (2006).
31. M. D. Fischbein and M. Drndić, "Sub-10 nm Device Fabrication in a Transmission Electron Microscope," *Nano Lett.* 7 (5): 1329-1337 (2007).
32. C. R. Martin, M. Nishizawa, K. Jiarge, M. Kang, and S. B. Lee, "Controlling Ion Transport Selectively in Gold Nanotubule Membranes," *Adv. Mater.* 13: 1351-1362 (2001).
33. J. Li, D. Stein, C. McMullan et al., "Ion-beam sculpting at nanometre length scales," *Nature*, vol. 412, 6843, 166-169, (2001).
34. Z. Siwy, and A. Fulinski, "Fabrication of a synthetic nanopore ion pump," *Physical Review Letters*, 89 (19) 4 (2002).
35. A. J. Storm, J. H. Chen, X. S. Ling et al., "Fabrication of solid-state nanopores with single-nanometre precision," *Nature Materials*, 2, (8) 537-540 (2003).
36. J. B. Heng, A. Aksimentiev, C. Ho, P. Marks, Y. V. Grinkova, S. Sligar, K. Schulten, and G. Timp, "The Electromechanics of DNA in a Synthetic Nanopore," *Biophys. J.*, 90: 1098-1106 (2006).
37. J. B. Heng, A. Aksimentiev, C. Ho, P. Marks, Y. V. Grinkova, S. Sligar, K. Schulten, and G. Timp, "Stretching DNA using the Field in a Synthetic Nanopore," *NanoLet.*, 5(10): 1883-1888 (2005).
38. J. Nakane, M. Akeson, A. Marziali, "Evaluation of nanopores as candidates for electronic analyte detection," *Electrophoresis* 23(16): 2592-2601 (2002).
39. B. Luan, and A. Aksimentiev, "Strain softening in stretched DNA," *Physical Review Letters*, 101, 11 (2008).
40. Q. Zhao, J. Comer, V. Dimitrov, S. Yemenicioglu, A. Aksimentiev, and G. Timp, "Stretching and Unzipping Nucleic Acid Hairpins Using a Synthetic Nanopore", *Nucleic Acids Research*, 36, 5 1532-1541, (2008).
41. J. Comer, V. Dimitrov, Q. Zhao, G. Timp, A. Aksimentiev, "Microscopic Mechanics of Hairpin DNA Translocation through Synthetic Nanopores", *Biophys. J.* 96: 593-608, (2009).
42. U. Mirsaidov, W. Timp, X. Zou, V. Dimitrov, K. Schulten, A. P. Feinberg, and G. Timp "Nano-electromechanics of Methylated DNA in a Nanopore," *Biophys. J. Lett.* 96(4) (2009).
43. H. Lederer, R. P. May, J. K. Kjems, G. Baer, and H. Heumann, "Solution Structure of a Short DNA Fragment Studied by Neutron-Scattering," *Eur. J. Biochem.* 161(1): 191-196 (1986).
44. I. Goychuk and P. Hanggi, "Ion channel gating: A first-passage time analysis of the Kramers type," *Proceedings of the National Academy of Sciences* 99: 3552 (2002).
48. D. Fologea, J. Uplinger, B. Thomas, D. S. McNabb, and J. L. Li, "Slowing DNA translocation in a solid-state nanopore," *Nano Lett.* 5(9): 1734-1737 (2005).
49. A. J. Storm, et al. "Fast DNA translocation through a solid-state nanopore," *Nano Lett.* 5(7): 1193 (2005).
50. N. Ashkenasy, J. Sanchez-Quesada, H. Bayley, M. R. Ghadiri, "Recognizing a single base in an individual DNA strand: A step toward DNA sequencing in nanopores," *Angew. Chem. Int. Ed. Engl.*, 44: 1401-1404 (2005).
51. J. Mathé, H. Visram, V. Viasnoff, Y. Rabin, A. Meller, "Nanopore unzipping of individual DNA hairpin molecules," *Biophys. J.*, 87 3205-3212 (2004).
52. J. Mathé, A. Arinstein, Y. Rabin, A. Meller, "Equilibrium and irreversible unzipping of DNA in a nanopore," *Europhys. Lett.*, 73: 128-134 (2006).
53. O. K. Dudko, J. Mathe, A. Szabo, A. Meller and G. Hummer, "Extraction Kinetics from Single-Molecule Force Spectroscopy: Nanopore Unzipping of DNA Hairpins," *Biophys. J.*, 92: 4188-4195 (2007).
54. A. F. Sauer-Budge, J. A. Nyamwanda, O. K. Lubensky and D. Branton, "Unzipping kinetics of double-stranded DNA in a nanopore," *Phys. Rev. Lett.* 90: 238101 (2003).
55. R. McGillivray R and R. Wald, "Dual-path capacitance compensation network for microelectrode recordings," *Am. J. Physiol.* 238 H930-H1 (1980).
56. F. N. Hooge and J. L. M. Gaal, "Fluctuations with a 1lf spectrum in the conductance of ionic solutions and in the voltage of concentration cells," *Philips Res. Rpts.* 26, 77 (1971).
57. D. L. Dorset and H. M. Fishman, Excess Electrical Noise During Current Flow Through Porous Membranes Separating Ionic Solutions, *J. Membrane Biol.* 21, 291-309 (1975).
58. R. Smeets, U. Keyser, N. Dekker et al., "Noise in solid-state nanopores," *Proc. Nat. Acad. Sci.*, 105, 2, 417 (2008).
59. R. M. M. Smeets, N H Dekker and C Dekker (2009) Low-frequency noise in solid-state nanopores *Nanotechnology* 20 095501.
60. C. Yuan, A. Chen, P. Kolb, and V. Moy, "Energy Landscape of Streptavidin Biotin Complexes Measured by Atomic Force Microscopy,". *Biochemistry* 39(33): 10219-10223 (2000).

TABLE 2-continued

References

61. N. Cady, S. Stelick, and C. Batt, "Nucleic acid purification using microfabricated silicon structures," *Biosensors and Bioelectronics* 19(1): 59-66 (2003).
62. W. Im and B. Roux, "Ions and counterions in a biological channel: a molecular dynamics study of OmpF porin from *Escherichia coli* in an explicit membrane with 1M KCl aqueous salt solution," *J. Mol. Biol.*, 319: 1177-1197 (2002).
63. W. Im, S. Seefeld, and B. Roux, "A grand canonical Monte Carlo-Brownian Dynamics algorithm for simulating ion channels," *Biophys. J.*, 79: 788-801 (2000).
64. S. Y. Noskov, W. Im, and B. Roux, "Ion permeation through the α-hemolysin channel: Theoretical studies based on Brownian Dynamics and Poisson-Nernst-Plank electrodiffusion theory," *Biophys. J.*, 87: 2299-2309 (2004).
65. B. Roux, "The calculation of the potential of mean force using computer simulations," *Comp. Phys. Comm.*, 91: 275-282 (1995).
66. B. V. Zhurnd, A. Meurk, and L. Bergstrom, "Evaluation of Surface Ionization Parameters from AFM Data," *J. Colloid Interface Sci.* 207: 332-343 (1998).
67. C. R. Helms, *The Physics and Chemistry of SiO2 and Si—SiO2 Interface*. Plenum Press, New York, (1988).
68. R. K. Iler, *The Chemistry of Silica*. Wiley, New York (1979).
69. J. S. Marcus, W. F. Anderson, S. R. Quake, "Microfluidic single-cell MRNA isolation and analysis," *Anal. Chem.* 78(9): 3084-3089 (2006).
70. J. Melin and S. R. Quake, "Microfluidic Large-Scale Integration: The Evolution of Design Rules for Biological Automation," *Annu. Rev. Biophys. Biomol. Struct.* 36: 213-231 (2007).
71. P. R. Nair and M. A. Alam, "Performance limits of nanobiosensors," *Appl. Phys. Lett.* 88: 233120 (2006)
72. H. C. Berg, *Random walks in biology*, Princeton University Press, Princeton, N.J. (1993).
73. G. Durack, "Cell Sorting Techniques and Technologies," *Emerging Tools for Single Cell Analysis: Advances in optical measurement technologies*," Wiley-Liss, 2000, ISBN 0-471-31575-3.
74. R. Scott, P. Sethu, C. K. Harnett, "3D hydrodynamic focusing in a microfluidic," *Rev. Sci. Instru.*, 79, 046104 (2008).
75. J. B. Heng, C. Ho, T. Kim, R. Timp, A. Aksimentiev, Y. V. Grinkova, S. Sligar, K. Schulten, and G. Timp, "Sizing DNA Using a Nanometer-Diameter Pore," *Biophys. J.*, 87: 2905-2911 (2004).
76. A. Aksimentiev, J. B. Heng, G. Timp, and K. Schulten, "Microscopic Kinetics of DNA Translocation through Synthetic Nanopores," Biophys. J., 87: 2086-2097 (2004).
77. E. R. Cruz-Chu, A. Aksimentiev and K. Schulten, "Water-silica force field for simulating nanodevices," *J. Phys. Chem. B*, 110: 21497-21508 (2006).
78. J. Sonnefeld, M. Lobbus, W. Vogelsberger, "Determination of electric double layer parameters for spherical silica particles under application of the triple layer model using surface charge density data and results of electrokinetic sonic amplitude," *Colloid Surf. A-Physicochem. Eng. Asp.*, 195, 215 (2001).
79. W. Saenger *Principles of Nucleic Acid Structure* Springer-Verlag, New York (1984).
80. T. Ha, I. Rasnik, W. Cheng, H. P. Babcock, G. H. Gauss, T. M. Lohman and S. Chu, "Initiation and re-initiation of DNA unwinding by the *Escherichia coli* Rep helicase," *Nature* 419: 638-641 (2002).
81. J. Nilsson, J. R. I. Lee, T, V. Ratto, S. E. Létant, "Localized Functionalization of Single Nanopores," *Adv. Materials*, 18: 427-431 (2006).
82. M. Wanunu and A. Meller, "Chemically Modified Solid-State Nanopores," *Nano Lett.*, 7, 1580-85 (2007).
83. R. E. Gyurcsányi, "Chemically-modified nanopores for sensing," *Analytical Chemistry*, 27(7) 627-639 (2008).
84. R. H. Dicke, *Rev. Sci. Instruments.* 17(7), 268-275 (1946).
85. J. H. Scofield, Am. J. Phys. 62(2), 129-133 (1994).
86. J. Wang, L. W. Quo, H. Q. Jia, Y. Wang, Z. G. Xing, W. Li, H. Chen, and J. M. Zhou, "Fabrication of Patterned Sapphire Substrate by Wet Chemical Etching for Maskless Lateral Overgrowth of GaN," *J. Electrochem. Soc.*, 153 (3): C182-C185 (2006).
87. C. H. Jeong, D. W. Kim, K. N. Kim, and G. Y. Yeom, "A Study of Sapphire Etching Characteristics Using $BCl_3$-based Inductively Coupled Plasmas," Jap. J. Appl. Phys., 41(10) 6206 (2002).
88. A. Aksimentiev and K. Schulten, "Imaging alpha-hemolysin with molecular dynamics: Ionic conductance, osmotic permeability and the electrostatic potential map,". *Biophys. J.*, 88: 3745-3761 (2005).
89. D. E. Shaw, et al. Anton, a special-purpose machine for molecular dynamics simulation. International Symposium on Computer Architecture, *ACM*, 1-12, (2007).
90. M. Muthukumar and C. Y. Kong, C. Y. Simulation of polymer translocation through protein channels. *Proc. Natl. Acad. Sci. USA*, 103, 5273-5278 (2006).
91. S. van Dorp, N. H. Dekker, C. Dekker, and S. G. Lemay, "Origin of the electrophoretic force on DNA in solid-state nanopores," *Nature Phys.* 5, 347-351 (2009).
92. Q. Zhao, G. Sigalov, V. Dimitrov, B. Dorvel, U. Mirsaidov, S. Sligar, A. Aksimentiev, and G. Timp, "Detecting SNPs using a Synthetic Nanopore," *NanoLetters*, 7(6); 1680-1685 (2007).
93. B. Dorvel, G. Sigalov, Q. Zhao, C. Hyun, V. Dimitrov, A. Aksimentiev, and G. Timp, "Analyzing the Forces Binding Restriction Endonucleases to DNA," submitted to *Proc. Nat. Acad. Sci. USA* (2008).

We claim:

1. A method of characterizing at least a portion of a double-stranded polynucleotide, said method comprising:
providing a membrane having a nanopassage that defines a confine region, wherein said membrane separates a first fluid compartment from a second fluid compartment, and said nanopassage is in fluid communication with the first and second compartments;
providing said double-stranded polynucleotide to said first fluid compartment;
establishing a driving voltage bias that is greater than a threshold voltage across said membrane to force a portion of said double-stranded polynucleotide into said nanopassage, wherein said portion of said double-stranded polynucleotide has a confined portion positioned within said confine region and said confine region deforms said double-stranded polynucleotide by increasing axial rise from an undeformed axial rise value to a deformed axial rise value in said confine region or a region adjacent thereto;
monitoring an electrical current through said nanopassage;
identifying a confine state from said a monitored electrical current from said monitoring step, wherein said confine state corresponds to said confined portion containing a confined nucleotide base-pair of said polynucleotide in said confine region;
reducing said driving voltage bias to a holding voltage that is less than or equal to said threshold voltage, thereby trapping said confined nucleotide base-pair in said nanopassage confine region for a trapping time, wherein said trapping time is selected from a range that is greater than or equal to 10 ns and less than or equal to 1 second; and
measuring a nucleotide base-pair dependent current blockade through said nanopassage confine region having said confined nucleotide base-pair during said trapping time, to characterize the confined nucleotide base-pair, thereby characterizing at least a portion of said polynucleotide.

2. The method of claim 1, further comprising:
establishing a translocation voltage bias that is greater than the threshold voltage to force said confined nucleotide base-pair out of said confine region in a direction that is toward said second compartment;
repeating said monitoring, identifying, reducing and measuring steps to thereby characterize a confined nucleotide base-pair that is at a position upstream from the previously characterized confined nucleotide.

3. The method of claim 2, wherein the characterized confined nucleotides base-pair are nucleotide base-pairs adjacent to each other in said polynucleotide.

4. The method of claim 2, further comprising repeating the steps of claim 2 to characterize a contiguous portion of said polynucleotide, wherein said contiguous portion corresponds to at least 10% of the entire length of said polynucleotide.

5. The method of claim 4, wherein said contiguous portion corresponds to the entire length of said polynucleotide.

6. The method of claim 2, wherein said translocation voltage is less than said driving voltage bias.

7. The method of claim 2, wherein said holding voltage is applied for a holding time sufficient to provide high-fidelity assessment of said confined nucleotide base-pair.

8. The method of claim 2 wherein said polynucleotide travels in a direction from said first compartment to said second compartment at a translocation velocity that is greater than or equal to 1 nucleotide per 10 nanoseconds or greater than or equal to 1 nucleotide base pair per 10 nanoseconds.

9. The method of claim 2, further comprising: diagnosing a medical condition for a patient from which the polynucleotide is obtained.

10. The method of claim 9 wherein the medical condition relates to a specific polynucleotide sequence.

11. The method of claim 9, wherein the medical condition relates to a methylation parameter.

12. The method of claim 2, wherein the translocation voltage bias is a voltage pulse having a duration that is less than or equal to 1 μs.

13. The method of claim 2, wherein the magnitude of said translocation voltage bias is at least two times greater than said holding voltage.

14. The method of claim 1, wherein said polynucleotide translocates unidirectionally from said first compartment to said second compartment.

15. The method of claim 1, further comprising determining said threshold voltage for said nanopassage and said polynucleotide.

16. The method of claim 1, wherein said characterizing is one or more of identifying a nucleotide-type, a nucleotide base-pair type or nucleotide methylation state.

17. The method of claim 1 wherein said characterization is methylation content, methylation pattern, or methylation content and pattern.

18. The method of claim 1, wherein said characterization is determining at least a portion of said polynucleotide sequence.

19. The method of claim 1 wherein said deformed axial rise value is at least 20% greater than the undeformed axial rise value.

20. The method of claim 1, wherein said deformed axial rise value is selected from a range that is greater than or equal to 0.34 nm and less than or equal to 0.7 nm.

21. The method of claim 1, wherein said characterization comprises determining the sequence of at least 2000 contiguous bases.

22. The method of claim 1, wherein said confine region has a minimum cross-sectional area that is less than or equal to 4.4 $nm^2$.

23. The method of claim 22, wherein said nanopassage is a tapered nanopore having a maximum diameter that is less than or equal to 2.6 nm and a minimum diameter centered in said confine region that is selected from a range that is greater than or equal to 1 nm and less than or equal to 2.4 nm.

24. The method of claim 1, wherein said membrane is a $Si_3N_4$ membrane having a thickness selected from a range that is greater than or equal to 5 nm and less than or equal to 30 nm.

25. The method of claim 1, wherein one nucleotide of said confined nucleotide base-pair is uniquely identified with one strand of said double stranded polynucleotide.

26. The method of claim 1, further comprising the step of obtaining a high fidelity measure of the nucleotide base-pair dependent current blockade by measuring the nucleotide base-pair dependent current blockade over the trapping time and calculating an average nucleotide base-pair dependent current blockade over the trapping time.

27. A method of trapping a portion of a double-stranded polynucleotide in a membrane nanopassage, said method comprising the steps of:
providing a membrane having a nanopassage that defines a confine region, wherein said membrane separates a first fluid compartment from a second fluid compartment, and said nanopassage is in fluid communication with the first and second compartments;

providing said double-stranded polynucleotide to said first fluid compartment;

determining a threshold voltage for said membrane and said double-stranded polynucleotide;

establishing a driving voltage bias across said membrane that is greater than said threshold voltage, to force a portion of said double-stranded polynucleotide into said nanopassage confine region, wherein said portion of said double-stranded nucleotide in said confine region is deformed and said confine region deforms said double-stranded polynucleotide by increasing axial rise from an undeformed axial rise value to a deformed axial rise value in said confine region or a region adjacent thereto; and decreasing said driving voltage bias to a holding voltage bias, wherein said holding voltage bias is less than said threshold voltage, thereby trapping said polynucleotide portion in said nanopassage confine region for a trapping time, wherein said trapping time is selected from a range that is greater than or equal to 10 ns and less than or equal to 1 second, wherein at least one nucleotide base-pair is fixably positioned in said nanopassage confine volume during said trapping time.

28. The method of claim 27, further comprising:
measuring a blockade current through said nanopassage having at least one nucleotide base-pair positioned in said confine volume;

sequentially forcing said polynucleotide through said confine volume nucleotide base-pair by nucleotide base-pair by switching an electric field from a translocation voltage bias that is greater than said threshold voltage to said holding voltage bias at a switching frequency, wherein said holding voltage bias is applied when a nucleotide base-pair is positioned in said confine region, and said sequentially forcing step provides a nucleotide base-pair stepwise movement of said polynucleotide through said confine region in a direction from said first compartment to said second compartment so that every nucleotide base-pair within a contiguous length of said polynucleotide is trapped in said confine region and said blockade current is measured for each trapped nucleotide base-pair.

29. The method of claim 28, wherein the holding voltage bias corresponds to no voltage difference across said membrane.

30. The method of claim 27, wherein said holding voltage is applied for a holding time that is sufficient to provide high-fidelity measurement of said blockade current for said nucleotide base-pair positioned in said confine volume.

31. The method of claim 27, wherein said nanopassage confine region that traps said portion of polynucleotide has a minimum cross-sectional area that is 2.56 $nm^2$.

32. The method of claim 27, wherein said polynucleotide is DNA having a length that is greater than or equal to 200 base pairs.

33. The method of claim 27, wherein six or fewer base pairs are trapped in said nanopassage interior volume.

34. The method of claim 27, wherein the nanopassage is a pore having a minimum diameter that is smaller than an average diameter of said polynucleotide that is trapped.

35. The method of claim 27, further comprising measuring an electrical blockade current across said nanopassage for said trapped portion.

36. A method of sequencing a double-stranded polynucleotide, said method comprising:
providing a membrane having a nanopassage that defines a confine region having a minimum dimension that is less than an average axial diameter of said double-stranded polynucleotide, wherein said membrane separates a first fluid compartment from a second fluid compartment, and said nanopassage is in fluid communication with the first and second compartments;

providing said double-stranded polynucleotide to said first fluid compartment;

establishing a driving voltage bias that is greater than a threshold voltage across said membrane to force a portion of said double-stranded polynucleotide into said nanopassage, wherein said portion of said double-stranded polynucleotide has a confined portion positioned within said confine region;

monitoring an electrical current through said nanopassage;

identifying said confined portion as a confined nucleotide base-pair from a monitored electrical current from said monitoring step;

reducing said driving voltage bias to a holding voltage that is less than or equal to said threshold voltage, thereby trapping said confined nucleotide base-pair in said nanopassage confine region for a trapping time, wherein said trapping time is selected from a range that is greater than or equal to 10 ns and less than or equal to 1 second;

measuring a nucleotide-dependent current blockade through said nanopassage confine region having said confined nucleotide base-pair during said trapping time, to identify the confined nucleotide base-pair, thereby characterizing at least a portion of said polynucleotide;

establishing a translocation voltage bias that is greater than the threshold voltage to translocate said polynucleotide in a direction that is toward said second compartment, wherein said translocation moves said polynucleotide by one base-pair through the confine region;

repeating said monitoring, identifying, reducing and measuring steps to thereby identify a confined nucleotide base-pair that is at a single base-pair sequential position difference from the previously characterized confined nucleotide base-pair, thereby sequencing at least a portion of said double-stranded polynucleotide.

37. The method of claim 36 wherein the measuring step is repeated over the entire polynucleotide length, thereby sequencing the entire polynucleotide.

* * * * *

UNITED STATES PATENT AND TRADEMARK OFFICE
CERTIFICATE OF CORRECTION

| | | |
|---|---|---|
| PATENT NO. | : 8,748,091 B2 | Page 1 of 1 |
| APPLICATION NO. | : 12/971240 | |
| DATED | : June 10, 2014 | |
| INVENTOR(S) | : Timp et al. | |

It is certified that error appears in the above-identified patent and that said Letters Patent is hereby corrected as shown below:

In the Claims

In claim 1, column 43, line 23, replace "from said a monitored electrical" with --from a monitored electrical--

Signed and Sealed this
Twenty-first Day of October, 2014

Michelle K. Lee
*Deputy Director of the United States Patent and Trademark Office*